(12) United States Patent
Sirhan et al.

(10) Patent No.: US 7,077,859 B2
(45) Date of Patent: Jul. 18, 2006

(54) APPARATUS AND METHODS FOR VARIABLY CONTROLLED SUBSTANCE DELIVERY FROM IMPLANTED PROSTHESES

(75) Inventors: Motasim Sirhan, Sunnyvale, CA (US); John Yan, Los Gatos, CA (US)

(73) Assignee: Avantec Vascular Corporation, Sunnyvale, CA (US)

( * ) Notice: Subject to any disclaimer, the term of this patent is extended or adjusted under 35 U.S.C. 154(b) by 437 days.

(21) Appl. No.: 10/017,500

(22) Filed: Dec. 14, 2001

(65) Prior Publication Data

US 2003/0083646 A1 May 1, 2003

Related U.S. Application Data

(63) Continuation-in-part of application No. 10/002,595, filed on Nov. 1, 2001, and a continuation-in-part of application No. 09/783,253, filed on Feb. 13, 2001, and a continuation-in-part of application No. 09/782,927, filed on Feb. 13, 2001, now Pat. No. 6,471,980, and a continuation-in-part of application No. 09/783,254, filed on Feb. 13, 2001, and a continuation-in-part of application No. 09/782,804, filed on Feb. 13, 2001.

(60) Provisional application No. 60/308,381, filed on Jul. 26, 2001, and provisional application No. 60/258,024, filed on Dec. 22, 2000.

(51) Int. Cl.
*A61F 2/06* (2006.01)

(52) U.S. Cl. ...................................... 623/1.15; 623/1.42
(58) Field of Classification Search ................ 623/1.13, 623/1.39, 1.4–1.48
See application file for complete search history.

(56) References Cited

U.S. PATENT DOCUMENTS 3,705,894 A    12/1972   Gerzon et al.

(Continued)

FOREIGN PATENT DOCUMENTS

| EP | 063 365 B1 | 9/1985 |
| EP | 184 162 B1 | 4/1994 |
| WO | WO 90/13332 A1 | 11/1990 |
| WO | 0 923 953 A2 | 6/1999 |
| WO | WO 00/10622 A1 | 3/2000 |
| WO | WO 01/01957 | 1/2001 |

OTHER PUBLICATIONS

Mohacsi et al., "Different inhibitory effects of immunosuppresive drugs on hyman and rat aortic smooth muscle and endothelial cell proliferation stimulated by platelet–derived growth factor or endothelial cell growth factor" *J Heart and Lung Transplant,* 16:484–491 (1997).

Lincoff, Michael A. et al., "Local Drug Delivery for the Prevention of Restenosis" Coated Stents; *Circulation vol. 90, No. 4;* Oct. 1994 p. 2075.

*Primary Examiner*—Corrine McDermott
*Assistant Examiner*—Hieu Phan
(74) *Attorney, Agent, or Firm*—Townsend and Townsend and Crew LLP

(57) ABSTRACT

The present invention provides improved stents and other prostheses for delivering substances to vascular and other luminal and intracorporeal enviroments. In particular, the present invention provides luminal prostheses which allow for a programmed and controlled substance delivery protocols for a variety of purposes. The prostheses comprise a scaffold which is implantable within a body lumen and a substance reservoir present over at least a portion of the scaffold. Usually, a rate-controlling element will be formed over the substance-containing reservoir to provide for a number of different substance release characteristics.

31 Claims, 34 Drawing Sheets

U.S. PATENT DOCUMENTS

| | | |
|---|---|---|
| 3,705,948 A | 12/1972 | Dyke et al. |
| 3,777,020 A | 12/1973 | Johnson |
| 3,854,480 A | 12/1974 | Zaffaroni |
| 3,868,454 A | 2/1975 | Johnson |
| 3,880,995 A | 4/1975 | Jones |
| 3,903,071 A | 9/1975 | Holmes |
| 3,976,071 A | 8/1976 | Sadek |
| 3,993,072 A | 11/1976 | Zaffaroni |
| 3,993,749 A | 11/1976 | Sehgal et al. |
| 4,115,197 A | 9/1978 | Queener et al. |
| 4,234,684 A | 11/1980 | Abbott et al. |
| 4,335,094 A | 6/1982 | Mosbach |
| 4,345,588 A | 8/1982 | Widder et al. |
| 4,357,259 A | 11/1982 | Senyei et al. |
| 4,501,726 A | 2/1985 | Schröder et al. |
| 4,788,063 A | 11/1988 | Fisher et al. |
| 4,810,524 A | 3/1989 | Nakayama et al. |
| 4,832,686 A | 5/1989 | Anderson |
| 4,871,716 A | 10/1989 | Longo et al. |
| 4,883,666 A | 11/1989 | Sabel et al. |
| 4,894,231 A | 1/1990 | Moreau et al. |
| 4,897,268 A | 1/1990 | Tice et al. |
| 4,904,479 A | 2/1990 | Illum |
| 4,921,723 A | 5/1990 | Nichols et al. |
| 4,936,281 A | 6/1990 | Stasz |
| 5,000,185 A | 3/1991 | Yock |
| 5,024,671 A | 6/1991 | Tu et al. |
| 5,067,491 A | 11/1991 | Taylor, II et al. |
| 5,069,216 A | 12/1991 | Groman et al. |
| 5,112,457 A | 5/1992 | Marchant |
| 5,130,889 A | 7/1992 | Hamburgen et al. |
| 5,163,952 A | 11/1992 | Froix |
| 5,176,907 A | 1/1993 | Leong |
| 5,206,159 A | 4/1993 | Cohen et al. |
| 5,225,282 A | 7/1993 | Chagnon et al. |
| 5,243,756 A | 9/1993 | Hamburgen et al. |
| 5,270,047 A | 12/1993 | Kauffman et al. |
| 5,283,257 A | 2/1994 | Gregory et al. |
| 5,286,254 A | 2/1994 | Shapland et al. |
| 5,288,504 A | 2/1994 | Versic |
| 5,342,348 A | 8/1994 | Kaplan |
| 5,355,832 A | 10/1994 | Loh et al. |
| 5,356,433 A | 10/1994 | Rowland et al. |
| 5,368,557 A | 11/1994 | Nita et al. |
| 5,409,000 A | 4/1995 | Imran |
| 5,411,550 A | 5/1995 | Herweck et al. |
| 5,419,760 A | 5/1995 | Narciso, Jr. |
| 5,427,767 A | 6/1995 | Kresse et al. |
| 5,428,123 A | 6/1995 | Ward et al. |
| 5,447,724 A | 9/1995 | Helmus et al. |
| 5,447,799 A | 9/1995 | Loh et al. |
| 5,463,010 A | 10/1995 | Hu et al. |
| 5,464,450 A | 11/1995 | Buscemi et al. |
| 5,464,650 A | 11/1995 | Berg et al. |
| 5,470,802 A | 11/1995 | Gnade et al. |
| 5,474,563 A | 12/1995 | Myler et al. |
| 5,484,584 A | 1/1996 | Wallace et al. |
| 5,488,015 A | 1/1996 | Havemann et al. |
| 5,500,013 A | 3/1996 | Buscemi et al. |
| 5,516,781 A | 5/1996 | Morris et al. |
| 5,543,158 A | 8/1996 | Gref et al. |
| 5,545,208 A | 8/1996 | Wolff et al. |
| 5,551,954 A | 9/1996 | Buscemi et al. |
| 5,563,146 A | 10/1996 | Morris et al. |
| 5,569,463 A | 10/1996 | Helmus et al. |
| 5,591,227 A | 1/1997 | Dinh et al. |
| 5,609,629 A | 3/1997 | Fearnot et al. |
| 5,624,411 A | 4/1997 | Tuch |
| 5,637,113 A | 6/1997 | Tartaglia et al. |
| 5,646,160 A | 7/1997 | Morris et al. |
| 5,649,977 A | 7/1997 | Campbell |
| 5,656,297 A | 8/1997 | Bernstein et al. |
| 5,665,728 A | 9/1997 | Morris et al. |
| 5,679,400 A | 10/1997 | Tuch |
| 5,700,286 A | 12/1997 | Tartaglia et al. |
| 5,725,494 A | 3/1998 | Brisken |
| 5,725,567 A | 3/1998 | Wolff et al. |
| 5,728,062 A | 3/1998 | Brisken |
| 5,735,811 A | 4/1998 | Brisken |
| 5,769,883 A | 6/1998 | Buscemi et al. |
| 5,769,884 A | 6/1998 | Solovay |
| 5,824,049 A | 10/1998 | Ragheb et al. |
| 5,837,008 A | 11/1998 | Berg et al. |
| 5,843,172 A | 12/1998 | Yan |
| 5,851,231 A | 12/1998 | Wolff et al. |
| 5,876,452 A | 3/1999 | Athanasiou et al. |
| 5,879,808 A | 3/1999 | Wary et al. |
| 5,891,108 A | 4/1999 | Leone et al. |
| 5,893,840 A | 4/1999 | Hull et al. |
| 5,928,145 A | 7/1999 | Ocali et al. |
| 5,951,586 A | 9/1999 | Berg et al. |
| 5,958,510 A | 9/1999 | Sivaramakrishnam et al. |
| 5,968,092 A | 10/1999 | Buscemi et al. |
| 5,972,027 A | 10/1999 | Johnson |
| 5,980,551 A | 11/1999 | Summers et al. |
| 5,980,566 A | 11/1999 | Alt et al. |
| 5,997,468 A | 12/1999 | Wolff et al. |
| 6,031,375 A | 2/2000 | Atalar et al. |
| 6,051,276 A | 4/2000 | Wary et al. |
| 6,063,101 A | 5/2000 | Jacobsen et al. |
| 6,071,305 A | 6/2000 | Brown et al. |
| 6,086,952 A | 7/2000 | Lang et al. |
| 6,096,070 A | 8/2000 | Ragheb et al. |
| 6,099,561 A | 8/2000 | Alt |
| 6,107,052 A | 8/2000 | Dorn |
| 6,153,252 A | 11/2000 | Hossainy et al. |
| 6,183,507 B1 | 2/2001 | Lashinski et al. |
| 6,240,616 B1 * | 6/2001 | Yan .................. 29/527.2 |
| 6,253,443 B1 | 7/2001 | Johnson |
| 6,273,908 B1 | 8/2001 | Ndondo-Lay |
| 6,273,913 B1 | 8/2001 | Wright et al. |
| 6,287,628 B1 | 9/2001 | Hossainy et al. |
| 6,299,604 B1 | 10/2001 | Ragheb et al. |
| 6,395,326 B1 | 5/2002 | Castro et al. |
| 6,471,980 B1 * | 10/2002 | Sirhan et al. ............ 424/423 |
| 6,613,082 B1 * | 9/2003 | Yang .................. 623/1.42 |
| 6,663,662 B1 * | 12/2003 | Pacetti et al. ........... 623/1.13 |
| 2001/0027340 A1 | 10/2001 | Wright et al. |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0016625 A1 | 2/2002 | Falotico et al. |
| 2002/0032414 A1 | 3/2002 | Ragheb et al. |

* cited by examiner

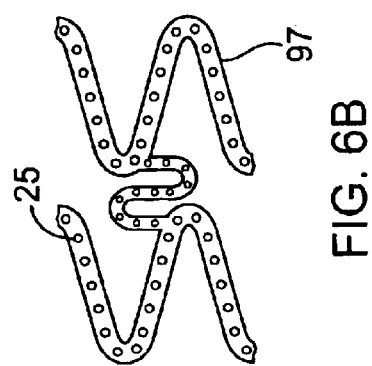
FIG. 6A
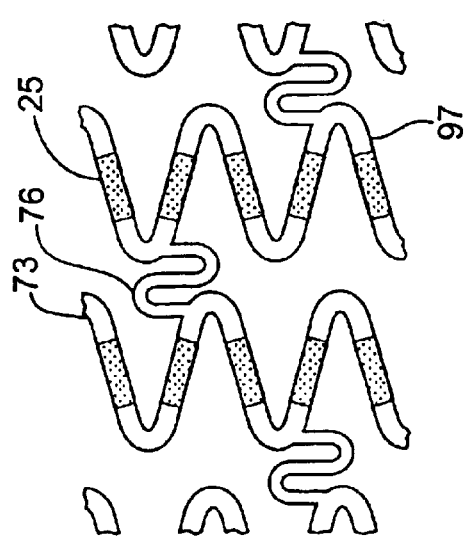
FIG. 6B
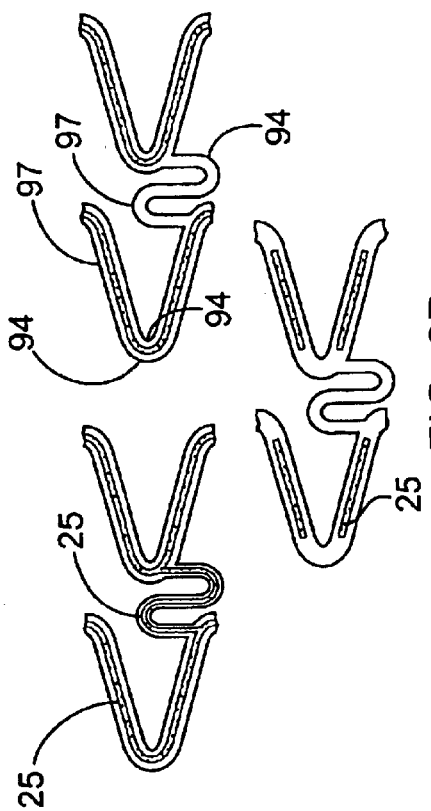
FIG. 6C
FIG. 6D

APPARATUS AND METHODS FOR VARIABLY CONTROLLED SUBSTANCE DELIVERY FROM IMPLANTED PROSTHESES

CROSS-REFERENCES TO RELATED APPLICATIONS

This application is a continuation-in-part and claims the benefit of Non-Provisional U.S. patent application Ser. No. 10/002,595, filed Nov. 1, 2001. which claims the benefit of Provisional U.S. Patent Application 60/258,024, filed on Dec. 22, 2000; and is a continuation-in-part of U.S. patent applications Ser. Nos. 09/783,253, 09/782,927, now U.S. Pat No. 6,471,980, Ser. Nos. 09/783,254, and 09/782,804, all filed on Feb. 13. 2001; and which claims the benefit of Provisional U.S. Patent Application 60/308,381, filed on Jul. 26, 2001. Each of these applications is assigned to the assignee of the present application. The full disclosures of each of the above applications is incorporated herein by reference.

BACKGROUND OF THE INVENTION

1. Field of the Invention

The present invention relates generally to medical devices and methods. More particularly, the present invention provides luminal prostheses, such as vascular stents and grafts for reducing or inhibiting restenosis.

The present invention relates generally to medical devices and methods. More particularly, the present invention provides luminal prostheses, such as vascular stents and grafts for reducing or inhibiting restenosis.

A number of percutaneous intravascular procedures have been developed for treating stenotic atherosclerotic regions of a patient's vasculature to restore adequate blood flow. The most successful of these treatments is percutaneous transluminal angioplasty (PTA). In PTA, a catheter, having an expandable distal end usually in the form of an inflatable balloon, is positioned in the blood vessel at the stenotic site. The expandable end is expanded to dilate the vessel to restore adequate blood flow beyond the diseased region. Other procedures for opening stenotic regions include directional arthrectomy, rotational arthrectomy, laser angioplasty, stenting, and the like. While these procedures have gained wide acceptance (either alone or in combination, particularly PTA in combination with stenting), they continue to suffer from significant disadvantages. A particularly common disadvantage with PTA and other known procedures for opening stenotic regions is the frequent occurrence of restenosis.

Restenosis refers to the re-narrowing of an artery after an initially successful angioplasty. Restenosis afflicts approximately up to 50% of all angioplasty patients and is the result of injury to the blood vessel wall during the lumen opening angioplasty procedure. In some patients, the injury initiates a repair response that is characterized by smooth muscle cell proliferation referred to as "hyperplasia" in the region traumatized by the angioplasty. This proliferation of smooth muscle cells re-narrows the lumen that was opened by the angioplasty within a few weeks to a few months, thereby necessitating a repeat PTA or other procedure to alleviate the restenosis.

A number of strategies have been proposed to treat hyperplasia and reduce restenosis. Previously proposed strategies include prolonged balloon inflation during angioplasty, treatment of the blood vessel with a heated balloon, treatment of the blood vessel with radiation following angioplasty, stenting of the region, and other procedures. While these proposals have enjoyed varying levels of success, no one of these procedures is proven to be entirely successful in substantially or completely avoiding all occurrences of restenosis and hyperplasia.

As an alternative or adjunctive to the above mentioned therapies, the administration of therapeutic agents following PTA for the inhibition of restenosis has also been proposed. Therapeutic treatments usually entail pushing or releasing a therapeutic capable agent through a catheter or from a stent. While holding great promise, the delivery of therapeutic agents for the inhibition of restenosis has not been entirely successful.

As an alternative or adjunctive to the above mentioned therapies, the administration of therapeutic agents following PTA for the inhibition of restenosis has also been proposed. Therapeutic treatments usually entail pushing or releasing a drug through a catheter or from a stent. While holding great promise, the delivery of therapeutic agents for the inhibition of restenosis has not been entirely successful.

Accordingly, it would be a significant advance to provide improved devices and methods for reducing, inhibiting, or treating restenosis and hyperplasia which may follow angioplasty and other interventional treatments. This invention satisfies at least some of these and other needs.

2. Description of the Background Art

Local drug delivery for the prevention of restenosis is described in Lincoff et al. (1994) Circulation 90:2070–2084. A full description of an exemplary luminal prosthesis for use in the present invention is described in co-pending application Ser. No. 09/565,560 filed May 4, 2000, the full disclosure of which is incorporated herein by reference. Method and apparatus for releasing active substances from implantable and other devices are described in U.S. Pat. Nos. 6,096,070; 5,824,049; 5,624,411; 5,609,629; 5,569,463; 5,447,724; and 5,464,650. The use of stents for drug delivery within the vasculature are described in PCT Publication No. WO 01/01957 and U.S. Pat. Nos. 6,099,561; 6,071,305; 6,063,101; 5,997,468; 5,980,551; 5,980,566; 5,972,027; 5,968,092; 5,951,586; 5,893,840; 5,891,108; 5,851,231; 5,843,172; 5,837,008; 5,769,883; 5,735,811; 5,700,286; 5,679,400; 5,649,977; 5,637,113; 5,591,227; 5,551,954; 5,545,208; 5,500,013; 5,464,450; 5,419,760; 5,411,550; 5,342,348; 5,286,254; and 5,163,952. Biodegradable materials are described in U.S. Pat. Nos. 6,051,276; 5,879,808; 5,876,452; 5,656,297; 5,543,158; 5,484,584; 5,176,907; 4,894,231; 4,897,268; 4,883,666; 4,832,686; and 3,976,071. The use of hydrocylosiloxane as a rate limiting barrier is described in U.S. Pat. No. 5,463,010. Methods for coating of stents is described in U.S. Pat. No. 5,356,433. Coatings to enhance biocompatibility of implantable devices are described in U.S. Pat. Nos. 5,463,010; 5,112,457; and 5,067, 491. Porous and non-porous materials for drug delivery, coating, and other uses are described in U.S. Pat. Nos. 5,488,015; 5,470,802; 5,428,123; 5,288,504; 5,270,047; 5,243,756; 5,130,889; 4,788,063; 3,993,072; and 3,854,480. Energy-based devices are described in U.S. Pat. Nos. 6,031, 375; 5,928,145; 5,735,811; 5,728,062; 5,725,494; 5,409, 000, 5,368,557; 5,000,185; and 4,936,281. Magnetic processes, some of which have been used in drug delivery systems, are described in U.S. Pat. Nos. 5,427,767; 5,225, 282; 5,206,159; 5,069,216; 4,904,479; 4,871,716; 4,501, 726; 4,357,259; 4,345,588; and 4,335,094.

The disclosure of this application is related to the disclosures of the following applications: Ser. No. 09/782,927, now U.S. Pat. No. 6,471,980; Ser. No. 09/783,254; and Ser. No. 09/782,804.

The full disclosures of each of the above references are incorporated herein by reference.

BRIEF SUMMARY OF THE INVENTION

The present invention is directed to improved devices for preparation or treatment of susceptible tissue sites, and methods making and using the same. In particular, the present invention is directed to corporeal, more particularly intracorporeal devices. In one embodiment, the present devices and methods reduce the formation or progression of restenosis and/or hyperplasia which may follow an intravascular intervention. In an embodiment, the device provides a therapeutic capable agent to the susceptible tissue site. Preferably, the therapeutic capable agent is provided to the therapeutic capable agent in a manner as to become available, immediately or after a delay period, to the susceptible tissue site upon introduction of the device to the corporeal body.

As used herein, "susceptible tissue site" refers to a tissue site that is injured, or may become injured as a result of an impairment (e.g., disease, medical condition), or may become injured during or following an interventional procedure such as an intravascular intervention. The term "intravascular intervention" includes a variety of corrective procedures that may be performed to at least partially resolve a stenotic, restenotic, or thrombotic condition in a blood vessel, usually an artery, such as a coronary artery. Usually, the corrective procedure will comprise balloon angioplasty. The corrective procedure may also comprise directional atherectomy, rotational atherectomy, laser angioplasty, stenting, or the like, where the lumen of the treated blood vessel is enlarged to at least partially alleviate a stenotic condition which existed prior to the treatment. The susceptible tissue site may include tissues associated with intracorporeal lumens, organs, or localized tumors. As used herein, the term "intracorporeal body" refers to body lumens or internal corporeal tissues and/or organs, within a corporeal body. The body lumen may be any blood vessel in the patient's vasculature, including veins, arteries, aorta, and particularly including coronary and peripheral arteries, as well as previously implanted grafts, shunts, fistulas, and the like. It will be appreciated that the present invention may also be applied to other body lumens, such as the biliary duct, which are subject to excessive neoplastic cell growth. Examples of internal corporeal tissues and organs, include various organs, nerves, glands, ducts, and the like. In an embodiment, the device includes luminal prostheses such as vascular stents or grafts. In another embodiment, the device may include, cardiac pacemaker leads or lead tips, cardiac defibrillator leads or lead tips, heart valves, sutures, or needles, pacemakers, orthopedic devices, appliances, implants or replacements, or portions of any of the above.

As used herein the term "therapeutic capable agent" includes at least one compound which is either therapeutic as it is introduced to the corporeal body (e.g., human subject) under treatment, or becomes therapeutic after entering the corporeal body of the subject (or exposed to the surface of the corporeal body as the case may be), by for example, reaction with a native or non-native substance or condition. Examples of native conditions include pH (e.g. acidity), chemicals, temperature, salinity, conductivity, contractile or expansive changes of the body lumen/organ, and pulsating nature of the body fluids as they flow through or come in contact with the device; with non-native conditions including those such as magnetic fields, and ultrasound. In the present application, the chemical name of any of the therapeutic capable agents or other compounds is used to refer to the compound itself and to pro-drugs (precursor substances that are converted into an active form of the compound in the body), and/or pharmaceutical derivatives, analogues, or metabolites thereof (bioactive compound to which the compound converts within the body directly or upon introduction of other agents or conditions (e.g., enzymatic, chemical, energy), or environment (e.g., pH)).

In an embodiment, the device comprises a structure and at least one source of at least one therapeutic capable agent associated with the structure. In one embodiment, the device further comprises a rate-controlling element disposed or formed adjacent at least a portion of the structure. The therapeutic capable agent is associated at least in part with either or both the structure and the rate-controlling element in a manner as to become available, immediately or after a delay period, to the susceptible tissue site upon introduction of the device to the corporeal body. As used herein the term "associated with" refers to any form of association such as directly or indirectly being coupled to, connected to, disposed on, disposed within, attached to, adhered to, bonded to, adjacent to, entrapped in, and like configurations.

In an embodiment, the device is implantable within a corporeal body including an intracorporeal target site (e.g., body organs or lumens). The intracorporeal target site may include the susceptible tissue site or in the alternative it may be a supply site such as an artery which supplies blood to the susceptible tissue site.

In one embodiment the structure may be an expandable structure. In another embodiment, the structure may have a substantially constant size or diameter, or alternatively depending on the application and use, may be a contractable structure. The expandable structure may be in the form of a stent, which additionally maintains luminal patency, or in the form of a graft, which additionally protects or enhances the strength of a luminal wall. The device, may comprise at least in part, a scaffold, preferably formed at least in part from an open lattice. Optionally, the scaffold comprises an at least substantially closed surface. The expandable structure may be radially expandable. The structure may be self-expanding or expandable by another object such as a balloon. In an embodiment, the structure includes at least one surface, usually, a tissue facing surface. In another embodiment, the structure includes a tissue facing surface, another surface usually a luminal surface, and two edge surfaces. In an embodiment, the structure may have an interior disposed between two surfaces, usually, the tissue facing and the luminal surfaces. In an embodiment, the structure includes portions having different mechanical stress or strain profiles upon expansion or contraction, or areas which are substantially in the direct line of fluid (e.g., blood or other bodily fluids) flow through the body. By way of example, the different portions of the structure may exhibit different stress characteristics during expansion of the device when implanted within the intracorporeal body. In one embodiment, the structure includes portions having relatively lower and portions having relatively higher mechanical stress or strain profiles with respect to one another. The term "having different mechanical profile" will herein be used to refer to this characteristic of the structure or prosthesis. In an embodiment, when the device may include an axially different coating profile such that the prosthesis comprises a different profile of the therapeutic capable agent and/or the rate-controlling element which will be in the direct flow of the body fluids thus subject to more turbulent flow.

The source may be disposed or formed adjacent at least a portion of the structure. The source may be disposed or formed adjacent at least a portion of either or both surfaces of the expandable structure, within the interior of the structure disposed between the two surfaces, adjacent either or both the edges, or any combination thereof. The association of the therapeutic capable agent with either or both the structure and the rate-controlling element may be continuous or in discrete segments. In one embodiment, the source is disposed or formed adjacent only a portion of the structure and/or the rate-controlling element, preferably, areas having lower mechanical stress profiles.

The expandable structure may be formed of any suitable material such as metals, polymers, or a combination thereof. In one embodiment, the expandable structure may be formed of an at least partially biodegradable material, selected from the group consisting of polymeric material, metallic materials, or combinations thereof. The at least partially biodegradable material, preferably degrades over time. Examples of polymeric material include poly-L-lactic acid, having a delayed degradation to allow for the recovery of the vessel before the structure is degraded. Example of metallic material include metals or alloys degradable in the corporeal body, such as stainless steel. An exemplary stent for use in the present invention is described in co-pending application Ser. No. 09/565,560, the full disclosure of which is incorporated herein by reference.

In an embodiment, the device is a stent generally including a cylindrical frame having proximal and distal ends, and tissue and luminal facing surfaces. The device usually further comprises a plurality of radially expansible unit segments including rings. The rings preferably have a serpentine shape. In an embodiment, the unit segments, preferably include segments having different mechanical profiles, as for example may be exhibit as a result of expansion. In an embodiment, some of the rings may be joined with at least one axially adjacent ring through expansion links. The links preferably have a sigmoidal shape, more preferably, an S shape having a relatively smooth profile along its length to minimize or reduce kinking upon expansion. Similarly, the links may comprise segments having different mechanical profiles along their length. For example, the joint and/or links may have relatively lower mechanical profile portions along their lengths with relatively higher mechanical profile portions at bends, points, intersections, joints, or areas exposed to flow turbulence. Preferably, the source is positioned adjacent the tissue facing surface of the structure. Preferably, the portion is an area of the structure having relatively lower mechanical profile.

In one embodiment, the source and/or the rate-controlling element are independently disposed only on a portion of the structure, preferably, the portion having relatively lower mechanical profile. In another embodiment, the source may be disposed on the relatively lower mechanical profile areas while the rate-controlling element is disposed over either the lower mechanical profile areas or the lower and higher mechanical profile areas.

The therapeutic capable agent may be associated with either or both the structure (e.g., expandable structure) and the rate-controlling element in one or more ways as described above. The therapeutic capable agent may be disposed adjacent (e.g., on or within) the expandable structure. Alternatively or additionally, the therapeutic capable agent may be disposed adjacent (e.g., on or within) the rate-controlling element, or in an interface between structure and the rate-controlling element, in a pattern that provides the desired performance (e.g., release rate). In another embodiment, the device includes an outer layer including the therapeutic capable agent. In an embodiment, the therapeutic capable agent outer layer provides for a bulous release of the therapeutic capable agent upon introduction of the device to the corporeal body. In one embodiment, the source may comprise a plurality of compounds, as for example the therapeutic capable agent and another compound such as another therapeutic capable agent or an enabling compound. Each of the plurality of compounds may be in the same or different area of the source.

The rate-controlling element may be formed of a non-degradable, partially degradable, substantially degradable material, or a combination thereof. The material may be synthetic or natural; non-polymeric, polymeric, ceramic, or metallic; or a combination thereof. The rate-controlling element may have a porous, microporous, nanoporous, or nonporous morphology, or any combinations thereof. Preferably, when the device comprise a porous rate-controlling element, at least one layer of a nonporous rate-controlling element is disposed between the source and the porous rate-controlling element.

In a preferred embodiment the rate-controlling element is formed from a nonporous material, usually a nonporous conformal material. Example of suitable non-porous material include, but not limited to: plasma deposited polymers; sputtered, evaporated, electroplated metals and/or alloys; glow discharge coating; polyethylene; polyurethanes; silicone rubber; cellulose; and parylene including parylene C, N, D, F, or combinations thereof, usually parylene C. In an embodiment, the device comprises a layer of another rate-controlling element which is configured to bind, at least partially, with the therapeutic capable agent. In an embodiment Bovine Serum Albumin (BSA) is disposed adjacent the nonporous rate-controlling element (e.g., parylene) such that as the therapeutic capable agent (e.g., mycophenolic acid) diffuses or elutes out of the nonporous rate-controlling element, the therapeutic capable agent binds with the BSA, further delaying or controlling the release of therapeutic capable agent. Other examples of another rate-controlling element capable of binding with the therapeutic capable agent include quarternary ammonium compounds such as polyethylene imine. In one embodiment a hydrogel compound is disposed under either or both the therapeutic capable agent and the rate-controlling element or in the matrix. As body fluids come in contact with the hydrogel compound, the hydrogel compound swells causing a change in the flow or diffusion properties of the therapeutic capable agent through the rate-controlling element, as for example by causing disruptions in the rate-controlling element layer.

As defined herein, "porous material" refers to a polymeric material or structure having an open cell structure. Such material can be classified as macroporous, microporous (e.g., having cell/pore size ranging from about 1 to about 100 microns), or nanoporous (e.g., having cell/pore size in nanometer range and larger than the actual length of the polymer chains making up the polymer). The typical chain length of such porous material ranges from about 2 to about 100 angstroms (A). As used herein, "nonporous material" refers to materials including coatings, which have no pores or have pore size less than the normal free volume of the material. The free volume is associated with the space between molecules in a material accessible to segmental motions. In an embodiment the rate-controlling element has a free volume equal or less than twice the volume of the rate-controlling element molecule.

At the molecular level most, if not all, of the solid and/or nonporous polymers have at least some free volume which allows for chain motion. The dimension of the free volume space is usually in the order of fractions of the molecular chain length, thus the term nonporous. As temperature increases so does the chain motion and the free volume.

In an embodiment, the rate of release of the therapeutic capable agent from the source through the rate-controlling element (as an external layer covering the source and/or as a matrix material), is affected by the "partition coefficient" and diffusivity of the therapeutic capable agent molecule and the thickness of the rate-controlling element.

The solubility of different therapeutic capable agents in the same nonporous polymeric rate-controlling element varies greatly. Therapeutic capable agent-polymeric rate-controlling element solubility depends on several factors including any one or more of the following: the difference in the chemical structure of the therapeutic capable agent and the nonporous polymeric rate-controlling element, the presence and characteristic of the functional groups of the therapeutic capable agent and the rate-controlling element, hydrogen, ionic, or other bonding between the two, molecular weight, stereochemical configurations of the therapeutic capable agent and the nonporous polymeric rate-controlling element, crystalline/amorphous state, temperature of the system, activity coefficient of the therapeutic capable agent solute in the polymeric rate-controlling element, the molar heat of fusion absorbed when the therapeutic capable agent crystals dissolve or solubilize into the polymeric rate-controlling element.

The diffusion of the therapeutic capable agent through the nonporous polymeric rate-controlling element depends on a number of factors such as the molecular energy (e.g., vibration, rotation, translation), and intermolecular attraction/repulsion (between the portion of the same material or that of between the two different material). The conformation of the polymer and the therapeutic capable agent and/or rate-controlling element depends on a variety of factors including the chain length, molecular structure, crystallinity, and degree of cross-linking.

In an embodiment, where the rate-controlling element is formed from a nonporous material, upon expansion of the structure within the intracorporeal body, the rate-controlling element may at least partially form areas of disruption on or within the rate-controlling element. The disruptions allow the transport of either or both the elution medium (e.g., bodily fluids such as blood, water, serum, tissue, interstitial fluid) to the source, or the therapeutic capable agent from the source to the targeted intracorporeal site. The transport of the body fluids to the source assists in the transport of the therapeutic capable agent back to the targeted intracorporeal site. In one embodiment, the disruptions may be formed in the implanted device, at least in portions of the device which are in the direct line of fluid flow.

By way of examples, a metallic material that at least partially degrades with time may be used as the rate-controlling element; as well as non-polymers having large molecular weight, polar or non-polar functional groups, electrical charge, steric hindrance groups, hydrophobic, hydrophilic, or amphiphilic moieties. It should be appreciated that the device may comprise a plurality of rate-controlling elements, each having same or different chemical and physical profiles and characteristics, each being present at similar or different locations, and including none, same, or different therapeutic capable agents. In another embodiment, the device may include areas (e.g., distal and proximal ends of the device) having variable thickness of both the source and the rate-controlling element to allow for slower or faster release.

Suitable nondegradable or slow degrading rate-controlling element materials include, but are not limited to, polyurethane, polyethylenes imine, cellulose acetate butyrate, ethylene vinyl alcohol copolymer, silicone, polytetrafluorethylene (PTFE), parylene, parylast, poly (methyl methacrylate butyrate), poly-N-butyl methacrylate, poly (methyl methacrylate), poly 2-hydroxy ethyl methacrylate, poly ethylene glycol methacrylates, poly vinyl chloride, poly(dimethyl siloxane), poly(tetrafluoroethylene), poly (ethylene oxide), poly ethylene vinyl acetate, poly carbonate, poly acrylamide gels, N-vinyl-2-pyrrolidone, maleic anhydride, Nylon, quarternary ammonium compounds including stearyl ammonium chloride and benzyl ammonium chloride, cellulose acetate butyrate (CAB) and the like, including other synthetic or natural polymeric substances; mixtures, copolymers, and combinations thereof. In an embodiment the rate-controlling element is formed from a material selected from the group consisting of silicone, polytetrafluoroethylene, parylast, polyurethane, parylene, cellulose acetate butyrate; mixtures, copolymers and combinations thereof.

Suitable biodegradable rate-controlling element materials include, but are not limited to, poly(lactic acid), poly (glycolic acid) and copolymers, poly dioxanone, poly (ethyl glutamate), poly (hydroxybutyrate), polyhydroxyvalerate and copolymers, polycaprolactone, polyanhydride, poly (ortho esters); poly (iminocarbonates), polyester amides, polyester amines, polycyanoacrylates, polyphosphazenes, copolymers and other aliphatic polyesters, or suitable copolymers thereof including copolymers of poly-L-lactic acid and poly-e-caprolactone; mixtures, copolymers, and combinations thereof. Other examples of suitable material include polymers, as disclosed in U.S. Pat. No. 5,610,241 and issued to Lee et al., and incorporated herein by reference in its entirety. Lee discloses graft polymers having a biodegradable backbone and side chains with reactive amino acid groups and/or protected amino acid groups. The graft polymers are obtained from a biodegradable homopolymer or copolymer starting material having carbonyl group and carbon alpha to carbon of the carbonyl group and having H atom on carbon alpha to carbonyl carbon and consisting essentially of biodegradable homopolymer or copolymer backbone joined at backbone carbon alpha to backbone carbonyl group, to the chain amino acid pendant group at a carbonyl moiety of the pendant group, which side chain amino acid pendant group contains reactive amino acid group(s) and/or protected amino acid groups.

The graft polymers are prepared by reacting amino acid halide having other reactive groups protected, with biodegradable polymer containing carbanion on carbon alpha to carbon of carbonyl group, and then deprotecting the protected groups.

Suitable natural material include: fibrin, albumin, collagen, gelatin, glycosoaminoglycans, oligosaccharides & poly saccharides, chondroitin, phosholipids, phosphorylcholine, glycolipids, proteins, amino acids, cellulose, and mixtures, copolymers, or combinations thereof. In an embodiment, the rate-controlling element comprises Bovine Serum Albumin (BSA).

Other suitable material include, titanium, chromium, Nitinol, gold, stainless steel, metal alloys, ceramics, or a combination thereof, and other compounds that may release the therapeutic capable agent as a result of interaction (e.g., chemical reaction, high molecular weight, steric hindrance, hyrophobicity, hydrophilicity, amphilicity, heat) of the therapeutic capable agent with the rate-controlling element material (e.g, a non-polymer compound). By way of example, a combination of two or more metals or metal alloys with different galvanic potentials to accelerate corrosion by galvanic corrosion pathways may also be used.

The degradable material may degrade by bulk degradation or hydrolysis. In an embodiment, the rate-controlling element degrades or hydrolyzes throughout, or preferably, by surface degradation or hydrolysis, in which a surface of the rate-controlling element degrades or hydrolyzes over time while maintaining bulk integrity. In another embodiment, hydrophobic rate-controlling elements are preferred as they tend to release therapeutic capable agent at desired release rate. A non-degradable rate-controlling element may release therapeutic capable agent by diffusion.

In an embodiment, the therapeutic capable agent itself is a rate-controlling element, as for example, when the therapeutic capable agent is a polymeric material. In an embodiment, the therapeutic capable agent, alone or in combination with a matrix material, forms a matrix. The term "matrix" as used herein refers to an association between the therapeutic capable agent and the rate-controlling element and/or other compounds. In an embodiment, the matrix comprises a matrix interface formed between the rate-controlling element and the therapeutic capable agent and/or other compound/s. In an embodiment, the rate-controlling element may comprise multiple adjacent layers formed from the same or different material. The therapeutic capable agent may be present adjacent one or more of the rate-controlling element layers. Additionally and/or alternatively, the therapeutic capable agent may form a matrix and/or matrix interface with one or more of the rate-controlling element layers.

The therapeutic capable agent may be selected from a group consisting of immunosuppressants, anti-inflammatories, anti-proliferatives, anti-migratory agents, anti-fibrotic agents, proapoptotics, calcium channel blockers, anti-neoplastics, anti-cancer agents, antibodies, anti-thrombotic agents, anti-platelet agents, IIb/IIIa agents, antiviral agents, and a combination thereof.

Specific examples of therapeutic capable agent include: mycophenolic acid, mycophenolate mofetil, mizoribine, methylprednisolone, dexamethasone, Certican™, rapamycin, Triptolide™, Methotrexate™, Benidipine™, Ascomycin™, Wortmannin™, LY294002, Camptothecin™, Topotecan™, hydroxyurea, Tacrolimus™ (FK 506), cyclophosphamide, cyclosporine, daclizumab, azathioprine, prednisone, Gemcitabine™, cilostazol (Pletal™), tranilast, quercetin, suramin; metabolites, derivatives, and combinations thereof.

In an embodiment, the source of the therapeutic capable agent is a polymeric material including therapeutic capable agent moieties as a structural subunit of the polymer. The therapeutic capable agent moieties are polymerized and associated to one another through suitable linkages (e.g. ethylenic) forming polymeric therapeutic capable agent. Once the polymeric therapeutic capable agent is brought into contact with tissue or fluid such as blood, the polymeric therapeutic capable agent subunits disassociate. Alternatively, the therapeutic capable agent may be released as the polymeric therapeutic capable agent degrades or hydrolyzes, preferably, through surface degradation or hydrolysis, making the therapeutic capable agent available to the susceptible tissue site, preferably over a period of time. Examples of methods and compounds for polymerizing therapeutic capable agents are described in WO 99/12990 Patent Application by Kathryn Uhrich, entitled "Polyanhydrides With Therapeutically Useful Degradation Products," and assigned to Rutgers University, the full disclosure of which is incorporated herein by reference. An example of a therapeutic capable agents and a suitable reaction ingredient unit includes, mycophenolic acid with adipic acid and/or salicylic acid in acid catalyzed esterification reaction; mycophenolic acid with aspirin and/or adipic acid in acid catalyzed esterification reaction, mycophenolic acid with other NSAIDS, and/or adipic acid in acid catalyzed esterification reaction. In an embodiment, the polymeric therapeutic capable agent may be associated with a polymeric and/or metallic backbone.

The devices of the present invention may be configured to release or make available the therapeutic capable agent at one or more phases, the one or more phases having similar or different performance (e.g., release) profiles. The therapeutic capable agent may be made available to the tissue at amounts which may be sustainable, intermittent, or continuous; in one or more phases and/or rates of delivery; effective to reduce any one or more of smooth muscle cell proliferation, inflammation, immune response, hypertension, or those complementing the activation of the same. Any one of the at least one therapeutic capable agents may perform one or more functions, including preventing or reducing proliferative/restenotic activity, reducing or inhibiting thrombus formation, reducing or inhibiting platelet activation, reducing or preventing vasospasm, or the like.

The release rate may be further controlled by the size, quantity, location, elasticity of the rate-controlling element (i.e., as the polymeric rate-controlling element stretches or relaxes during flexing of the device), and the hydrophobicity of the therapeutic capable agent. By way of example, a methyprednisolone (MP) therapeutic capable agent being more hydrophobic than mycophenolic acid (MPA) releases at a slower rate into the surrounding intracorporeal site or elusion medium than mycophenolic acid.

The total amount of therapeutic capable agent made available to the tissue depends in part on the level and amount of desired therapeutic result. The therapeutic capable agent may be made available at one or more phases, each phase having similar or different release rate and duration as the other phases. The release rate may be pre-defined. In an embodiment, the rate of release may provide a sustainable level of therapeutic capable agent to the susceptible tissue site. In another embodiment, the rate of release is substantially constant. The rate may decrease and/or increase over time, and it may optionally include a substantially non-release period. The release rate may comprise a plurality of rates. In an embodiment the plurality of release rates include at least two rates selected from the group consisting of substantially constant, decreasing, increasing, substantially non-releasing.

The total amount of therapeutic capable agent made available or released will typically be in an amount ranging from about 0.1 µg to about 10 g, generally from about 0.1 µg to about 10 mg, preferably from about 1 µg to about 10 mg, more preferably from about 1 µg to about 2 mg, from 10 µg to about 2 mg, or from about 50 µg to about 1 mg.

In an embodiment, the therapeutic capable agent may be released in a time period, as measured from the time of implanting of the device, ranging from about 1 day to about 200 days; from about 1 day to about 45 days; or from about 7 days to about 21 days.

In an embodiment the release rate of the therapeutic capable agent per day may range from about 0.001 micrograms (µg) to about 1000 µg, usually from about 0.001 µg to about 200 µg, normally from about 0.5 µg to about 200 µg, and typically from about 1 µg to about 60 µg.

In one embodiment, the rate-controlling element is configured to have properties, physical and/or chemical properties (e.g., physical dimensions such as thickness and chemical properties such as polymer chemical structure) such that the flux density of the therapeutic capable agent across the rate-controlling element (or through the matrix as the case may be) to the targeted tissue site ranges from about $1.71 \times 10^{-14}$ g/(cm$^2$s) to about $1.71 \times 10^{-8}$ g/(cm$^2$s), usually from about $1.71 \times 10^{-14}$ g/(cm$^2$s) to about $3.43 \times 10^{-9}$ g/(cm$^2$s), normally from about $8.57 \times 10^{-12}$ g/(cm$^2$s) to about $3.43 \times 10^{-9}$ g/(cm$^2$s), and typically from about $1.71 \times 10^{-11}$ g/(cm$^2$s) to about $1.03 \times 10^{-9}$ g/(cm$^2$s). The desired flux density is affected by the total interfacial area between the therapeutic capable agent and the rate-controlling element, the diffusion coefficient of the therapeutic capable agent across (or through the matrix) the rate-controlling element. Thus, depending on the nature of the drug and the desired therapeutic dosages (e.g., total flux (μg/day)) and the design of the device (e.g., total area of the device including therapeutic capable agent), the various properties (e.g., physical and/or chemical) may be configured to bring about the desired result.

The therapeutic capable agent may be made available at an initial phase and one or more subsequent phases. When the therapeutic capable agent is delivered at different phases, the initial delivery rate will typically be from about 0 to about 99% of the subsequent release rates, usually from about 0% to about 90%, preferably from about 0% to 75%. In an embodiment a mammalian tissue concentration of the substance at an initial phase will typically be within a range from about 0.001 nanogram (ng)/mg of tissue to about 100 μg/mg of tissue; from about 1 ng/mg of tissue to about 100 μg/mg tissue; from about 1 ng/mg of tissue to about 10 μg/mg of tissue. A mammialian tissue concentration of the substance at a subsequent phase will typically be within a range from about 0.00 1 ng/mg of tissue to about 600 μg/mg of tissue, preferably from about 1 ng/mg of tissue to about 10 μg/mg of tissue.

The rate of delivery during the initial phase will typically range from about 0.001 ng to about 50 μg per day, usually from about 0.1 μg to about 30 μg per day, more preferably, from about 1 μg per day to about 20 μg per day. The rate of delivery at the subsequent phase may range from about 0.01 μg per day to about 200 μg per day, usually from about 1 μg per day to about 100 μg per day. In one embodiment, the therapeutic capable agent is made available to the susceptible tissue site in a programmed and/or controlled manner with increased efficiency and/or efficacy. Moreover, the present invention provides limited or reduced hindrance to endothelialization of the vessel wall.

The duration of the initial, subsequent, and any other additional phases may vary. For example, the release of the therapeutic capable agent may be delayed from the initial implantation of the device. Typically the delay is sufficiently long to allow the generation of sufficient cellularization or endothelialization at the treated site. Typically, the duration of the initial phase will be sufficiently long to allow initial cellularization or endothelialization at, at least part of the device. Typically, the duration of the initial phase whether being a delayed phase or a release phase, is usually less than about 12 weeks, more usually from about 1 hour to about 8 weeks, more preferably from about 12 hours to about 4 weeks, from about 12 hours to about 2 weeks, from about 1 day to about 2 weeks, or from about 1 day to about 1 week.

The durations of the one or more subsequent phases may also vary, typically being from about 4 hours to about 24 weeks, from about 1 day to about 12 weeks, from about 2 days to about 8 weeks, more preferably in from about of 3 days to about 50 days. In an embodiment, the duration specified relates to a vascular environment. The more than one phase may include similar or different durations, amounts, and/or rates of release. For example, in one scenario, there may be an initial phase of delay, followed by a subsequent phase of release a first subsequent rate, and second subsequent phase at a second subsequent rate of release, and the like.

When the device includes the source including a plurality of compounds (e.g., first therapeutic capable agent and an another compound such as another therapeutic capable agent or enabling compound), the plurality of compounds may be released at different times and/or rates, from the same or different layers when present. Each of the plurality of compounds may be made available independently of another, simultaneous with, or subsequent to the interventional procedure, and may be simultaneous or sequential with one another. For example, a first therapeutic capable agent (e.g., Triptolide™) may be released within a time period of 1 day to 45 days with the second therapeutic capable agent (e.g, mycophenolic acid) released within a time period of 2 days to 3 months, from the time of interventional procedure.

Furthermore, a biocompatible (e.g., blood compatible) layer may be formed over the source and/or the most outer layer of the device, to make or enhance the biocompatibility of the device. Suitable biocompatible material for use as the biocompatible layer include, but are not limited to, polyethylene glycol (PEG), polyethylene oxide (PEO), hydrogels, silicone, polyurethanes, heparin coatings.

In an embodiment, the device further includes another compound, such as another therapeutic capable agent, or another compound enabling and/or enhancing either or both the release and efficacy of the therapeutic capable agent. The another therapeutic capable agent may be associated with expandable structure in the same or different manner as the first therapeutic capable agent.

The another therapeutic capable agent may act in synergy with the therapeutic capable agent, in ways such as compensating for the possible reactions and by-products that can be generated by the therapeutic capable agent. By way of example, the therapeutic capable agent may reduce generation of desired endothelial cells, thus by including a suitable another therapeutic capable agent, more endothelialization may be achieved.

The another therapeutic capable agent may comprise at least one compound selected from the group consisting of anti-cancer agents; chemotherapeutic agents; thrombolytics; vasodilators; antimicrobials or antibiotics antimitotics; growth factor antagonists; free radical scavengers; biologic agents; radiotherapeutic agents; radiopaque agents; radiolabelled agents; anti-coagulants such as heparin and its derivatives; anti-angiogenesis therapeutic capable agents such as Thalidomide™; angiogenesis therapeutic capable agents; PDGF-B and/or EGF inhibitors; anti-inflamatories including psoriasis therapeutic capable agents; riboflavin; tiazofurin; zafurin; anti-platelet agents including cyclooxygenase inhibitors such as acetylsalicylic acid, ADP inhibitors such as clopidogrel (e.g., Plavix™) and ticlopdipine (e.g., Ticlid™), phosphodiesterase III inhibitors such as cilostazol (e.g., Pletal™), glycoprotein IIb/IIIa agents such as abciximab (e.g., Rheopro™); eptifibatide (e.g., integrilin™), and adenosine reuptake inhibitors such as dipyridmoles; healing and/or promoting agents including anti-oxidants, nitrogen oxide donors; antiemetics; antinauseants; derivatives and combinations thereof. The another therapeutic agent may be released prior to, concurrent with, or subsequent to, the therapeutic capable agent, at similar or different rates and phases.

In an embodiment, the another compound comprises, an enabling compound respondable to an external form of energy, or native condition, to affect the release of the therapeutic capable agent. The respondable compound may be associated with the therapeutic capable agent, the rate-controlling element, the expandable structure, or a combination thereof. The second enabling compound may be formed from magnetic particles coupled to the therapeutic capable agent. The energy source may be a magnetic source for directing a magnetic field at the prosthesis after implantation to effect release of the therapeutic capable agent.

In an embodiment of a method for making the devices of the present invention, an implantable structure is provided with a source of therapeutic capable agent. The therapeutic capable agent-coated structure is then heated to a temperature, usually to a temperature about the same as the melting point of the therapeutic capable agent or less, for a period of time. Lower or higher temperatures may also be used depending on the duration of the heating step. In an embodiment, the heating helps in a change in the crystallinity of the therapeutic capable agent, thus providing for a more uniform surface under the rate-controlling element. In an alternate embodiment, the therapeutic capable agent-coated structure is heated after the rate-controlling element has also be provided on the structure.

In another embodiment, the therapeutic capable agent/rate-controlling element-coated structure is heated to a temperature about the same or lower than the glass transition temperature (Tg) of the rate-controlling element. Higher or lower temperatures may also be used with appropriate adjustment of the duration of the heating step. In one embodiment, the heating is performed under vacuum and/or in the absence of oxygen. The heating of the coated device to this temperature, assists in reducing the residual stress of the device, thus reducing the likelihood of formation of undesirable disruption in the rate-controlling element coating. It should be noted, that in some embodiments, the presence of disruptions before and/or after the device is implanted in the intracorporeal body may be purposefully designed into the device. Other forms of energy other than heat, may also be used in the reduction of the residual stress, for example, ultrasound, or vibrational energy.

The present invention still further provides intracorporeal devices comprising an implantable scaffold having at least one source of at least one therapeutic capable agent associated therewith and configured to be released when the scaffold is implanted. A rate-controlling element comprising a non-porous material covers at least a portion of the source. Preferably, the non-porous material comprises parylene, more preferably consisting essentially of paralyne, and often consisting of parylene. Other non-porous materials, however, may also find use, such as plasma deposited polymers, sputtered materials, evaporated materials, electroplated metals, electroplated alloys, glow discharge coating, polyethylenes, polyurethanes, silicone rubber, cellulose, and the like. Usually, the non-porous layers will become at least partially porous when exposed to the conditions in the implanted region, typically a blood vessel. Alternatively, the rate controlling member may become disrupted, e.g., crack or form holes, when implanted. Often, a therapeutic capable agent will be present in the rate-controlling element, usually being the same substance as in the source.

DETAILED DESCRIPTION OF THE INVENTION

Figure 1A:
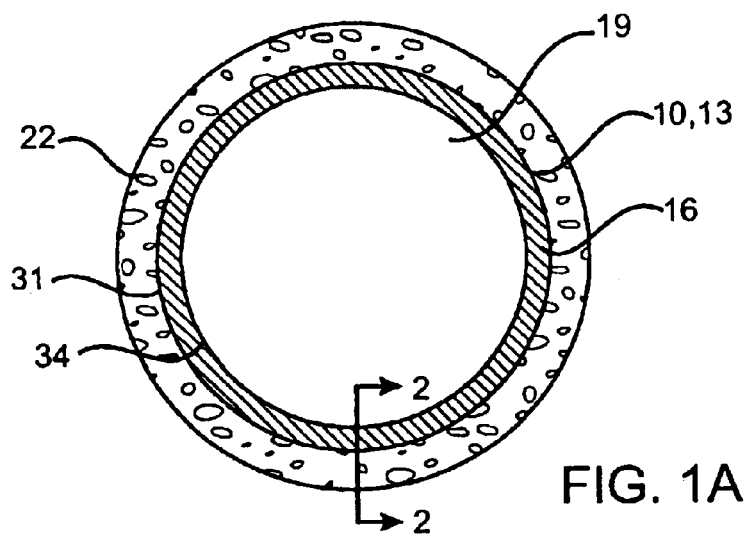
FIGS. 1A through 1C are cross-sectional views of a device embodying features of the present invention and implanted in a body lumen.
Figure 1B:
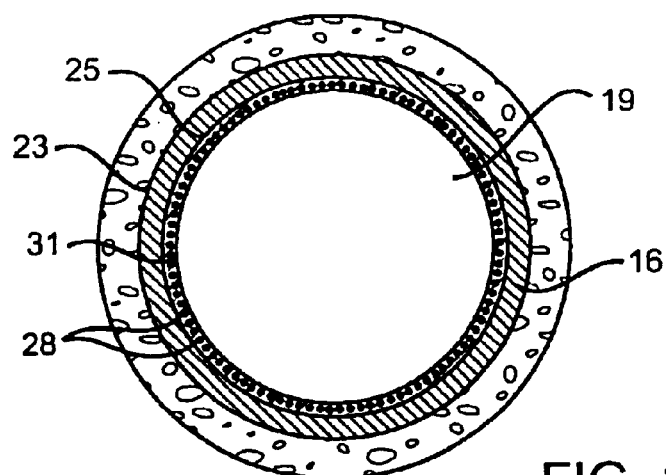
Figure 1C:
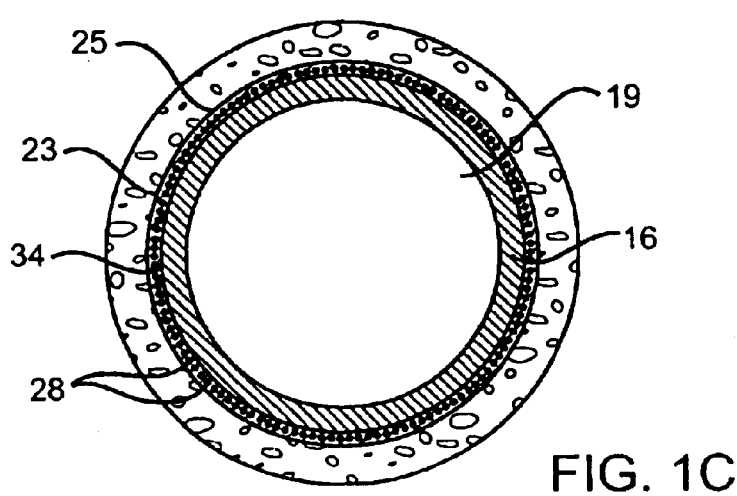
Figure 2A:
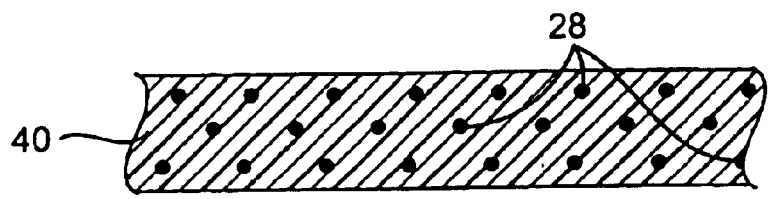
FIGS. 2A through 2N are cross-sectional views of various embodiments of the delivery prosthesis of FIGS. 1A–1C taken along line 2—2.
Figure 2B:
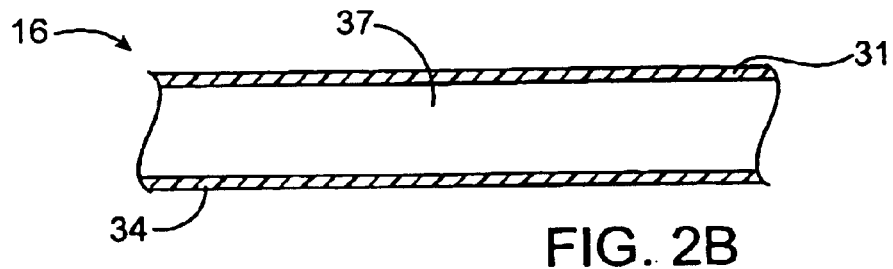
Figure 2C:
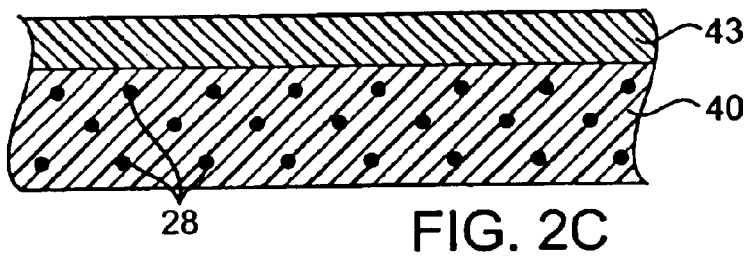
Figure 2D:
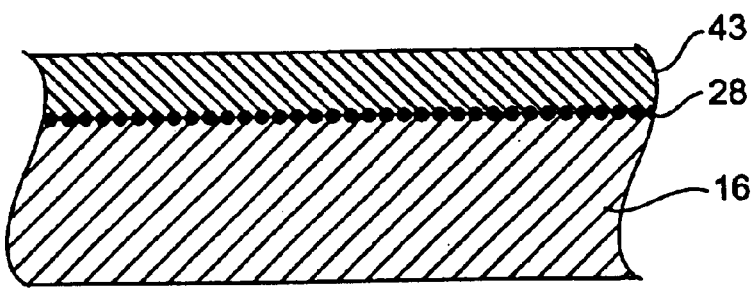
Figure 2E:
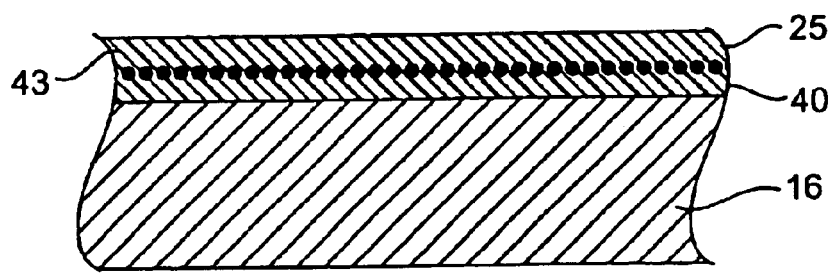
Figure 2F:
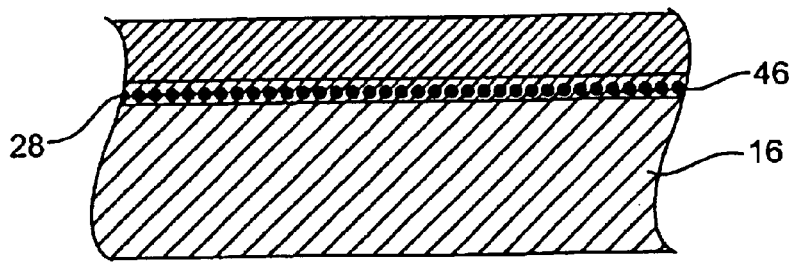
Figure 2G:
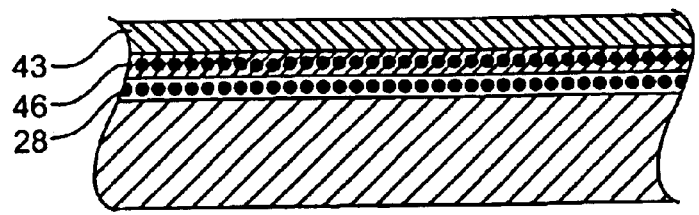
Figure 2H:
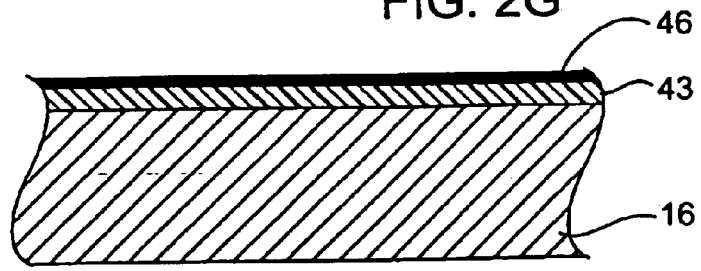
Figure 2I:
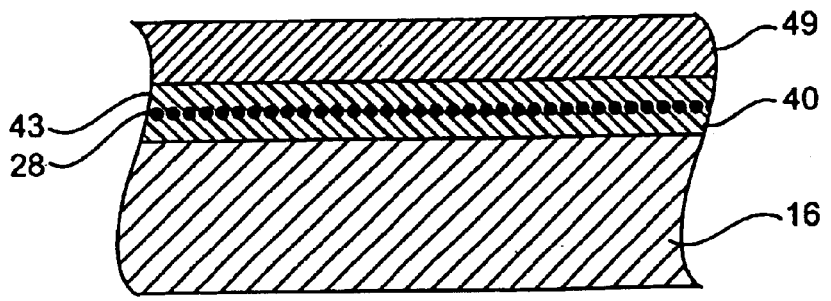
Figure 2J:
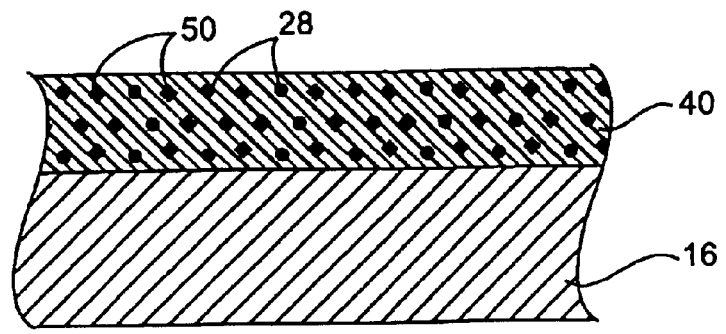
Figure 2K:
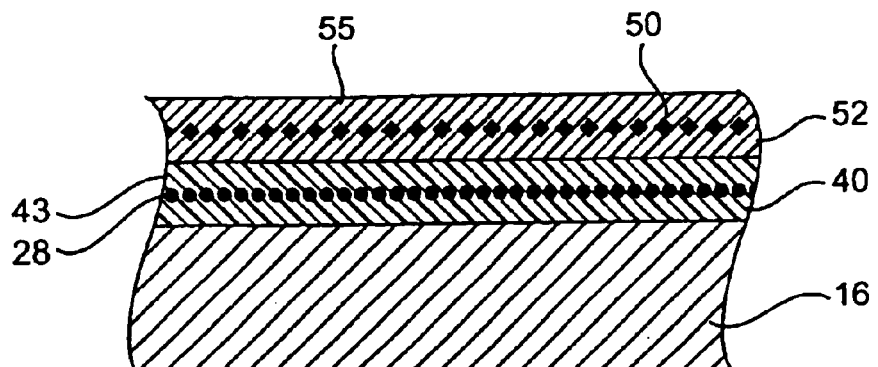
Figure 2L:
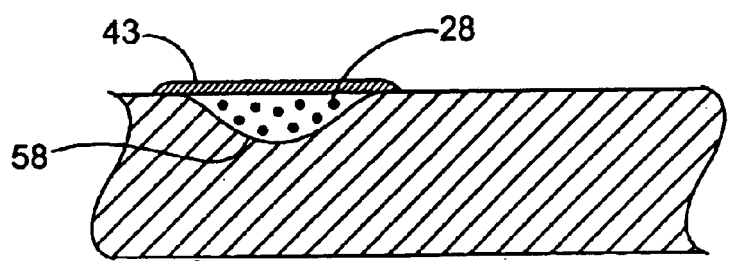
Figure 2M:
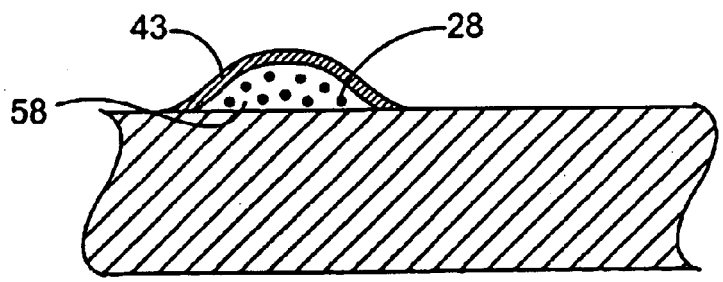
Figure 2N:
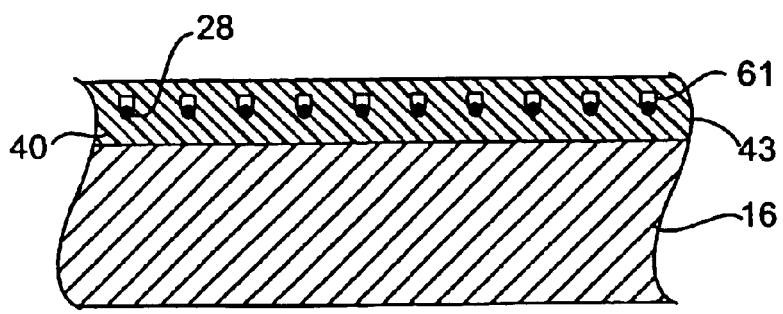

FIGS. 1A–1C, and cross-sectional drawings FIGS. 2A–2N, illustrate a device 10, such as a prosthesis 13, embodying features of the invention and generally including an expandable structure 16 implantable in an intracorporeal body, such as body lumen 19 including a susceptible tissue site 22, and a source 25 adjacent the expandable structure 16 including a therapeutic capable agent 28. The device 10, as shown, is disposed in the body lumen 19. It should be appreciated, that although the source 25 as depicted in the figures is disposed adjacent a surface of the expandable structure, the word adjacent is not intended to be limited by the exemplary figures or descriptions.

As used herein the term "therapeutic capable agent" includes at least one compound which is either therapeutic as it is introduced to the corporeal body (e.g., human subject) under treatment, or becomes therapeutic after entering the corporeal body of the subject (or exposed to the surface of the corporeal body as the case may be), by for example, reaction with a native or non-native substance or condition. Examples of native conditions include pH (e.g. acidity), chemicals, temperature, salinity, conductivity, contractile or expansive changes of the body lumen/organ, and pulsating nature of the body fluids as they flow through or come in contact with the device; with non-native conditions including those such as magnetic fields, and ultrasound. In the present application, the chemical name of any of the therapeutic capable agents or other compounds is used to refer to the compound itself and to pro-drugs (precursor substances that are converted into an active form of the compound in the body), and/or pharmaceutical derivatives, analogues, or metabolites thereof (bioactive compound to which the compound converts within the body directly or upon introduction of other agents or conditions (e.g., enzymatic, chemical, energy), or environment (e.g., pH)).

The expandable structure may be formed of any suitable material such as metals, polymers, or a combination thereof. In one embodiment, the expandable structure may be formed of an at least partially biodegradable material, selected from the group consisting of polymeric material, metallic materials, or combinations thereof. The at least partially biodegradable material, preferably degrades over time. Examples of polymeric material include poly-L-lactic acid, having a delayed degradation to allow for the recovery of the vessel before the structure is degraded. Example of metallic material include metals or alloys degradable in the corporeal body, such as stainless steel.

The therapeutic capable agent may be selected from a group consisting of immunosuppressants, anti-inflammatories, anti-proliferatives, anti-migratory agents, anti-fibrotic agents, proapoptotics, calcium channel blockers, anti-neoplastics, anti-cancer agents, antibodies, anti-thrombotic agents, anti-platelet agents, IIb/IIIa agents, antiviral agents, and a combination thereof.

Specific examples of therapeutic capable agent include: mycophenolic acid, mycophenolate mofetil, mizoribine, methylprednisolone, dexamethasone, Certican™, rapamycin, Triptolide™, Methotrexate™, Benidipine™, Ascomycin™, Wortmannin™, LY294002, Camptothecin™, Topotecan™, hydroxyurea, Tacrolimus™ (FK 506), cyclophosphamide, cyclosporine, daclizumab, azathioprine, prednisone, Gemcitabine™, cilostazol (Pletal™), tranilast, quercetin, suramin; metabolites, derivatives, and combinations thereof.

In an embodiment, the source of the therapeutic capable agent is a polymeric material including therapeutic capable agent moieties as a structural subunit of the polymer. The therapeutic capable agent moieties are polymerized and associated to one another through suitable linkages (e.g. ethylenic) forming polymeric therapeutic capable agent. Once the polymeric therapeutic capable agent is brought into contact with tissue or fluid such as blood, the polymeric therapeutic capable agent subunits disassociate. Alternatively, the therapeutic capable agent may be released as the polymeric therapeutic capable agent degrades or hydrolyzes, preferably, through surface degradation or hydrolysis, making the therapeutic capable agent available to the susceptible tissue site, preferably over a period of time. Examples of methods and compounds for polymerizing therapeutic capable agents are described in WO 99/12990 Patent Application by Kathryn Uhrich, entitled "Polyanhydrides With Therapeutically Useful Degradation Products," and assigned to Rutgers University, the full disclosure of which is incorporated herein by reference. An example of a therapeutic capable agents and a suitable reaction ingredient unit includes, mycophenolic acid with adipic acid and/or salicylic acid in acid catalyzed esterification reaction; mycophenolic acid with aspirin and/or adipic acid in acid catalyzed esterification reaction, mycophenolic acid with other NSAIDS, and/or adipic acid in acid catalyzed esterification reaction. In an embodiment, the polymeric therapeutic capable agent may be associated with a polymeric and/or metallic backbone.

The expandable structure 16, as shown without intending any limitation, has a tissue facing surface 31 and luminal facing surface 34, and optionally an interior 37 which may include a lumen as shown in FIG. 2B. It will be appreciated that the following depictions are for illustration purposes only and do not necessarily reflect the actual shape, size, configuration, or distribution of the prosthesis 13. The prosthesis may have a continuous structure or an intermittent structure as the case may be with many stents (e.g., the cross section of the stent does not entirely include a substrate forming the expandable structure—for example, some stents have a screen or mesh like cross section). The source may be disposed or formed adjacent at least a portion of either or both the luminal facing surface, as shown in FIG. 1B; and the tissue facing surface, as shown in FIG. 1C; within the interior of the expandable structure, or any combination thereof.

The source 25 for making the therapeutic capable agent available to therapeutic capable agent is associated with expandable structure, in one or more configurations. The source as shown in FIGS. 2A and 2B is within the expandable structure 16, as for example, when a matrix 40 is formed by the expandable structure 16 and the therapeutic capable agent 28, or when the therapeutic capable agent 28 is disposed within the interior (or the exterior of the expandable structure 16 as the case may be), 37 of the expandable structure 16. In an embodiment, the source 25 has a thickness typically in a range from about 1 angstroms (A) to about 50 microns ($\mu$m), from about 100 angstroms to about 20 microns, usually from about 100 angstroms to about 10 microns, normally from about 5000 angstroms to about 5 microns, and nominally from abut 7500 angstroms to about 2 microns.

Now referring to FIG. 2C, the device further comprises a rate-controlling element 43. The rate-controlling element may be formed over at least a portion of the expandable structure 16 for controlling the release of the therapeutic capable agent 28 from the matrix 40 or the interior 37 of the expandable structure. The source may be the rate-controlling element itself when the therapeutic capable agent is a polymeric therapeutic capable agent.

In an embodiment, the source may comprise a matrix comprising the therapeutic capable agent and a matrix forming material. By way of example, the source may comprise a matrix comprising mycophenolic acid and albumin (e.g., Bovine Serum Albumin or BSA). The presence of the matrix material for which the therapeutic capable agent has an affinity for, as for example BSA, reduces the rate of elusion (thus release) of mycophenolic acid to the susceptible tissue site.

The rate-controlling element may be formed of a non-degradable, partially degradable, substantially degradable material, or a combination thereof. The material may be synthetic or natural; non-polymeric, polymeric, ceramic, or metallic; or a combination thereof. The rate-controlling element may have a porous, microporous, nanoporous, or nonporous morphology, or any combinations thereof. Preferably, when the device comprise a porous rate-controlling element, at least one layer of a nonporous rate-controlling element is disposed between the source and the porous rate-controlling element.

In a preferred embodiment the rate-controlling element is formed from a nonporous material, usually a nonporous conformal material. Example of suitable non-porous material include, but not limited to: plasma deposited polymers; sputtered, evaporated, electroplated metals and/or alloys; glow discharge coating; polyethylene; polyurethanes; silicone rubber; cellulose; and parylene including parylene C, N, D, F, or combinations thereof, usually parylene C.

Suitable nondegradable or slow degrading rate-controlling element materials include, but are not limited to, polyurethane, polyethylenes imine, cellulose acetate butyrate, ethylene vinyl alcohol copolymer, silicone, polytetrafluoroethylene (PTFE), parylene, parylast, poly (methyl methacrylate butyrate), poly-N-butyl methacrylate, poly (methyl methacrylate), poly 2-hydroxy ethyl methacrylate, poly ethylene glycol methacrylates, poly vinyl chloride, poly(dimethyl siloxane), poly(tetrafluoroethylene), poly (ethylene oxide), poly ethylene vinyl acetate, poly carbonate, poly acrylamide gels, N-vinyl-2-pyrrolidone, maleic anhydride, Nylon, quarternary ammonium compounds including stearyl ammonium chloride and benzyl ammonium chloride, cellulose acetate butyrate (CAB) and the like, including other synthetic or natural polymeric substances; mixtures, copolymers, and combinations thereof. In an embodiment the rate-controlling element is formed from a material selected from the group consisting of silicone, polytetrafluoroethylene, parylast, polyurethane, parylene, cellulose acetate butyrate; mixtures, copolymers and combinations thereof.

Suitable biodegradable rate-controlling element materials include, but are not limited to, poly(lactic acid), poly (glycolic acid) and copolymers, poly dioxanone, poly (ethyl glutamate), poly (hydroxybutyrate), polyhydroxyvalerate and copolymers, polycaprolactone, polyanhydride, poly (ortho esters); poly (iminocarbonates), polyester amides, polyester amines, polycyanoacrylates, polyphosphazenes, copolymers and other aliphatic polyesters, or suitable copolymers thereof including copolymers of poly-L-lactic acid and poly-e-caprolactone; mixtures, copolymers, and combinations thereof. Other examples of suitable material include polymers, as disclosed in U.S. Pat. No. 5,610,241 and issued to Lee et al., and incorporated herein by reference in its entirety. Lee discloses graft polymers having a biodegradable backbone and side chains with reactive amino acid groups and/or protected amino acid groups. The graft polymers are obtained from a biodegradable homopolymer or copolymer starting material having carbonyl group and carbon alpha to carbon of the carbonyl group and having H atom on carbon alpha to carbonyl carbon and consisting essentially of biodegradable homopolymer or copolymer backbone joined at backbone carbon alpha to backbone carbonyl group, to the chain amino acid pendant group at a carbonyl moiety of the pendant group, which side chain amino acid pendant group contains reactive amino acid group(s) and/or protected amino acid groups.

The graft polymers are prepared by reacting amino acid halide having reactive groups protected, with biodegradable polymer containing carbanion on carbon alpha to carbon of carbonyl group, and then deprotecting the protected groups.

Suitable natural material include: fibrin, albumin, collagen, gelatin, glycosoaminoglycans, oligosaccharides & poly saccharides, chondroitin, phospholipids, phosphorylcholine, glycolipids, proteins, amino acids, cellulose, and mixtures, copolymers, or combinations thereof. In an embodiment, the rate-controlling element comprises Bovine Serum Albumin (BSA).

Other suitable material include, titanium, chromium, Nitinol, gold, stainless steel, metal alloys, ceramics, or a combination thereof; and other compounds that may release the therapeutic capable agent as a result of interaction (e.g., chemical reaction, high molecular weight, steric hindrance, hyrophobicity, hydrophilicity, amphilicity, heat) of the therapeutic capable agent with the rate-controlling element material (e.g, a non-polymer compound). By way of example, a combination of two or more metals or metal alloys with different galvanic potentials to accelerate corrosion by galvanic corrosion pathways may also be used.

The degradable material may degrade by bulk degradation or hydrolysis. In an embodiment, the rate-controlling element degrades or hydrolyzes throughout, or preferably, by surface degradation or hydrolysis, in which a surface of the rate-controlling element degrades or hydrolyzes over time while maintaining bulk integrity. In another embodiment, hydrophobic rate-controlling elements are preferred as they tend to release therapeutic capable agent at desired release rate. A non-degradable rate-controlling element may release therapeutic capable agent by diffusion.

FIG. 2D illustrates features of an embodiment having the therapeutic capable agent 28 disposed between one of the tissue or luminal facing surfaces of the expandable structure and the rate-controlling element 43.

As shown in FIG. 2E, the source 25 includes the rate-controlling element 43 formed adjacent at least a portion of one of the tissue or luminal facing surfaces of the expandable structure 16 and forming the matrix 40 with the therapeutic capable agent 28. As noted earlier, the therapeutic capable agent 28 may itself act as a rate-controlling element, as for example, when the polymeric therapeutic capable agent forms a matrix.

The matrix may be formed between the rate-controlling element 43 and the expandable structure 16 and forming a matrix interface 46 therebetween and/or between the therapeutic capable agent 28 and the rate-controlling element 43, as shown in FIGS. 2F and 2G. The matrix interface may formed as a result of the physical disposition of the two layers (e.g., rate-controlling element and the therapeutic capable agent. Alternatively and/or additionally, the matrix interface may be formed as a result of chemical reaction between the therapeutic capable agent and a polymer, oligomer, coupling agent, or small molecule. The matrix interface, preferably, further provides controlling of the release of the therapeutic capable agent to the susceptible tissue site.

In an embodiment, features of which are shown in FIG. 2H, the outer most layer of the prosthesis 13 may be formed of the therapeutic capable agent with or without a matrix interface 46 formed between the outer most layer and the other layers. It should be noted, that the therapeutic capable agent 28, although as shown in most figures as discrete particles, may form a smooth layer or a layer of particles, as for example as part of matrix interface 46 as shown in FIG. 2H.

In an alternate embodiment, features of which are shown in FIG. 2I, at least one layer of a second rate-controlling element 49 is formed over the matrix 40, further affecting the release rate of the therapeutic capable agent 28 to the susceptible tissue site. The second rate-controlling element 49 may be of the same or different material than that forming the first rate-controlling element 43.

Now referring now to FIGS. 2J and 2K, the source may comprise, a plurality of compounds, as for example the first therapeutic capable agent 28 and another compound 50 such as another therapeutic capable agent 50 or an enabling compound 61 (FIG. 2N). Each of the plurality of compounds may be in the same or different area of the source. For example, as shown in FIG. 2K, the first therapeutic capable agent 28 may be present in matrix 40 while the second therapeutic capable agent 50 is in a second matrix 52 formed by the second therapeutic capable agent 50 and a second rate-controlling element 55. The rate-controlling elements 43 and 55 may be formed from the same or different material.

The another therapeutic capable agent may comprise at least one compound selected from the group consisting of anti-cancer agents; chemotherapeutic agents; thrombolytics; vasodilators; antimicrobials or antibiotics antimitotics; growth factor antagonists; free radical scavengers; biologic agents; radiotherapeutic agents; radiopaque agents; radiolabelled agents; anti-coagulants such as heparin and its derivatives; anti-angiogenesis therapeutic capable agents such as Thalidomide™; angiogenesis therapeutic capable agents; PDGF-B and/or EGF inhibitors; anti-inflamatories including psoriasis therapeutic capable agents; riboflavin; tiazofurin; zafurin; anti-platelet agents including cyclooxygenase inhibitors such as acetylsalicylic acid, ADP inhibitors such as clopidogrel (e.g., Plavix™) and ticlopdipine (e.g., Ticlid™), phosphodiesterase III inhibitors such as cilostazol (e.g., Pletal™), glycoprotein IIb/IIIa agents such as abciximab (e.g., Rheopro™); eptifibatide (e.g., Integrilin™), and adenosine reuptake inhibitors such as dipyridmoles; healing and/or promoting agents including anti-oxidants, nitrogen oxide donors; antiemetics; antinauseants; derivatives and combinations thereof. The another therapeutic agent may be released prior to, concurrent with, or subsequent to, the therapeutic capable agent, at similar or different rates and phases.

In another embodiment, features of which are shown in FIGS. 2L and 2M, the therapeutic capable agent 28 is disposed within or on the expandable structure 16 within a reservoir 58. The rate-controlling element 43 may be disposed adjacent the reservoir 58 and/or the therapeutic capable agent 28 for affecting the release of the therapeutic capable agent. As stated earlier, the exemplary figures and descriptions are not meant to limit the term "adjacent."

In a further embodiment, features of which are shown in FIG. 2N, the another compound comprises the enabling compound 61 respondable to an external form of energy, or native condition, to affect the release of the therapeutic capable agent. The respondable compound may be associated with the therapeutic capable agent, the rate-controlling element, the expandable structure, or a combination thereof. As shown in FIG. 2N, the respondable compound is associated with the therapeutic capable agent. The enabling compound 61 may be formed from magnetic particles coupled to the therapeutic capable agent 28. The energy source may be a magnetic source for directing a magnetic field at the prosthesis 13 after implantation to effect release of the therapeutic capable agent 28. The magnetic particles 61 may be formed from magnetic beads and will typically have a size in a range from about 1 nm to about 100 nm. The magnetic source exposes the prosthesis 13 to its magnetic field at an intensity typically in the range from about 0.01 T to about 2 T, which will activate the magnetic particles 61 and thereby effect release of the therapeutic capable agent from the prosthesis. The another enabling compound may be present in other configurations of prosthesis 13 as described above.

Other suitable external energy sources, which may or may not require another compound or their performance may not be affected by the presence or absence of another compound, include ultrasound, magnetic resonance imaging, magnetic field, radio frequency, temperature change, electromagnetic, x-ray, radiation, heat, gamma, vibration, microwave, or a combination thereof.

By way of example, an ultrasound external energy source may be used having a frequency in a range from 20 kHz to 100 MHz, preferably in a range from 0.1 MHz to 20 MHz, and an intensity level in a range from 0.05 W/cm2 to 10 W/cm2, preferably in a range from 0.5 W/cm2 to 5 W/cm2. The ultrasound energy would be directed at the prosthesis 13 from a distance in a range from 1 mm to 30 cm, preferably in a range from 1 cm to 20 cm. The ultrasound may be continuously applied or pulsed, for a time period in a range from 5 sec to 30 minutes, preferably in a range from 1 minute to 15 minutes. The temperature of the prosthesis 13 during this period will be in a range from 36° C. to 48° C. The ultrasound may be used to increase a porosity of the prosthesis 13, thereby allowing release of the therapeutic capable agent 28 from the prosthesis 13. Other sources of energy, for example, heat or vibrational, may also be used to increase the porosity of the prosthesis or a portion thereof, or alter the configuration of the same.

Furthermore, a biocompatible (e.g., blood compatible) layer may be formed over the source and/or the most outer layer of the device, to make or enhance the biocompatibility of the device. Suitable biocompatible material for use as the biocompatible layer include, but are not limited to, polyethylene glycol (PEG), polyethylene oxide (PEO), hydrogels, silicone, polyurethanes, heparin coatings.

The dimensions of the expandable structure will depend on its intended use. Typically, the expandable structure will have a length in a range from about 5 mm to about 100 mm, usually being from about 8 mm to about 50 mm, for vascular applications. The diameter of a cylindrically shaped expandable structure for vascular applications, in a non-expanded configuration, usually ranges from about 0.5 mm to about 10 mm, more usually from about 0.8 mm to about 8 mm; with the diameter in an expanded configuration ranging from about 1.0 mm to about 100 mm, preferably from about 2.0 mm to about 30 mm. The expandable structure usually will have a thickness in a range from about 0.025 mm to 2.0 mm, preferably from about 0.05 mm to about 0.5 mm.

The ring segments, and other components of structures such as the expandable structure 16, may be formed from conventional materials used for body lumen stents and grafts, typically being formed from malleable metals or alloyes, such as 300 series stainless steel, or from resilient metals, such as superelastic and shape memory alloys, e.g., Nitinol™ alloys, spring stainless steels, and the like; non-metallic materials, such as ceramics or polymeric materials, or a combination thereof. The polymeric materials may include those polymeric materials that are substantially non-degradable, such as those described in relation to the materials of choice for the rate-controlling element. Alternatively, the polymeric material may be a biodegradable or substantially biodegradable polymer such as those described in reference with the biodegradable rate-controlling element material. When the expandable structure material is formed of the rate-controlling element material, the expandable structure may function both as the prosthesis and the direct source of the therapeutic capable agent. Additional structures for the body or unit segments of the present invention are illustrated in U.S. Pat. Nos. 5,195,417; 5,102,417; and 4,776,337, the full disclosures of which are incorporated herein by reference.

Other suitable material for use as the structure include, carbon or carbon fiber, cellulose acetate, cellulose nitrate, silicone, polyethylene terphthalate, polyurethane, polyamide, polyester, polyorthoester, polyanhydride, polyether sulfone, polycarbonate, polytetrafluoroethylene, or another biocompatible polymeric materials, or mixtures or copolymers thereof, a polyanhydride, polycaprolactone, polyhydroxybutyrate valerate or another biodegradable polymer, or mixtures or copolymers thereof; a protein, an extracellular matrix component, collagen, fibrin or another biologic agent, or a suitable mixture of any of the material listed above, degradable, non-degradable, metallic, or otherwise. In an embodiment, device may comprise a biodegradable structure with a polymeric source, such as a polymeric therapeutic capable agent.

Figure 3:
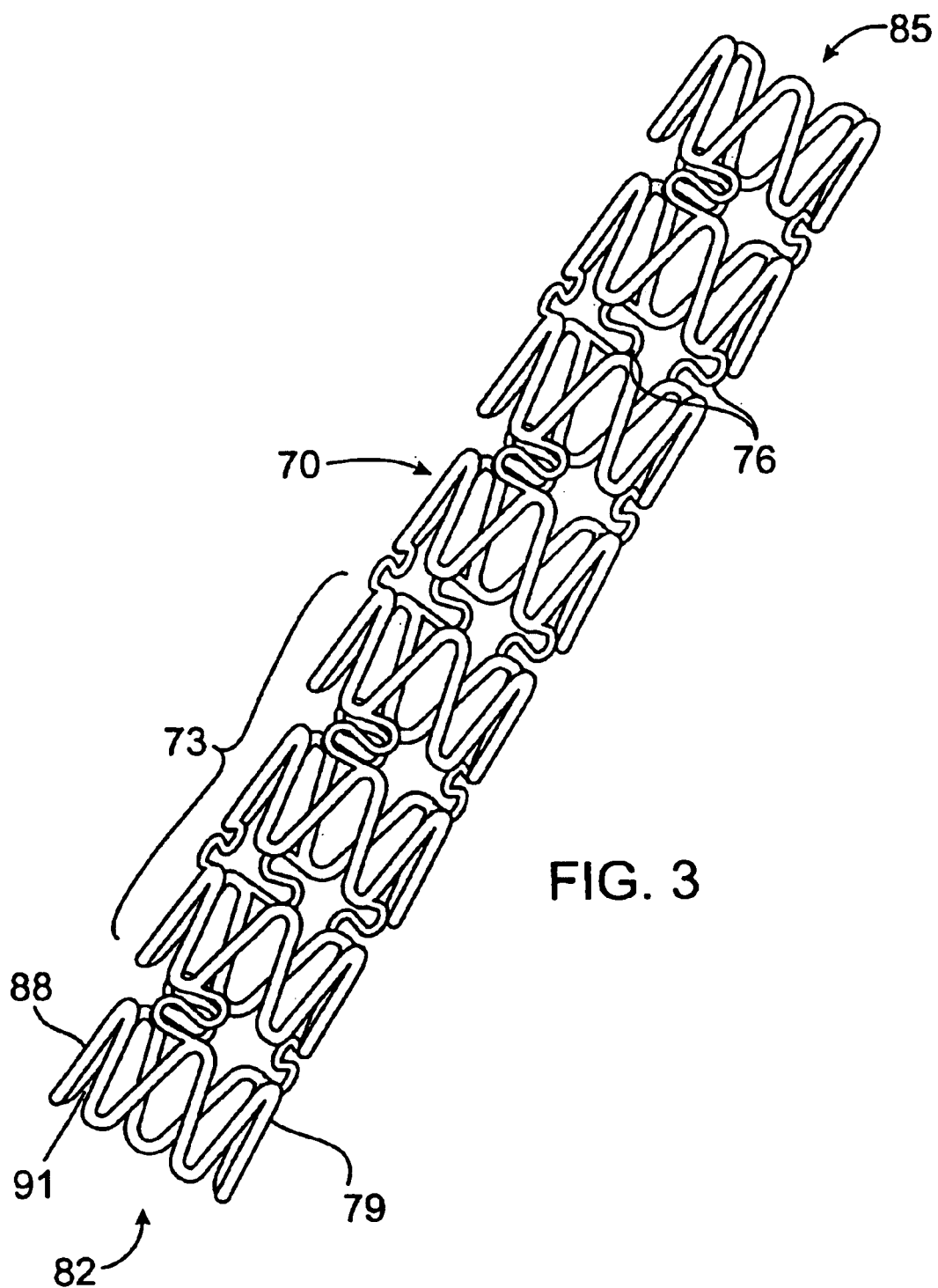
FIG. 3 is a schematic representation of an exemplary stent for use as the device of the present invention.

The expandable structure 16 may be a stent 70 or, a graft. When the expandable structure is a stent, the expandable structure 16 will usually comprise at least two radially expandable, usually cylindrical, ring segments 73 as shown in FIG. 3. Typically, the expandable structure 16 will have at least four, and often five, six, seven, eight, ten, or more ring segments. At least some of the ring segments will be adjacent to each other but others may be separated by other non-ring structures. The description of exemplary stent structures are not intended to be exhaustive, and it should be appreciate that other variations of stent designs usable in the present invention are known to those skilled in the art.

Referring back to FIG. 3, the exemplary stent 70 (embodying features of a stent described in more detail in co-pending U.S. patent application Ser. No. 08/968,319 and assigned to the assignee of the present invention, the disclosure of which in its entirety is incorporated herein by reference) for use in the present invention comprises from 4 to 50 ring segments 73 (with eight being illustrated). Each ring segment 73 is joined to the adjacent ring segment by at least one of sigmoidal links 76. Each ring segment 73 includes a plurality, e.g., six strut/hinge units, and two out of each six hinge/strut structures on each ring segment 73 will be joined by the sigmoidal links 76 to the adjacent ring segment. Stent 70 as shown in FIG. 3 shows the stent 70 is in a collapsed or non-expanded configuration.

The term "radially expandable" as used herein includes segments that can be converted from a small diameter configuration to a radially expanded, usually cylindrical, configuration which is achieved when the expandable structure 16 is implanted at a desired target site. The expandable structure 16 may be minimally resilient, e.g., malleable, thus requiring the application of an internal force to expand and set it at the target site. Typically, the expansive force can be provided by a balloon, such as the balloon of an angioplasty catheter for vascular procedures. The expandable structure 16 preferably provides sigmoidal links between successive unit segments which are particularly useful to enhance flexibility and crimpability of the stent.

Alternatively, the expandable structure 16 can be self-expanding. Structures for use in the devices of the present invention, including the expandable structure 16 (such as self-expanding structures) are provided by utilizing a resilient material, such as a tempered stainless steel, or a super-elastic alloy such as a Nitinol™ alloy, and forming the body segment so that it possesses its desired, radially-expanded diameter when it is unconstrained, i.e. released from the radially constraining forces of a sheath. In order to remain anchored in the body lumen, the expandable structure 16 will remain partially constrained by the lumen. The self-expanding expandable structure 16 can be tracked and delivered in its radially constrained configuration, e.g., by placing the expandable structure 16 within a delivery sheath or tube and removing the sheath at the target site.

Figure 4A:
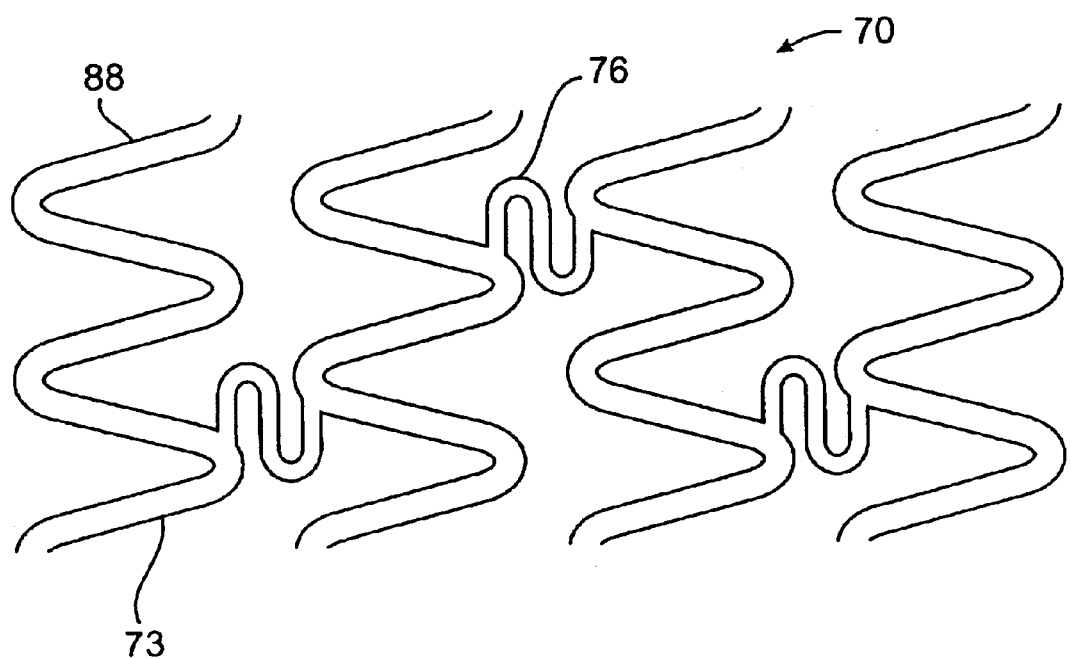
FIGS. 4A and 4B are schematic representations of an expanded view of a portion of the Stent of FIG. 3 showing areas having different mechanical profiles.
Figure 4B:
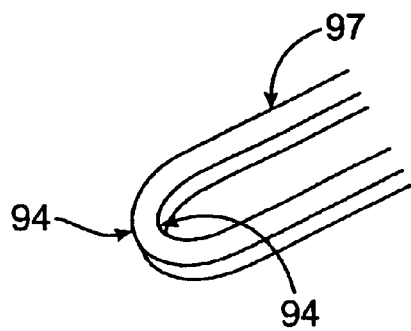

Now referring back to FIG. 3, and to FIGS. 4A and 4B, the exemplary stent 70 including features of the invention is shown to generally include a cylindrical frame 79 having proximal and distal ends, 82 and 85, tissue and luminal facing surfaces, 88 and 91, a plurality of radially expansible unit segments including rings 73. The unit segments, preferably, include segments having different mechanical profiles, as for example may be exhibit as a result of expansion. For example, the segments, may include relatively lower mechanical profile portions their lengths with relatively higher mechanical profile portions at bends, points, intersections, joints, or areas exposed to flow turbulence. The areas exhibiting relatively lower mechanical profiles, upon the expansion of the scaffold, typically do not under substantial bending, flexing, stretching, or compression, usually being less than about 5%. Some of the rings 73, as shown, are joined with at least one axially adjacent ring through expansion links 76, preferably having a sigmoidal shape, more preferably, an S shape having a relatively smooth profile along its length to minimize or reduce kinking upon expansion. Preferably, the rings 73, as shown, have a serpentine shape. Similarly, the links may comprise segments having different mechanical profile profiles along their length. For example, the links or joints may include relatively lower mechanical profile portions along their lengths with relatively higher mechanical profile portions at bends, points, intersections, joints, or areas exposed to flow turbulence (i.e., areas which are substantially in the direct line of fluid (e.g., blood or other bodily fluids) flow through the body).

Figure 5A:
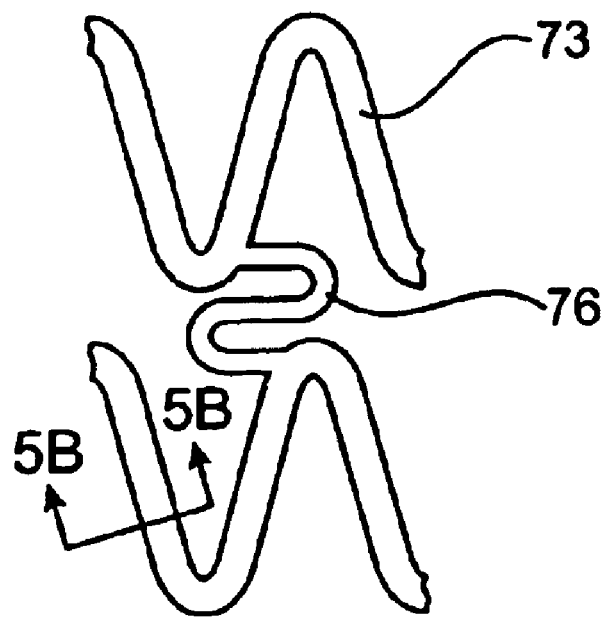
FIGS. 5A through and 8D are schematic representations of different embodiments of the stent of FIG. 4A.
Figure 5B:
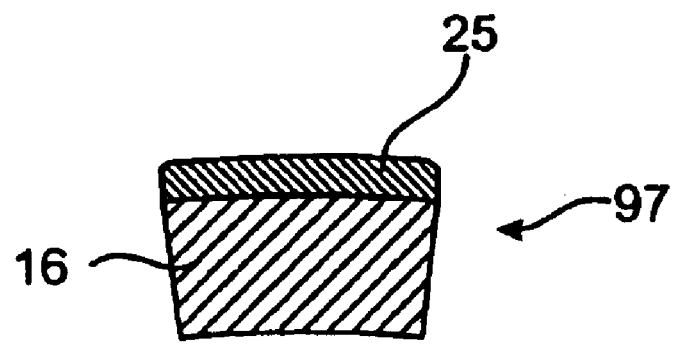
Figure 6E:
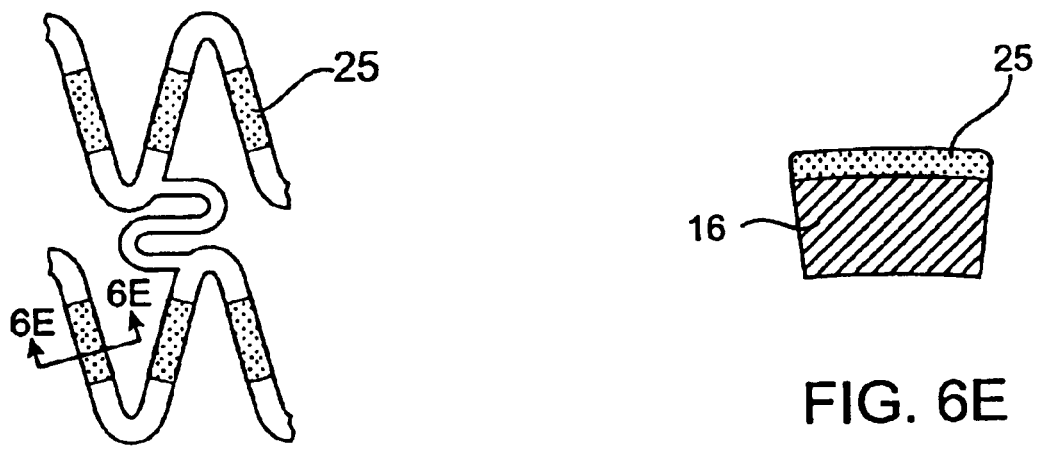
Figure 6F:
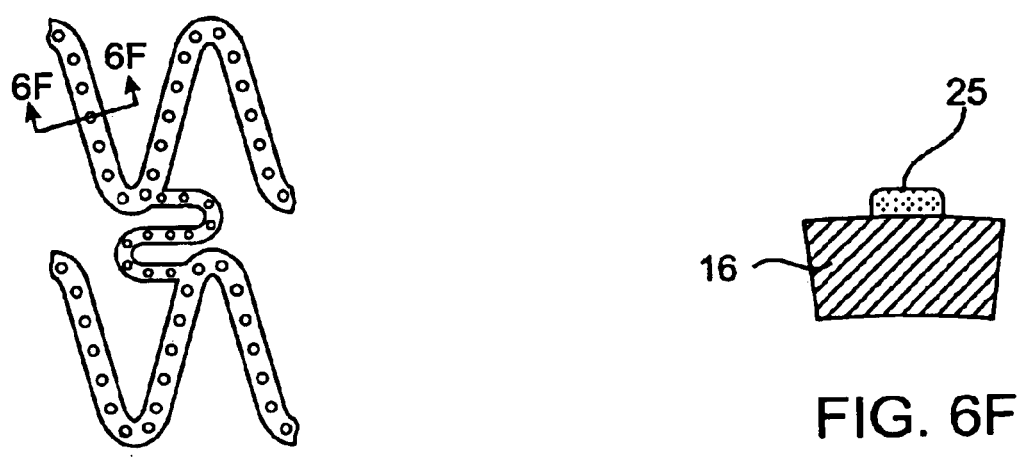
Figure 7A:
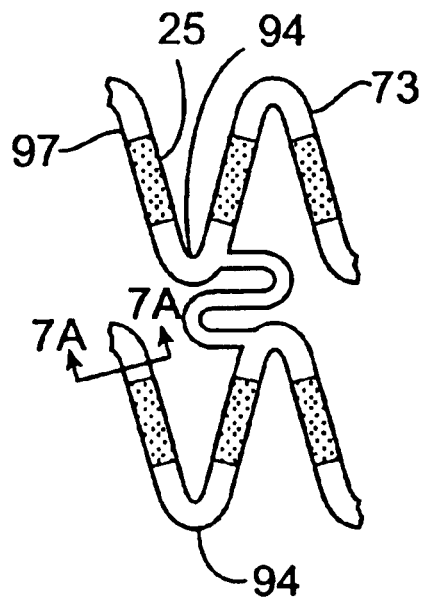
Figure 7A:
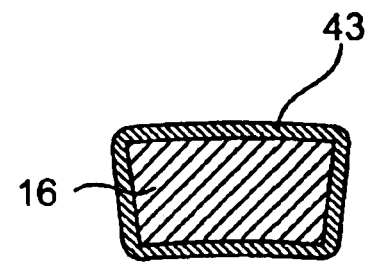
Figure 7B:
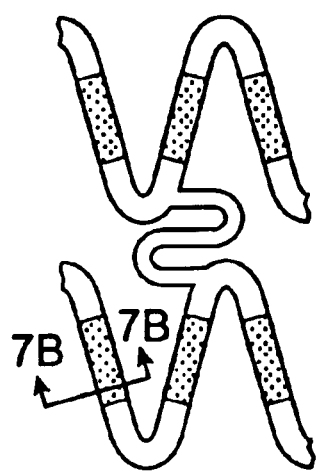
Figure 7B:
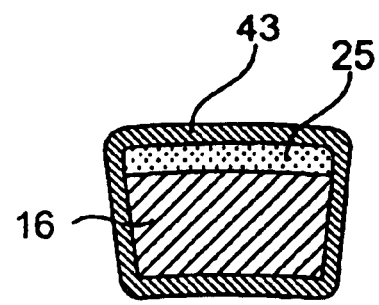
Figure 7C:
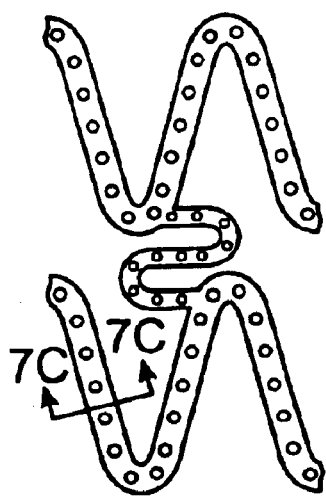
Figure 7C:
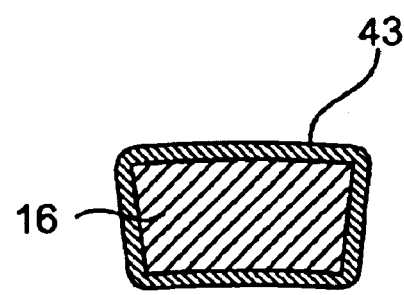
Figure 7D:
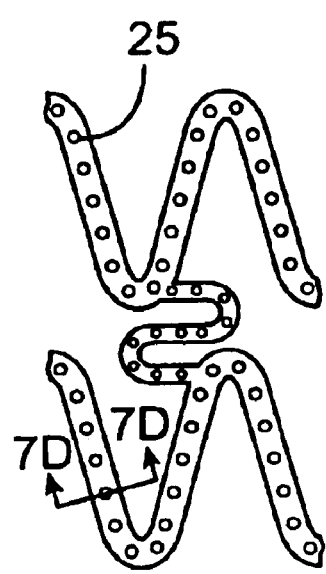
Figure 7D:
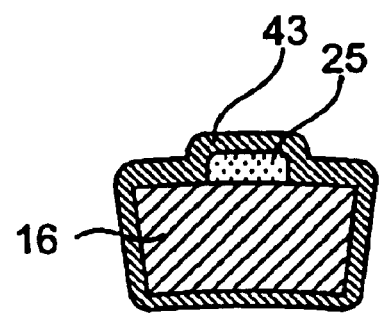
Figure 8A:
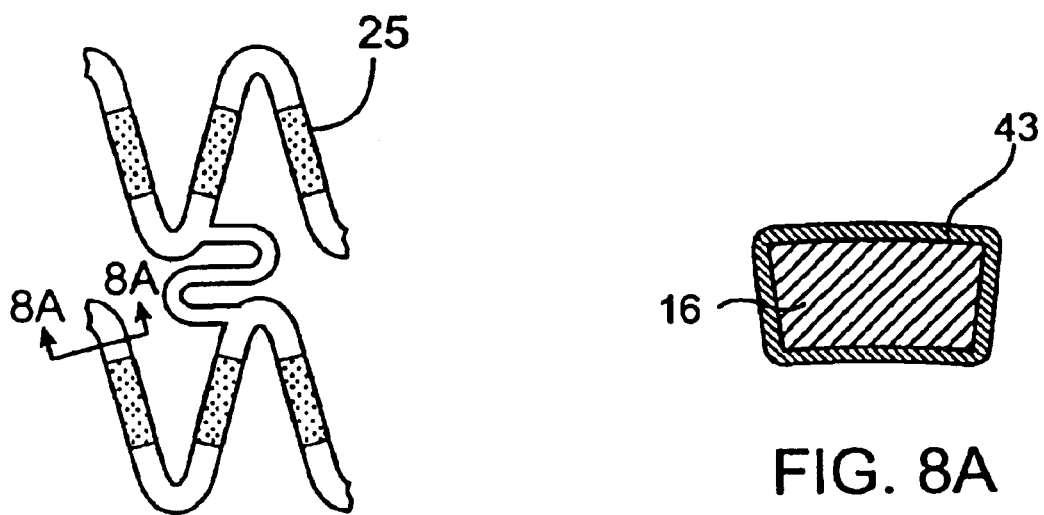
Figure 8B:
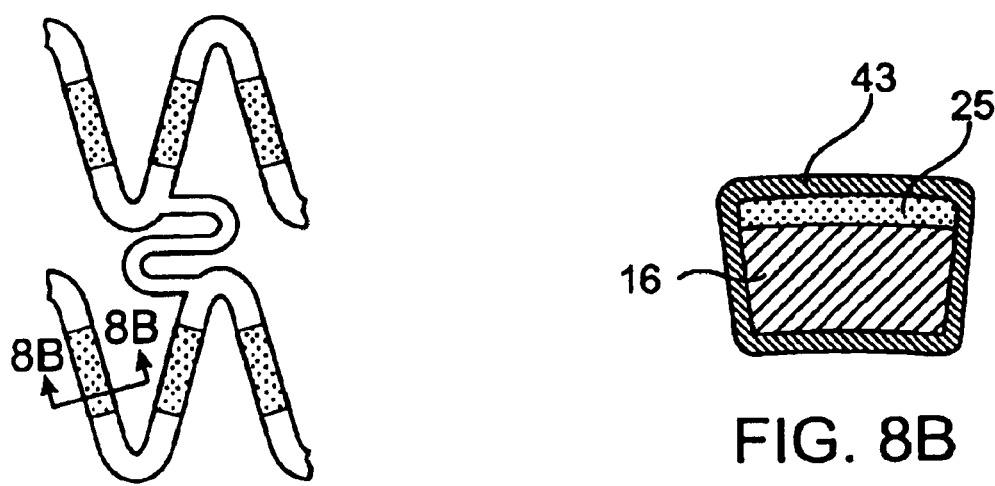
Figure 8C:
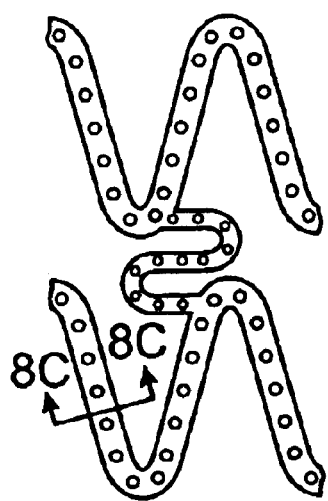
Figure 8C:
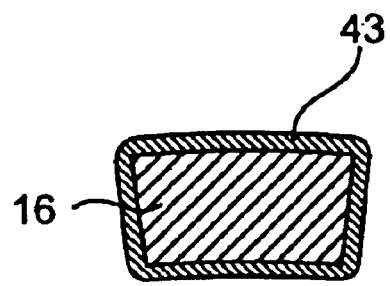
Figure 8D:
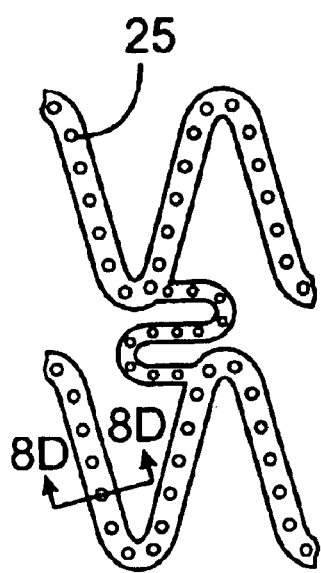
Figure 8D:
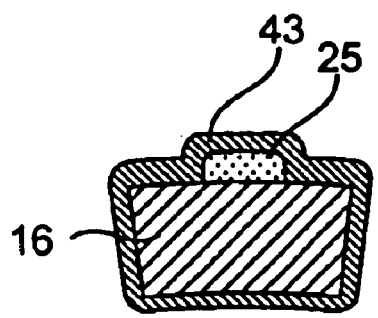

In an embodiment as shown in FIGS. 5A and 5B, the therapeutic capable agent is disposed adjacent all of the surface of at least one of the tissue facing and luminal facing surfaces of the structure on both the higher and lower stress areas, 94 and 97. As shown in FIGS. 6A through 6F, the source may be disposed on all of at least one of the tissue or luminal facing surfaces or only on the portions of the cylindrical frame, usually, only on those portions of the ring and/or joints, 73 and 76, having relatively lower mechanical profiles 97. The therapeutic capable agent may be applied in discrete portions, the portions having relatively larger areas (e.g., FIG. 6A), preferably on areas having relatively lower mechanical profile. Alternatively or additionally, the therapeutic capable agent may be present in smaller surface areas (e.g. FIG. 6B), preferably along the outer surfaces of the structure and away from sides and/or edges of the rings and/or the links (FIGS. 6D, 6F).

The source may vary in the amount of the therapeutic capable agent it comprises. When the source is present in a plurality of segments, as for example, when present in discrete portions, each source may comprise same or different therapeutic capable agents, at same or different amounts, and may make the therapeutic capable agent available to the susceptible tissue site at same or different phases and/or rates. The source may be the therapeutic capable agent, as for example when the therapeutic capable agent is a polymeric therapeutic capable agent, or may comprise a matrix as for example one or more therapeutic capable agents with same or different matrix forming material. The source may be present as a layer, a matrix, as part of a matrix interface, on or within the structure, or combinations thereof. The source may be present as a single layer, or a plurality of layers immediately adjacent one another or separated by another layer (such as another source or a rate-controlling element layer).

In an embodiment features of which are shown in FIGS. 7A through 7D, the stent further comprises a rate-controlling element 43 disposed adjacent (as for example, over) at least a portion of the structure. The rate-controlling element may disposed adjacent the structure on at least one of the tissue or luminal facing surfaces (e.g. FIG. 7A) or only those areas of the stent including the source 25 (e.g., FIG. 7B). When the rate-controlling element is disposed only in some but not all of the areas of the structure, the device may advantageously exhibit a relatively higher flexibility as compared to a structure which is completely covered with the rate-controlling element. In an alternate embodiment, the rate-controlling element may be disposed only on those areas of the structure having a relatively higher stress profile. This latter embodiment may be particularly useful when a device with greater overall coating thickness or one having a rate-controlling element applied over the entire structure, is desired. It should be appreciated that although the rate-controlling element as shown in the figures covers the entire perimeter of the structure, the rate-controlling element may cover only portions of the structure on one or both luminal and tissue facing surfaces and/or the ends of the device. Additionally, the rate-controlling element and/or the therapeutic capable agent may have a different thickness at various locations of the structure, as for example, on the sides being in direct flow of the bodily fluids.

In another embodiment features of which are shown in FIGS. 8A through 8D, the device comprises segments with and without therapeutic capable agent with the rate-controlling element 43 disposed adjacent both the segments including the therapeutic capable agent and those which do not. Preferably, the segments including the therapeutic capable agent are disposed adjacent the relatively lower mechanical profile areas with the relatively higher mechanical profile areas not including the therapeutic capable agent. The rate-controlling element comprises portions having different thicknesses.

Preferably, the thickness of the rate-controlling element disposed adjacent those segments of the device including the therapeutic capable agent (source as for example a reservoir) is relatively thinner than the thickness at other segments of the device. This variable rate-controlling element thickness profile provides for lower likelihood of cracking or pinhole formation at the higher stress areas while maintaining a relatively overall thin thickness. The minimization of the formation of the crack and/or pinhole formation at these segments even though no therapeutic capable agent is present, minimizes the likelihood of the uncontrolled rapid release of the therapeutic capable agent.

The thickness of the rate-controlling element, such as the nonporous rate-controlling element layer can range from about 50 angstroms (A) to about 50 microns (μm), from about 100 angstroms to about 20 microns, usually from about 100 angstroms to about 10 microns, normally from about 5000 angstroms to about 5 microns, and nominally from abut 7500 angstroms to about 2 microns.

Without intending any limitation, it is believed that the nonporous rate-controlling layer when applied over those portions of the structure experiencing relatively higher mechanical profile upon expansion, are susceptible to cracking and/or formation of pinholes upon expansion. The cracking and/or pinhole formation results in gaps in the rate-controlling layer. The gaps, in turn, will aid in the transport of the elution medium to the source, thus resulting in a more rapid release of the therapeutic capable agent to the corporeal body. Depending on the need and the desired effect, this effect may be desired to be reduced or minimized when it is necessary to release the therapeutic capable agent over a period of time. The therapeutic capable agent source may be absent from all or only portions of those segments of the stents which exhibit relatively higher mechanical profile.

In an embodiment having device segments with and without therapeutic capable agent, the thickness of the rate-controlling element preferably ranges from about 100 angstroms to about 5 microns; preferably, ranging from about 100 angstroms to about 1 micron at device segments including the therapeutic capable agent, and preferably ranging from about 0.5 to about 5 microns at device segments not including the therapeutic capable agent (e.g., high stress areas). Alternatively, the thickness of the rate-controlling element preferably ranges from about 0.5 microns to about 5 microns; preferably, ranging from about 1 micron to about 5 micron at device segments including the therapeutic capable agent, and preferably ranging from about 0.5 to about 5 microns at device segments not including the therapeutic capable agent (e.g., high stress areas). Preferably when the rate-controlling element comprises parylene, more preferably, parylene C, the stress area thickness of the rate-controlling element ranges from about 0.5 microns to about 10 microns.

In another embodiment, the device may include areas (e.g., distal and proximal ends of the device) having variable thickness of either or both the source and the rate-controlling element to allow for slower or faster release rates.

In an embodiment such as that shown in FIGS. 6A and 6B when the source is not present in the areas having relatively higher mechanical profile, the thickness of the nonporous rate-controlling element layer, preferably, range from about 50 angstroms to 5 microns.

In another embodiment, as shown in FIGS. 9A through 9D, the device may include apertures or orifices 100 in the therapeutic capable agent reservoir, made and used by similar processes as those described below, allowing for controlled release of the therapeutic capable agent to the targeted intracorporeal site.

Figure 9A:
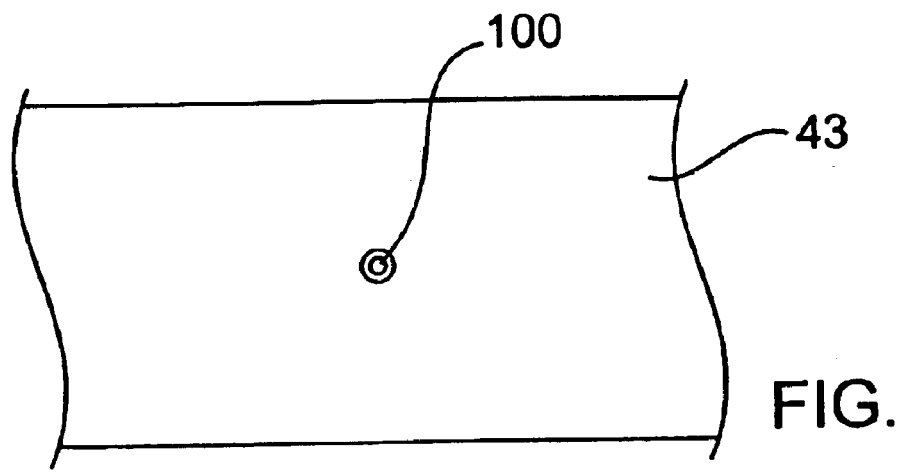
FIGS. 9A through 9D is a schematic representation of an embodiment of the stent of FIG. 4A having an aperture in the rate-controlling element.
Figure 9B:
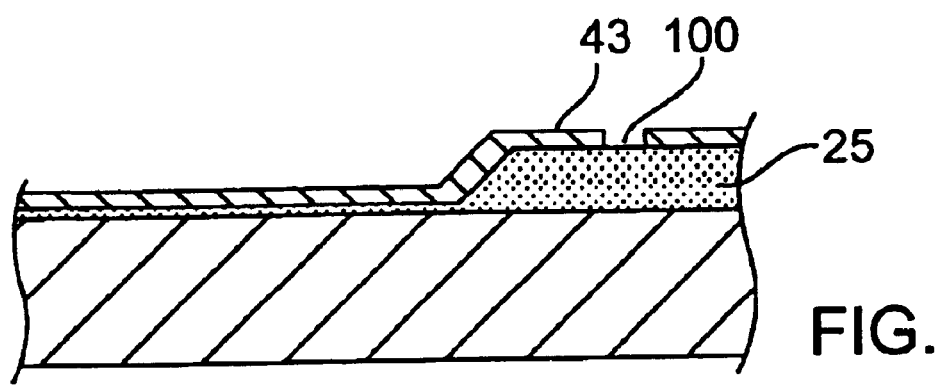
Figure 9C:
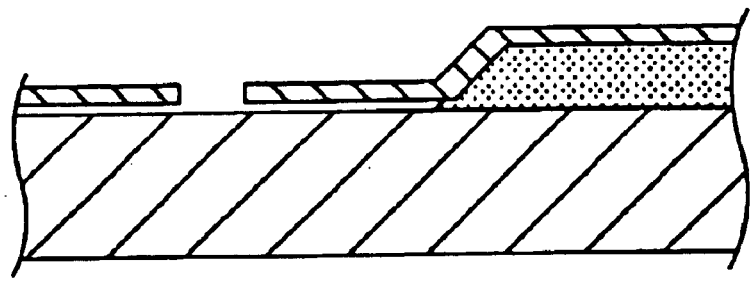

The apertures 100 may be positioned in the rate-controlling element (e.g., nonporus rate-controlling element such as parylene) either or both directly above and offset from the therapeutic capable agent source, as for example shown in FIGS. 9B and 9C, respectively.

The apertures may have depth running the entire thickness of the rate-controlling element layer or one shorter than the entire depth depending on the desired release rate. A single device may include similar or different apertures, sizes, locations, patterns, and depths in order to effectuate the desired release rate of the therapeutic capable agent. The aperture may range in opening from about 1 angstrom to about 100 microns, usually from about 1 angstrom to about 8 microns.

Figure 9D:
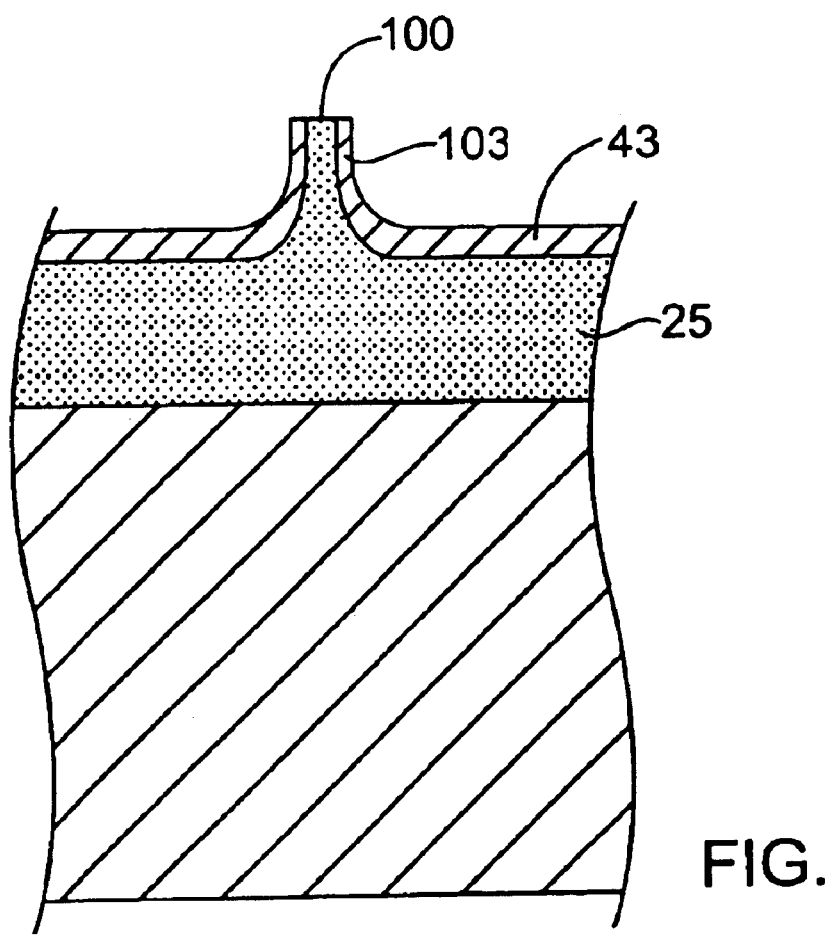
Figure 10A:
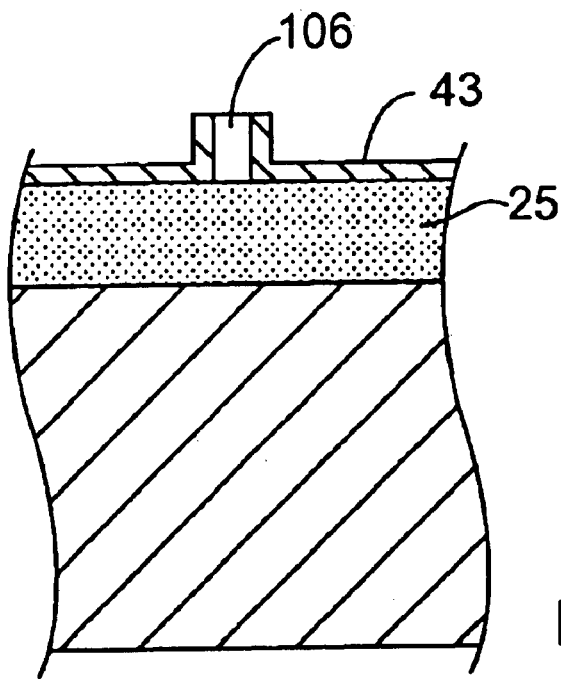
FIGS. 10A through 10D are schematic representation of different embodiments of methods for making the stent of FIG. 9.
Figure 10B:
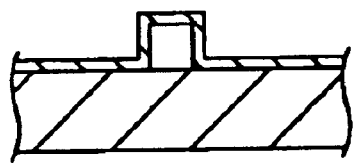
Figure 10C:
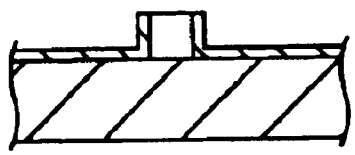
Figure 10D:
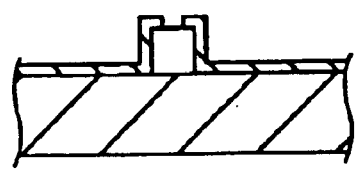

In an embodiment, as shown in FIG. 9D, the source and the rate-controlling element have at least a portion emerging out of the structure surface. The emerged portion 103 may include an aperture (surface or one having a more substantial depth) allowing for a capillary-like function. The emerged portion, advantageously, will be relatively more in contact with the tissue at the targeted intracorporeal site allowing for more direct release of the therapeutic capable agent to the tissue and less into the blood stream thus minimizing wash out of the therapeutic capable agent.

The amount and type of the therapeutic capable agent in each source (e.g., reservoir) may be the same or different. In an example, to minimize or reduce edge effect, the therapeutic capable agent is present at a greater amount at the ends of the device.

The embodiments including the at least one aperture may particularly be helpful in controllably increase the release rate of the therapeutic capable agent to greater than 2 μg/day, preferably greater than about 5 μg/day, and more preferably greater than about 10 μg/day; where the rate without the apertures may have been less than 50 μg/day, preferably less than 5 μg/day, more preferably less than 2 μg/day.

When using devices according to the present invention and including apertures in the rate-controlling element, greater consistency in the release rate of the therapeutic capable agent may be achieved. Typically, the rate-controlling element produces a relatively higher degree of variation in the release rate from device to device. Examples of factors bringing about such variation include, but are not limited to, the polymer's physical and chemical parameters which may vary lot to lot (e.g., structure, molecular weight, orientation, crystallinity, glass transition temperature, porosity, moisture content). Furthermore, as the therapeutic capable agent permeates through the polymeric rate-controlling element, phase separation and swelling of the therapeutic capable agent and the rate-controlling element may occur changing the porosity of the rate-controlling element, and thus resulting in a change in therapeutic capable agent release characteristics.

The apertures and holes may be made using a variety of tools and methods, including but not limited to: physical piercing tools (e.g., needle, wire, thin wall or sharpen edge tube, tube with different cross-sections and sharpen edge, beveled tube, pick); beams including laser, electron beam, or ionic beam bombardment, ion implantation, or the like to create one or more holes or orifices at precise locations or randomly on the rate-controlling element; inducing the formation of pinholes or orifices by applying a thin layer of rate-controlling element such that the pinholes are created during application of the coating and/or use of the device.

In an embodiment of a method of creating the orifices, as shown in FIGS. 10A through 10D, a small diameter wire, plastic or wax (e.g., bee wax), beading, tube, or similar object 106 is attached on the desired location of hole/orifice before applying the rate-controlling element. During the coating process, the object will be conformally coated along with the structure and becomes fixed to the structure. The object is then either partially (FIG. 10C) or fully (FIG. 10D) cut or removed (e.g., with a cutting tool), resulting in the exposure of a portion of the structure which is no longer coated. The object can be coated with microsoap, oil, detergent in water, or other release agents if it is desired to remove it after coating, leaving an orifice in its place.

Figure 11A:
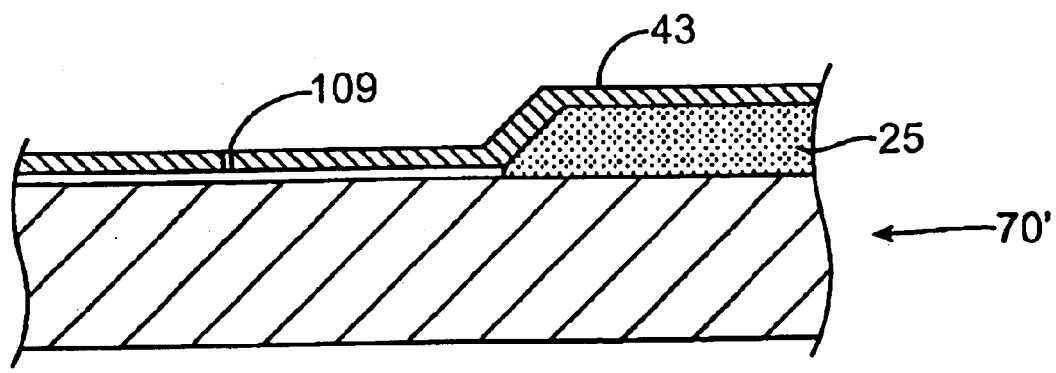
FIGS. 11A and 11B are schematic representations of an embodiment of the stent of FIG. 4A having deliberate disrupted areas.
Figure 11B:
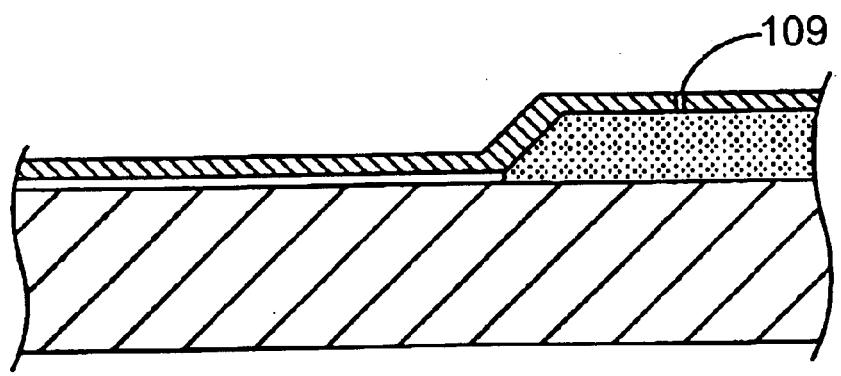

In another embodiment, as shown in FIGS. 11A and 11B, the device 70 includes deliberate disrupted areas 109 created as a result of expansion during the implanting of the device and/or subsequent exposure to targeted intracorporeal site environment.

By way of example, when a hydrophobic therapeutic capable agent layer is applied at the device areas having relatively higher mechanical profile profile, in particular when the at high therapeutic capable agent concentrations, the therapeutic capable agent and/or the rate-controlling element layer disposed adjacent (e.g., on the exterior surface of the therapeutic capable agent layer), may crack, disrupt, and/or form pinholes during as the device is expanded or exposed to the targeted intracorporeal site environment. Consequently, the therapeutic capable agent is released at a higher rate in this disrupted areas. As device is aged upon usage, the profile of the rate-controlling element may change (e.g., change in the size of the disrupted area, porosity increase as a result of movement of elution fluid to and from the therapeutic capable agent).

In yet another embodiment, the therapeutic capable agent has a degree of crystallinity less than about 90%, usually less than about 50%. The lower crystallinity may be achieved by heating any of the embodiments of the therapeutic capable agent-coated device (before or after the application of the rate-controlling element) to higher temperature, usually about or greater than the melting point of the therapeutic capable agent, for a period of time sufficient to bring about the desired degree of crystallinity, usually from about 1 minute to about 24 hours, typically from about 30 minutes to about 2 hours. As the therapeutic capable agent melts, it becomes more amorphous, thus less brittle. The amorphous (or semi-amorphous) nature of the therapeutic capable agent reduces creation of pin holes or unwanted interruptions in the rate-controlling element layer, thus a more controlled rate of release.

The heating of the therapeutic capable agent-coated device with or without the rate-controlling element may additionally serve to change, as for example, reduce the residual stress of the device due to the molecular rearrangement of the therapeutic capable agent and/or the rate-controlling element.

In an embodiment, the therapeutic capable agent/rate-controlling element-coated device is heated to a temperature for a period of time sufficient to change, usually reduce the residual stress in the rate-controlling element to about less than 10%, usually to about less than 5%, typically to about less than 1%, normally to about less than 0.5%. Typically, the device is heated to a temperature about or greater than the Tg of the rate-controlling element, usually between the Tg and the melting point of the rate-controlling element. The period of time ranges usually from about 1 minute to about 24 hours, typically from about 30 minutes to about 2 hours.

The residual stress of the coated device due to the rate-controlling element and/or the therapeutic capable agent may be also be reduced by other means such as: heating the device to a temperature below the Tg of the rate-controlling element or the melting point of the therapeutic capable agent, respectively, for a longer period of time; and using other sources of energy including ultrasonic, magnetic, or vibrational.

In an embodiment, the device comprises a layer of another rate-controlling element which is configured to bind, at least partially, with the therapeutic capable agent. In an embodiment Bovine Serum Albumin (BSA) is disposed adjacent the nonporous rate-controlling element (e.g., parylene) such that as the therapeutic capable agent (e.g., mycophenolic acid) diffuses or elutes out of the nonporous rate-controlling element, the therapeutic capable agent binds with the BSA, further delaying or controlling the release of therapeutic capable agent. Other examples of another rate-controlling element capable of binding with the therapeutic capable agent include quarternary ammonim compounds such as polyethylene imine. In one embodiment a hydrogel compound is disposed under either or both the therapeutic capable agent and the rate-controlling element or in the matrix. As body fluids come in contact with the hydrogel compound, the hydrogel compound swells causing a change in the flow or diffusion properties of the therapeutic capable agent through the rate-controlling element, as for example by causing disruptions in the rate-controlling element layer.

The expandable structure may incorporate the therapeutic capable agent and/or the optional another compound, by coating, spraying, dipping, deposition, or painting the therapeutic capable agent onto the prosthesis. Usually, the therapeutic capable agent is dissolved in a solvent prior to its application. Suitable solvents include aqueous solvents (e.g., water with pH buffers, pH adjusters, organic salts, and inorganic salts), alcohols (e.g., methanol, ethanol, propanol, isopropanol, hexanol, and glycols), nitrites (e.g., acetonitrile, benzonitrile, and butyronitrile), amides (e.g., formamide and N-dimethylformamide), ketones, esters, ethers, DMSO, gases (e.g., $CO_2$), and the like. The therapeutic capable agent-structure is then allowed to dry. Alternatively, the therapeutic capable agent may first be prepared into a matrix by mixing or dissolving the therapeutic capable agent and matrix material, alone or in combination with a solvent, prior to its incorporation to the structure.

In an exemplary method of making the devices of the present invention, a bare or uncoated stent is first fabricated and/or processed (e.g., descaled, electropolished, passivated using conventional methods prior to the incorporation of the therapeutic capable agent. By way of example, the bare stent is optionally treated with coupling agents such as silane, plasma deposited coating, plasma treatment, coronary discharge, and/or other means to promote and/or enhance the adhesion of the rate-controlling element to the bare stent in subsequent steps.

A bare structure (e.g., prosthesis) or a coated therapeutic capable agent-structure may be placed in vapor deposition chamber or plasma deposited coating chamber. A therapeutic capable agent in solid or liquid form can be placed directly under the structure in a container or dish in the same chamber. The container may be heated to a desired temperature (i.e., the boiling point or sublimation temperature of the therapeutic capable agent), simultaneously or periodically while the rate-controlling element (e.g., parylene) or plasma deposition occurs. Since the chamber is in vacuum, the gaseous therapeutic capable agent will, by line of sight, coat the structure. The dish configuration (round, square, rectangular, depth, cover with holes), the therapeutic capable agent amounts/distribution, presence of a perforated shield/fence, and other factors will control the thickness, distribution, and uniformity of the therapeutic capable agent dispersed or deposited directly or indirectly onto the stent. Alternatively, nano-size deposition techniques may be used to selectively apply the therapeutic capable agent and/or rate-controlling element to or onto the structure.

Figure 12:
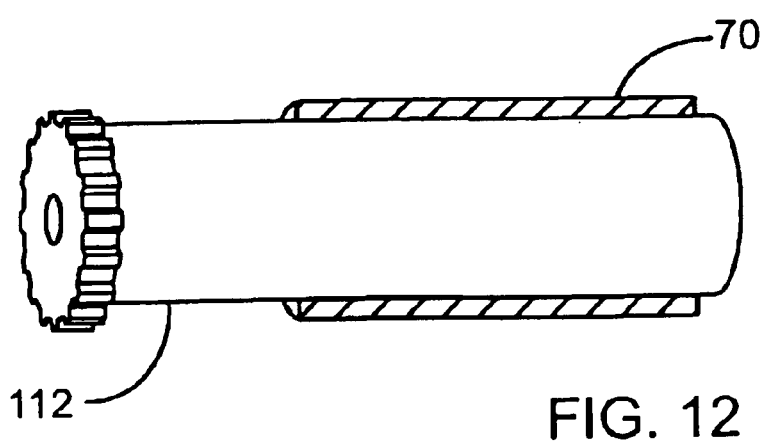
FIG. 12 is a schematic representation of an embodiment of a method of making the stent of FIG. 4A disposed on a rotating mandrel.

By way of example, herein is described a more detail process for applying rate-controlling element and/or therapeutic capable agent on or within a structure. A small diameter mandrel 112 or other means is inserted into the stent. The mandrel-stent structure is then placed in the deposition chamber. Preferably, the mandrel-stent structure may be removably affixed on a rotating device inside the chamber to get more consistent coating, as for example shown in FIG. 12. The deposition chamber is sealed. The rate-controlling element material or its precursor (e.g., parylene C, in its dimer form) is loaded into the ambient temperature vaporizer zone through a load door. The door is then sealed. The amount of rate-controlling element or its precursor loaded depends on the desired or required coating thickness, total surface area of the substrate, deposition chamber size, and type of the rate-controlling element (e.g. parylene N, C, D or F). In an exemplary embodiment, the amount of rate-controlling element precursor (e.g., parylene C dimmer) loaded was about 3 grams. The sealed system is then pumped down by a vacuum pump to a steady state base pressure of for example about −4 to about 100 mTorr, usually from about 4 to about 15 mTorr.

Once the system base pressure has been reached, the vaporizer zone is then heated to an appropriate temperature, as for example from about 70 to about 200° C. (e.g., 80° C.). The vaporizer heater is cycled on/off by the chamber pressure controller in order to maintain the pressure in the chamber. As the pressure reaches the chamber-pressure set point, the power to the vaporizer heater is reduced to prevent the chamber pressure from overshooting. The vaporizer heater is then maintained at a temperature where the chamber pressure is at the pressure set point to aid in the gradual vaporization and/or sublimation of the solid rate-controlling element or its precursor (e.g., parylene dimer).

As the vacuum pump operates, the precursor gas flows downstream through the pyrolysis zone. The high temperature pyrolysis furnace cleaves the dimer gas to form the rate-controlling element (e.g., parylene monomer) gas. As the reactive monomer gas exits the pyrolysis zone and enters the deposition chamber containing the structure (e.g., the prosthesis structure) deposition takes place. The monomer will deposit and polymerize on all or substantially all of the ambient temperature surface within the deposition chamber which are available for coating.

As the monomer gas flows into the deposition chamber, the additional gas causes the pressure in the chamber to rise. Typically, the desired rise ranges from about 10 to about 40 mTorr above the base pressure for Parylene C. The growth rate of the rate-controlling element (e.g., nonporous parylene film) in the deposition chamber is proportional to the partial pressure of the monomer gas. A feedback control system may be used to maintain the desired pressure within the deposition chamber by controlling the rate at which dimer is vaporized.

Concurrently and/or sequentially with the rate-controlling element monomer gas (e.g., parylene C monomer gas) depositing onto the structure surface, the dish containing the therapeutic capable agent is heated to above the boiling point or sublimation temperature of the therapeutic capable agent causing the gaseous therapeutic capable agent to flow upward in the vacuum chamber. Since the structure is in the line of sight with the therapeutic capable agent gas, the structure is also coated with the therapeutic capable agent. The therapeutic capable agent, thus, may be coated on the structure as part of a matrix (e.g., therapeutic capable agent with rate-controlling element) or as a separate layer. It should be appreciated that in the latter case, the therapeutic capable agent may be coated onto the structure first followed by a coating of the rate-controlling element or vice versa. The separate layers, may of course, form a matrix interface therebetween.

Because of the gas flow dynamics associated with the vacuum pump, any rate-controlling element monomer gas and therapeutic capable agent gas that flows into the deposition chamber and which does not deposit onto the structure, will tend to flow through the cold trap and toward the vacuum pump.

When the dimer and/or therapeutic capable agent have been completely vaporized, the pressure in the deposition chamber will decrease and approach the base pressure. At this point, the deposition cycle has completed, the system can be brought back to atmospheric pressure and the coated stent removed.

The process parameters for applying parylene (e.g., parylene C) onto a structure, in an exemplary embodiment, were as follows. The parylene process parameters were: vaporization (sublimation) temperature of about 80° C., pyrolysis temperature of about 650° C., base pressure (vacuum) of about 15 mTorr or less, pressure (vacuum) set point of about 20 mTorr above base pressure. The therapeutic capable agent evaporation parameters were: dish temperature before evaporation being below boiling point or sublimation temperature, dish temperature during evaporation at or above boiling point or sublimation temperature, base pressure (vacuum) of about 15 mTorr or less, and pressure (Vacuum) set point of about 20 mTorr above base pressure.

Figure 13A:
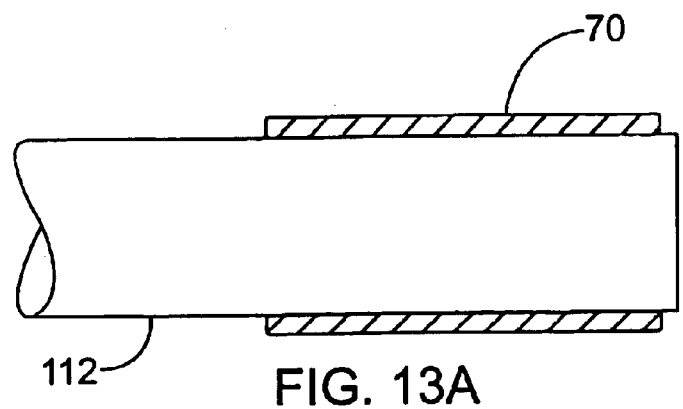
FIGS. 13A through 13D are schematic representation of different embodiments of apparatus and methods for making the stents of FIG. 4A.

In an exemplary embodiment of a method of making the devices of the invention, as shown in FIG. 13A, a mandrel 112 having an outer diameter, preferably, similar to that of the inner diameter of the stent is positioned within the frame of the stent. To better maintain the stent onto the mandrel, the stent may be sufficiently crimped onto the mandrel so as to prevent the stent from slipping off the mandrel. The mandrel, when formed of a solid material or one having a closed exterior surface may optionally serve as a mask to shield the inner surface of the cylindrical frame (i.e., the luminal surface of the stent) during subsequent coating steps.

Optionally, a mandrel having an outer diameter sufficiently smaller than the inner diameter of the stent and/or one being formed of a sufficiently open lattice structure (the pattern preferably designed to prepare the desired coating pattern on the stent) may be used to allow for the coating of the luminal surface of the stent during the coating process.

Optionally, an expansible balloon 115 having a generally cylindrical expanded shape and formed, preferably, from a material such as silicone rubber, polyurethane, nylon, or the like, may be used as the mandrel. The balloon in its expanded configuration, preferably, has an outer diameter, similar to that of the inner diameter of the stent. Use of the balloon as the mandrel allows for easier removal from the stent after the completion of the coating.

Figure 13B:
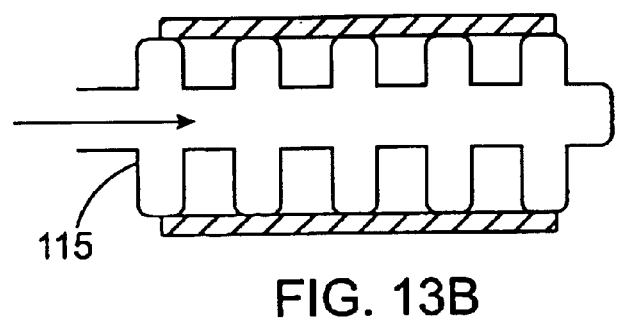

As shown in FIG. 13B, the balloon may be formed so as to include a series of longitudinally spaced apart areas of larger diameter (such as a centipede shape). The larger diameter areas are sufficiently spaced apart so as to come in contact with the luminal surface of the stent being of relatively higher mechanical profile, thus masking the relatively higher stress areas during the coating process.

In yet another optional embodiment, the balloon comprises an exterior tubing formed from a soft material such as soft rubber such that the balloon can be positioned in the spaces between the struts and links to mask the edges of the same, thus, allowing coating only on the tissue facing surface of the stent while masking the edges (e.g., thickness) of the rings.

Figure 13C:
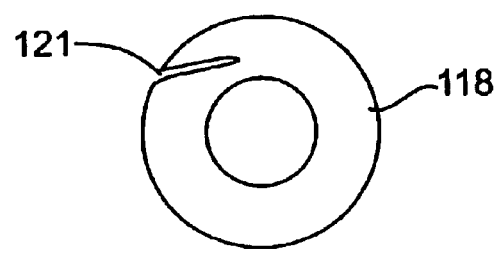
Figure 13D:
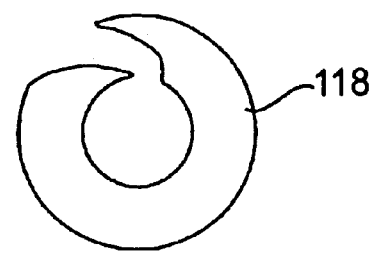

In yet another embodiment of a process of making the devices of the present invention, to avoid or minimize the coating of the stent at the relatively higher mechanical profile areas, one or more washers shown in FIGS. 13C and 13D, such as silicone rubber washers (or of other material in other shapes as may be desired), are disposed over the relatively higher mechanical profile areas of the tissue facing surface of the stent, thus masking the areas during the coating process. After the application of the rate-controlling element, the the washer, such as that depicted in FIG. 13B, which may be torn across a tear 121 to allow for easy removal from the device. The washers may have an inner diameter substantially the same, slightly larger, or more preferably, smaller than the inner diameter of the stent. Preferably, the washers have a width greater than the width of the relatively higher mechanical profile areas of the stent.

In yet another embodiment, the structure may be masked by creating a negative image of the structure on another material such as a plastic or metal tube. The tube can be slitted into two halves. The slitted tube is then clamped onto the stent. Only the outer surface of the stent is exposed. The sides and luminal surface are not exposed. When the therapeutic capable agent is sprayed onto the stent, therapeutic capable agent is only on the outer surface of the stent. This would result in FIG. 6B, 6D, or similar embodiments.

Figure 14A:
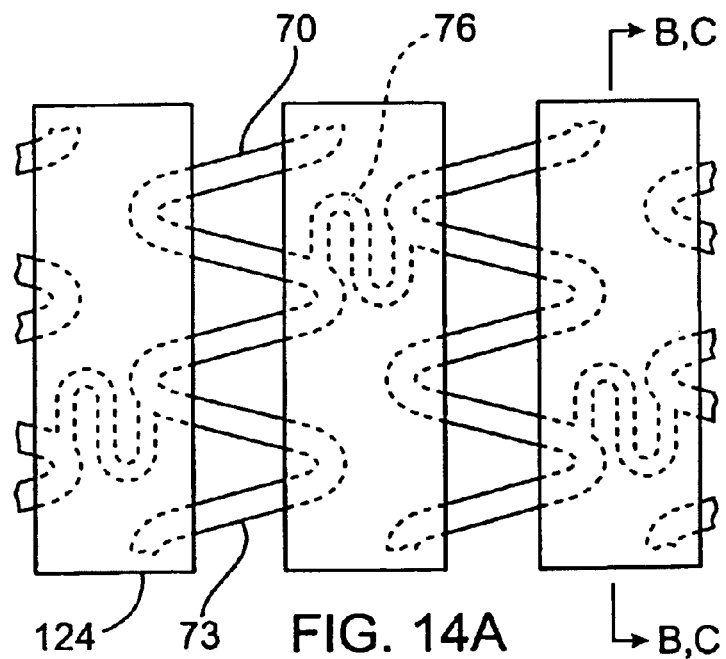
FIGS. 14A through 14C are schematic representations of another embodiment of masking apparatus and methods for making the stent of FIG. 4A.
Figure 14B:
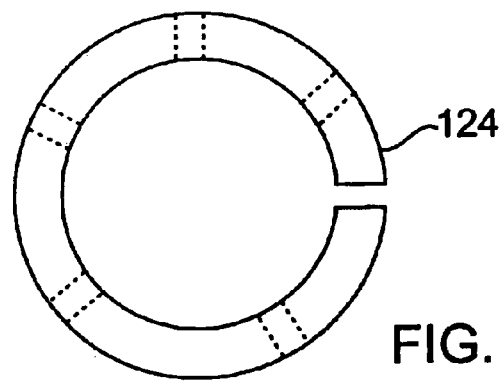
Figure 14C:
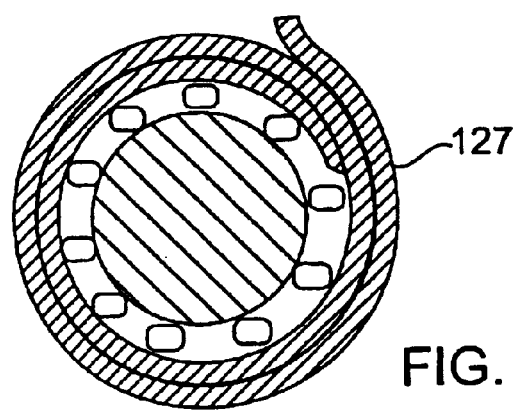

To mask desired portions, such as structure areas having relatively higher mechanical profile, the stent structure may be masked, as shown in FIG. 14A, by a variety of ways such as a flat plate, curve plate, a tube, or other surfaces 124 having exposed apertures or slots, such as FIG. 14B, such that the aperture and/or slots expose the desired areas to coating (e.g., low mechanical profile areas) while masking the other areas (e.g., high mechanical profile areas). Alternatively, a flexible tape 127 as shown in FIG. 14C may be used to cover the tissue facing surface of the stent at the high stress areas.

In another embodiment, the stent is either not masked or is minimally masked during the coating. If desired, unwanted areas of coating may be removed by way of application of fine tip sand blaster, high pressure air nozzle, high pressure spray nozzle with an appropriate solvent (e.g., methanol, ethanol, isopropanol acetone, water), low power laser, electron beam, or the like. Alternatively, a very fine spray nozzle or nano-size deposition tool may be used to selectively apply the therapeutic capable agent and/or rate-controlling element to or onto the structure.

Figure 15A:
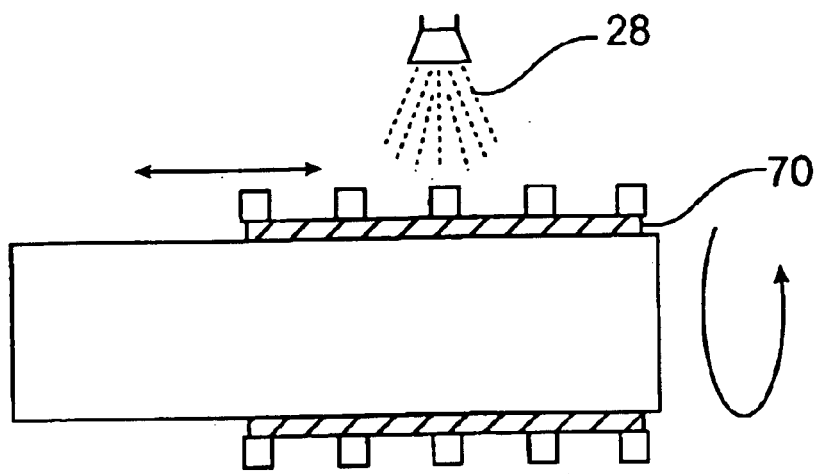
FIGS. 15A and 15B are schematic representations of spray apparatus and methods for making the stent of FIG. 4A.
Figure 15B:
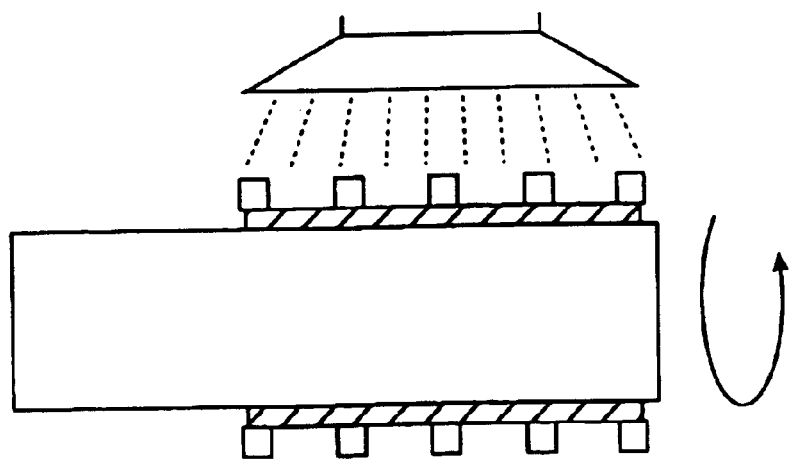

The stent is then exposed to a source of therapeutic capable agent, as shown in FIGS. 15A through 15B. The therapeutic capable agent 28 is preferably dissolved or mixed in an appropriate solvent(s) and/or matrix, and applied by methods such as spraying. Preferably, the stent is removably fixed to a rotating device so that the stent may be evenly disposed with the source (therapeutic capable agent as dissolved in a solvent and/or matrix material). Preferably, the width of the source application device is sufficiently long so as to apply the source onto the entire length of the stent. The therapeutic capable agent is dissolved in appropriate matrix material and is then, preferably, sprayed onto the stent (masked or otherwise).

Alternatively, the stent may be coated with the source using other techniques such as powder coating while the stent is in a vacuum deposition chamber or plasma deposition/glow discharge chamber, pulse laser assisted deposition technique, vacuum deposition with the therapeutic capable agent being vaporized in the high vacuum chamber and thereafter deposited onto the stent. After the completion of the coating, the masks are removed from the stent. Excess therapeutic capable agent, if necessary or desired, may be removed from the coated stent as described earlier.

The thickness of the therapeutic capable agent and/or the matrix coating may be controlled by the time period of spraying and the speed of rotation of the mandrel. The thickness of the therapeutic capable agent and/or matrix coating is typically in a range from about 1 angstroms (A) to about 50 microns (μm), from about 100 angstroms to about 20 microns, usually from about 100 angstroms to about 10 microns, normally from about 5000 angstroms to about 5 microns, and nominally from abut 7500 angstroms to about 2 microns. Once the stent has been coated with the therapeutic capable agent andlor the matrix, the stent may be placed in a vacuum, oven, or vacuum oven to complete the evaporation of the solvent.

A nonporous parylene coating is clear, transparent, and has film-like qualities. It is resistant to solvent and will not swell more than about 3% in film thickness in organic solvents such as alcohol (isopropanol, methanol, ethanol), ketones (acetones and 2,3-pentanedione), aliphatic hydrocarbons (iso-octane), aromatic hydrocarbons (xylene, toluene), chlorinated olefins (trichloroethylene), chlorinated aromatics (chlorobenzene and O-dichlorobenzene), heterocyclic bases (pyridene), and fluorinated solvents (trichlorotrifluoroethane). In addition, after swelling, nonporous parylene swelling is completely reversible once the solvents have been removed by vacuum drying.

In an embodiment of a process for making a partially rate-controlling element coated device the process may comprise any one or more of the process steps discussed above. By way of example, the structure may be coated with nonporous polymers by means other than vapor deposited coatings (i.e., nonporous parylene) or other than nonporous plasma deposited or glow discharge coating. Alternatively, a portion of the vapor deposited coating or plasma deposited/glow discharge coating at the stressed areas may be removed with a laser, electronic beam, or other means; masking the areas where rate-controlling element is not desirable. In another embodiment, after the therapeutic capable agent is applied, the stressed areas (with little or no therapeutic capable agent) may masked before the stent is coated with the rate-controlling element. The mask is removed after coating.

The desired areas of the stent may be shielded with fences (cold or heated) to prevent flow of parylene reactive intermediate, mono(p-xylylene), during vacuum deposition of coating or the plasma free radicals during plasma deposited/glow discharge coating to the stressed area of the stent.

Heated films, wires, or the like may be brought in contact with the desired areas of the stent such that the stent resists condensation of the parylene reactive intermediate, mono (p-xylylene), during vacuum deposition of the coating or the plasma free radicals during plasma deposited/glow discharge coating on the stressed area of the stent.

In yet another embodiment, one or more tubes carrying a flowing heated fluid may be brought into contact with the desired areas of the stent during vacuum deposition of the coating or plasma deposited/glow discharge coating. These shielded areas of the stent are heated and resist condensation of the parylene reactive intermediate, mono(p-xylylene), during vacuum deposition of the coating or the plasma free radicals during plasma deposited/glow discharge coating on the stressed area of the stent.

Non-contact sources (e.g., convection heat source, infrared, ultra violet, or the like) and may be directed at desired areas of the stent, or films, wires, tubes, and the like which are in contact with desired areas of the stent.

Areas of the stent which are not coated with nonporous parylene or plasma deposited/glow discharge coating rate-controlling element can be coated with therapeutic capable agent by masking the areas of the stent with the nonporous polymer rate-controlling element and then applying the therapeutic capable agent on the unmasked area as described above.

If desired, the nonporous rate-controlling element can be infiltrated with therapeutic capable agent(s) or small non-active molecules by placing the stent, the therapeutic capable agent, and the rate-controlling element (e.g., nonporous rate-controlling element) in one or more solvents that will swell or can transmit into and through the nonporous rate-controlling element, for a period of time, as for example ranging from about 1 second to about 1 week, usually from about 1 hour to about 72 hours, and often from about 2 hours to about 24 hours. The solvent(s) may or may not contain the therapeutic capable agent or non-bioactive molecules that are dissolved in the solvent(s) depending on whether the source of the therapeutic capable agent or non-bioactive molecule is from the therapeutic capable agent reservoir or from an external source or both. The temperature of the solvent(s) during swelling can range from room temperature to elevated temperatures, up to and including the boiling point of the solvent(s).

The stent with the therapeutic capable agent reservoir and nonporous rate-controlling element are heated to a temperature below which the nonporous rate-controlling element will not be damaged or at temperatures below which the therapeutic capable agent will not significantly degraded, for a period of time, usually ranging from about 1 second to about 1 week, often from about 1 hour to about 72 hours, and nominally from about 2 hours to about 24 hours.

The stent with therapeutic capable agent reservoir and nonporous rate-controlling element can come in contact with one or more vaporized solvents, which are preferably organic, for a period of time, usually ranging from about 1 second to about 1 week, often from about 1 hour to about 72 hours, and nominally from about 2 hours to about 24 hours. The coated therapeutic capable agent stent may then be crimped onto a balloon of a PTCA catheter and deployed into the targeted intracorporeal site.

In another embodiment of a method of making, the expandable structure is first pre-treated by silane treatment, such as methacryloxypropyl-trimethoxysilane (A-174) or other silane coupling agents, to minimize the formation of cracks and/or pinholes during the expansion of the device. By way of example, in a method of making the device, the expandable therapeutic capable agent-coated structure is immersed into a solution of methanol:water:silane having a ratio of about 100:100:2 for a period of time, preferably, 15 minutes. The structure is then removed and let dry for about 10 minutes and is then rinsed with IPA. The treated structure is then processed as described above to further include the rate-controlling element. The silane treatment helps promote the adhesion of the rate-controlling element, such as the non-porous parylene, to the structure material, such as stainless steel. Alternatively, a nonporous plasma deposited/glow discharge coating (e.g., methane, $C_2F_2$, xylene, silane dimmer) can also be applied to the structure surface to help promote the adhesion. The pre-treatment of the structure with adhesion promoting agents helps enable the application of relatively thinner thickness of rate-controlling element, at for example the high stress areas of the structure. The pre-treatment may be provided in any of the other embodiments. By way of example, the pre-treatment may be applied over the therapeutic capable agent source (e.g., reservoir). However when rate-controlling element-structure adhesion profiles of lesser strength are desirable, the pretreatment may not be necessary.

It may, alternatively, be desirable to have a thicker rate-controlling element coating adjacent the therapeutic capable agent source while having a stable yet thinner coating thickness at the stressed areas of the device. The thicker coating of the rate-controlling element produces a deliberate decrease in the release rate of the therapeutic capable agent to the targeted intracorporeal site. In an embodiment, the coating of the rate-controlling element at those device segments not including the therapeutic capable agent, preferably the higher stress areas, comprises a relatively higher thickness to help minimize formation of cracks and/or pinholes.

To accomplish the variable or selective coating of the rate-controlling element, processes similar to those described earlier may be utilized. To effectuate the controlled coating, factors such as the flow rate of the rate-controlling element monomer gas (e.g., parylene) may be reduced and/or its location may be controlled.

In an embodiment, a removable physical fence (e.g., wires, bars, tube having the same width as the therapeutic capable agent reservoir, slotted plate), may be positioned adjacent the areas desired to have a smaller thickness of the rate-controlling element deposited thereon (e.g., the stent therapeutic capable agent reservoir) to controllably limit the deposition of the rate-controlling element.

Alternatively, low temperature heat (e.g., above room temperature) may be aimed at the desired thin area to minimize and/or reduce the reaction between the rate-controlling element monomer gas and the material at the desired thin area. Examples of such heat sources include infrared, ultra violet, heating coils, heating elements, or any small source of lighting that can be aimed at the desire area and generate differential amount of heat.

In yet another embodiment, a deliberate smaller quantity of rate-controlling element may be applied when using the appropriate processes such as spray coating.

By way of example, porous rate-controlling element may be obtained, such as a porous parylene C layer, using any of the following exemplary methods.

In an embodiment for creating a device having a porous rate-controlling element, such as porous parylene or plasma deposited/glow discharge film, the temperature of deposition may be substantially below the glass transitional temperature of the rate-controlling element material. By way of example, for parylene C as the rate-controlling element, the glass transitional temperature, Tg, is approximately 80 to 100° C. As the deposition temperature increases, the crystallinity of the film increases. Higher temperatures allow rearrangements and molecular motion possible after the coating is deposited on the surface of the substrate. The polymeric chain becomes more conformationally ordered. As the deposition temperature decreases, the crystallinity of the film decreases, becoming more amorphous. When the temperature is decrease further, from for example, −40° C. to near liquid nitrogen temperatures (−196° C.), the rate-controlling element film becomes increasingly amorphous and porous. It should be noted that the porous films may be changed to a targeted percentage, or usually change to a nonporous morphologyby annealing the thin films at suitable temperatures for a length of time such as 205° C. in Nitrogen gas for about two hours.

In another embodiment for creating a device having a porous rate-controlling element, porous parylene C layer, any one or more combinations of the following parameters may be used: vaporization (sublimation) temperature of about 20° C. to about 200° C., preferably about 40° C. to about 60° C.; pyrolysis temperature of about 400° C. to about 900° C., preferably about 500° C. to about 650° C., and about or greater than 750° C. for porous parylene C; base pressure (vacuum) of about −4 to about 200 mTorr, preferably about 100 mTorr or greater; pressure (vacuum) set point of about 0 to about 200 mTorr above base pressure; stent temperature of about −196° C. to about 0° C., preferably about −50° C. or lower, more preferably at about −100° C. By way of example, in an exemplary embodiment for making the porous parylene C rate-controlling element layer at higher base pressure and or pressure set point, the parameters were set as follows: vaporization temperature of 140° C., pyrolysis temperature of 690° C., base pressure of 120 mTorr, pressure set point of 135 mTorr, stent temperature at room temperature. By way of example, in an exemplary embodiment for making the porous parylene C rate-controlling element layer at lower pyrolysis temperature and or vaporization temperature, the parameters were set as follows: vaporization temperature of 60° C., pyrolysis temperature of 650° C., base pressure at 15 mTorr, pressure set point at 20 mTorr, and stent temperature at room temperature.

In another exemplary embodiment, porous rate-controlling element may also be obtained by using the methods described above for making a nonporous coating but changing the parameters to those described with respect to the parameters for making a porous rate-controlling element, and furthermore modifying one or more of the process steps as follows: reducing the flow of gaseous parylene or plasma deposited/glow discharge reactive monomers into the stent loaded chamber by blocking inlet port to coating chamber; placing fences around the stent to decrease the rate of deposition; adding impurity to parylene dimmer; introducing gases into the chamber during coating; concurrently plasma depositing of coating during parylene coating; having plasma coating having heat labile groups; releasing gas above a post-treatment temperature; concurrently plasma depositing of coating during parylene coating; having plasma coating with groups which are susceptible to degradation when exposed to solvents or enzymes found in the body.

Figure 16:
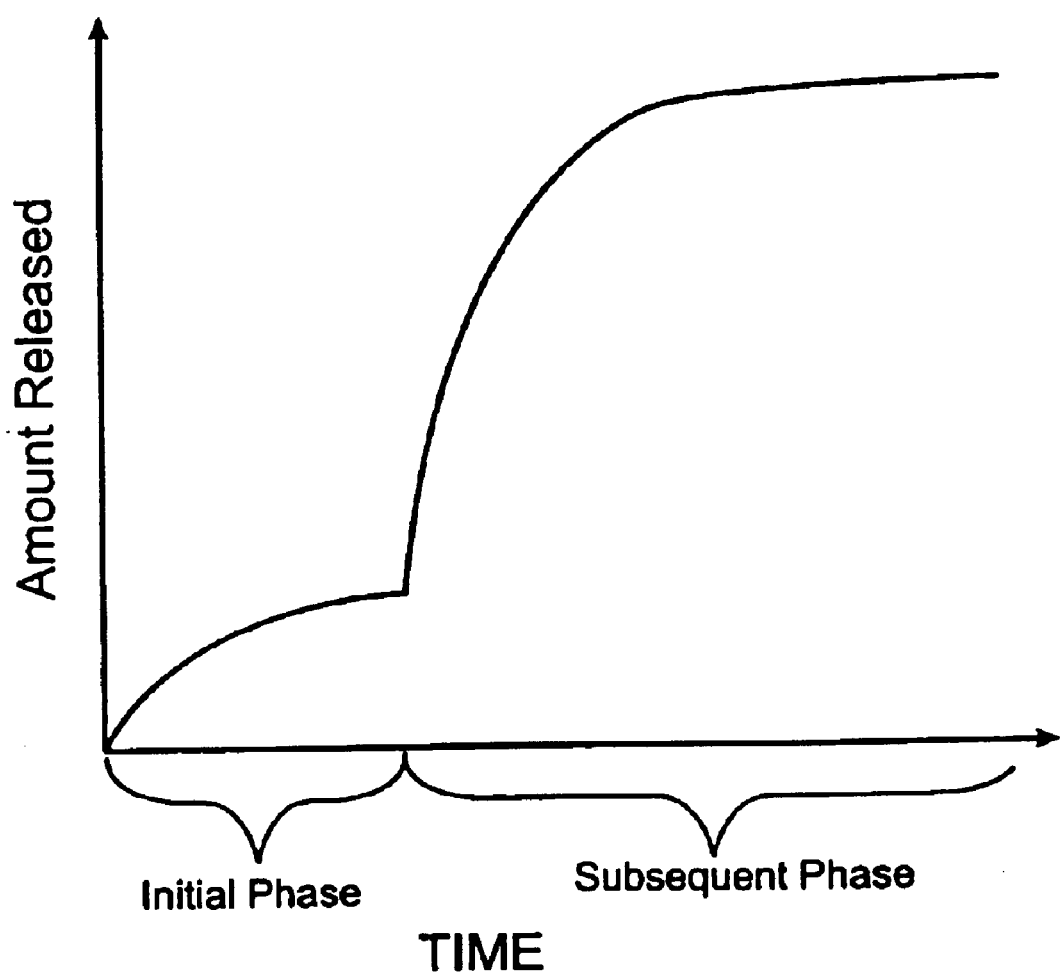
FIG. 16 is a graphical representation of the release of a therapeutic capable agent over a predetermined time period.

Referring now to FIG. 16, a graphical representation of an exemplary embodiment of therapeutic capable agent release over a predetermined time period is shown. The predetermined rate pattern shown in FIG. 16 of the present invention improves the efficacy of the delivery of the therapeutic capable agent to the susceptible tissue site by making the therapeutic capable agent available at none to some lower delivery rate during an initial phase. Once a subsequent phase is reached, the delivery rate of the therapeutic capable agent may be substantially higher. Thus, time delayed therapeutic capable agent release can be programmed to impact restenosis (or other targeted conditions as the case may be) at at least a partial formation of the initial cellular deposition or proliferation (hyperplasia). The present invention can further reduce the washout of the therapeutic capable agent by timing the release of the therapeutic capable agent to occur after at least initial cellularization. Moreover, the predetermined rate pattern may reduce the loading and/or concentration of the therapeutic capable agent. The predetermined rate pattern may further provide limited or reduced to no hindrance to endothelialization of the vessel wall due to the minimization of washout of the therapeutic capable agent and the increased efficiency of its release.

EXAMPLES

Example 1

A stainless steel Duraflex™ stent, having dimensions of approximately 3.0 mm×14 mm was sprayed with a solution of 25 mg/ml therapeutic capable agent in a 100% ethanol or methanol solvent. The stent was dried and the ethanol was evaporated leaving the therapeutic capable agent on the stent surface. A 75:25 PLLA/PCL copolymer (sold commercially by Polysciences) was prepared in 1,4 Dioxane (sold commercially by Aldrich Chemicals). The therapeutic capable agent coated stent was loaded on a mandrel rotating at 200 rpm and a spray gun (sold commercially by Binks Manufacturing) used to dispense the copolymer solution in a fine spray onto the coated stent, as the stent rotated for approximately a 10–30 second time period. The stent was then placed in an oven at 25–35° C. for up to 24 hours to complete the evaporation of the solvent.

Example 2

A stainless steel Duraflex stent (3.0×18 mm) was laser cut from a SS tube. The surface area of the stent for receiving the therapeutic capable agent was increased by increasing the surface roughness of the stent. The surface area and the volume of the stent can be further increased by creating 10 nm wide by 5 nm deep grooves along the links of the stent strut. The grooves were created in those stent areas experiencing low stress during expansion so as not to compromise the stent radial strength. The drug was loaded onto the stent and in the stent grooves by dipping or spraying the stent in the therapeutic capable agent solution prepared in low surface tension solvent such as isopropyl alcohol, ethanol, or methanol. The stent was then dried with the therapeutic capable agent remaining on the stent surface, and in the grooves which served as a reservoir for the therapeutic capable agent. Parylene was then vacuum deposited on the stent to serve as a rate-controlling barrier. The drug was eluted from the stent over a period of time in the range from 1 day to 45 days.

Example 3

A therapeutic capable agent was dissolved in methanol, then sprayed onto the stent. The stent was left to dry with the solvent evaporating from the stent leaving the therapeutic capable agent on the stent. A matrix or barrier (silicone, polyurethane, polytetrafluorethylene, parylast, parylene) was sprayed or deposited on the stent covering the therapeutic capable agent. The amount of therapeutic capable agent varied from about 100 micrograms to 2 milligrams, with release rates from 1 day to 45 days.

Example 4

A matrix solution including the matrix polymer and a therapeutic capable agent was coated onto a stent, as described in Example 2. The stent was then coated or sprayed with a top coat of a rate-controlling barrier (and/or a matrix material without a drug so as to act as a rate-controlling barrier). Alternatively, the therapeutic capable agent may be coated on a stent via a rate-controlling barrier, and then covered with a top coat (another barrier or matrix). Use of topcoats provides further control of release rate, improved biocompatibility, and/or resistance to scratching and cracking upon stent delivery or expansion.

Example 5

The therapeutic capable agent may be combined with a second therapeutic capable agent (cytotoxic drugs, cytostatic drugs, or psoriasis drugs). One agent is in or coupled to a first coat while other agent is in or coupled to a second coat. The therapeutic capable agent is released for the first 1–3 weeks after being implanted within a vessel while the second therapeutic capable agent is released or continues to be released for a longer period.

Example 6

A combination of multiple therapeutic capable agents that are individually included in different coats can be used as the matrix. The coats may release the multiple agents simultaneously and/or sequentially. The agents may be selected from a therapeutic capable agent class of inhibitors of de novo nucleotide synthesis or from classes of glucocorticosteroids, immunophilin-binding drugs, deoxyspergualin, FTY720, protein drugs, or peptides. This can also apply to any combination of agents from the above classes that are coupled to a stent with the addition of other cytotoxic drugs.

Example 7

A matrix including the therapeutic capable agent, mycophenolic acid, and matrix polymer, CAB (cellulose acetate butyrate); at a mycophenolic acid loading of 70% to 80% by weight was prepared by dissolving the therapeutic capable agent in acetone at 15 mg/ml concentration, dissolving CAB in acetone at 15 mg/ml concentration, and thereafter mixing together the mycophenolic acid and CAB solutions in 3:1 portion matrix solution. The amount of therapeutic capable agent varied from about 0.1 microgram to about 2 mg, preferably, at 600 microgram. The matrix solution was then coated onto two sets of stents (Sets A and B) by spraying them with an atomizer sprayer (EFD manufacturer) while each stent was rotated. Each stent was allowed to let dry. One matrix-coated stent was then coated with parylene as the rate-controlling barrier (about 1.1 μm) using methods similar to those described in Example 2. Orifices were created on the top surface (parylene rate-controlling barrier) of the stent of Set B by subjecting the surface to laser beams or needle. The orifice size can range from about 0.1 μm to about 100 μm in diameter. The orifice in Set B stent was about 10 μm in diameter. An orifice can be about 0.003 to about 2 inches apart from the next orifice (measured as the curvilinear distance as you trace along the stent strut pattern).

Figure 17A:
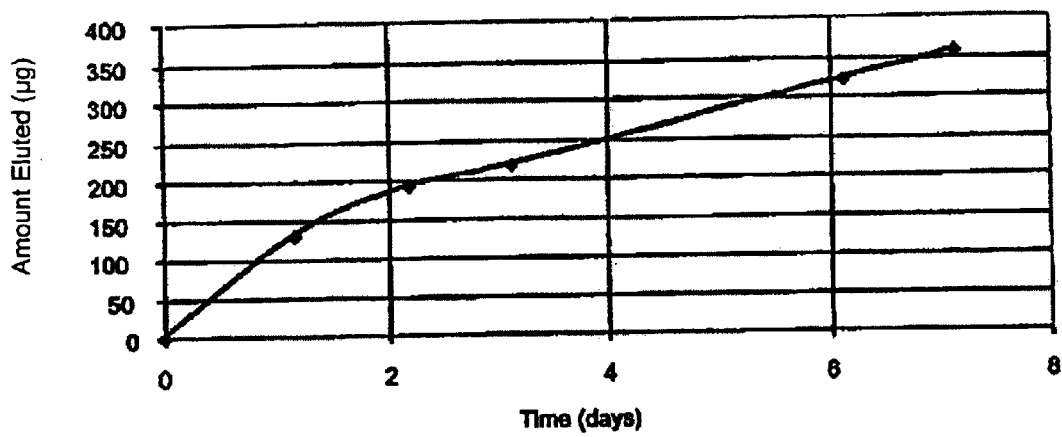
FIGS. 17A, 17B, 18A, 18B, 19A through 19E, 20A, 20B, 21A, and 21B are graphical representations of the performance of various therapeutic capable agents.
Figure 17B:
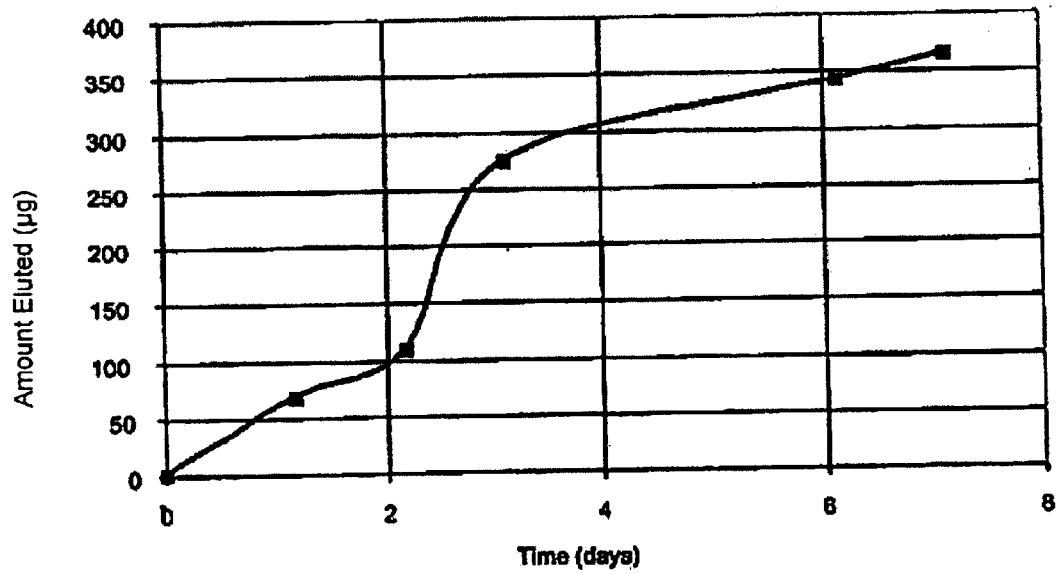

The mycophenolic acid loaded stents were placed in an elution solution of porcine serum and allowed to age for a period of 1 to 7 days. Samples from the serum were taken at regular time intervals and analyzed by HPLC. As can be seen from the data represented in FIGS. 17A and 17B (corresponding to stent sets A and B, respectively), Stent Set A showed a linear release rate for the mycophenolic acid while stent Set B showed a relatively slow linear release rate at the initial phase, followed by a relatively more rapid release in the subsequent phase.

Example 8

Figure 18A:
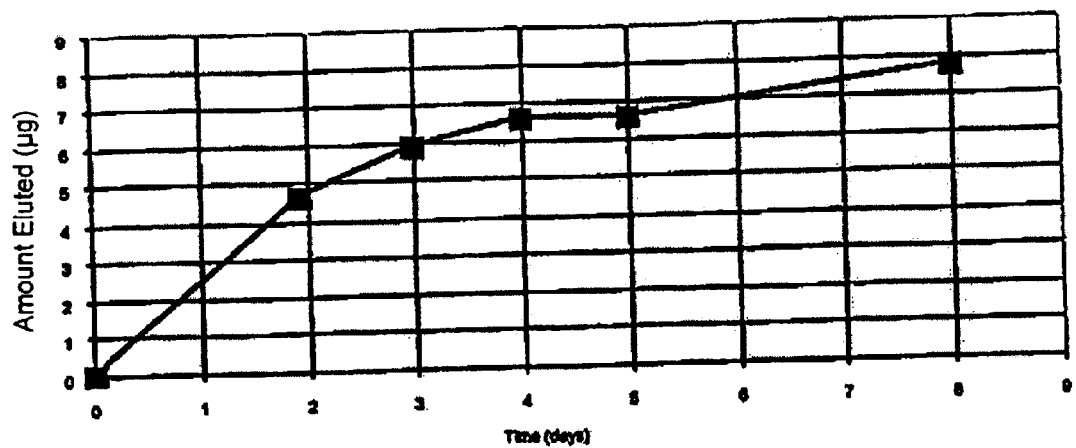
Figure 18B:
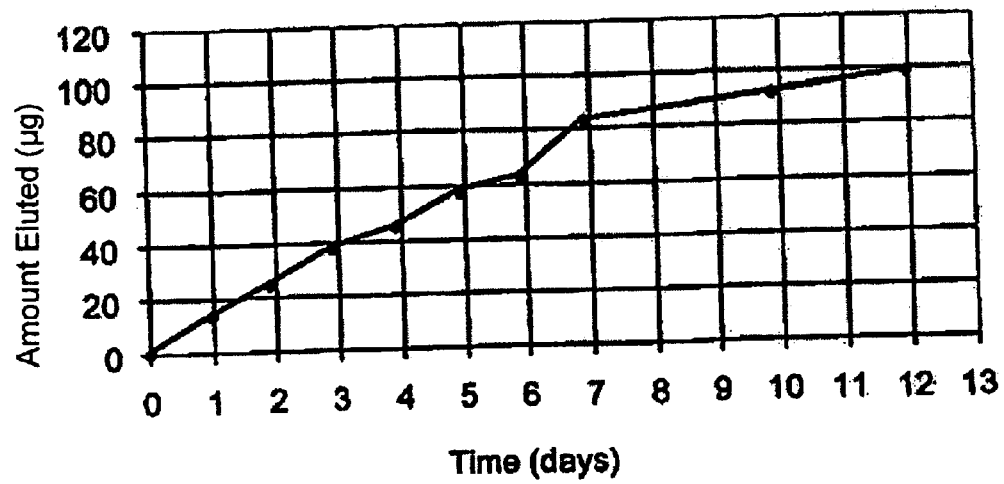

Two sets of stents, Sets A and B, were coated with 250 and 300 g of mycophenolic acid, respectively, according to Example 2. Set A was then coated with 1.7 micron of parylene as the rate-controlling barrier. Set B was first coated with mycophenolic acid followed by a subsequent coating of methylprednisolone as the rate-limiting matrix material, and thereafter coated with 1.3 micron of parylene. The coated stents were then subjected to in vitro elution test as described in Example 7, and the amount of mycophenolic acid eluted was measured. As can be seen from the data represented in FIGS. 18A and 18B (corresponding to stent Sets A and B, respectively), both Sets showed a relatively fast linear release of the mycophenolic acid in the initial phase followed by a relatively slower release in the subsequent phase. This may suggest that the more hydrophobic methylprednisolone may act as a rate-controlling element for the more water soluble mycophenolic acid, and can act to control the release rate of mycophenolic acid along with the Parylene coating. This is useful when the diseased area needs a large bolus of the drug initially and then a sustained slower release.

Example 9

Figure 19A:
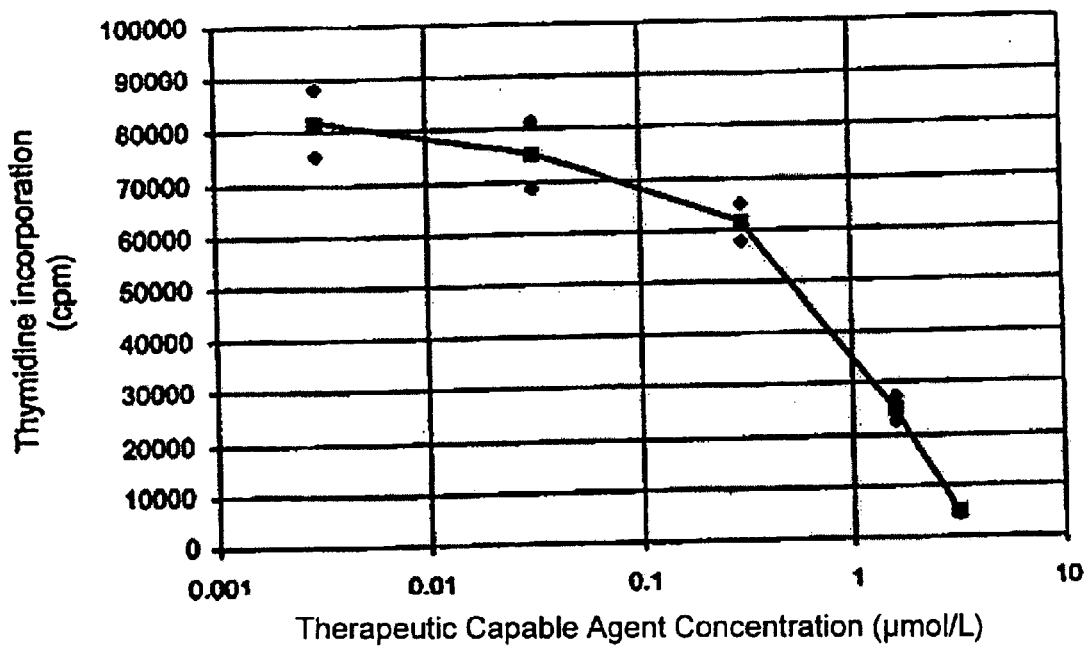
Figure 19B:
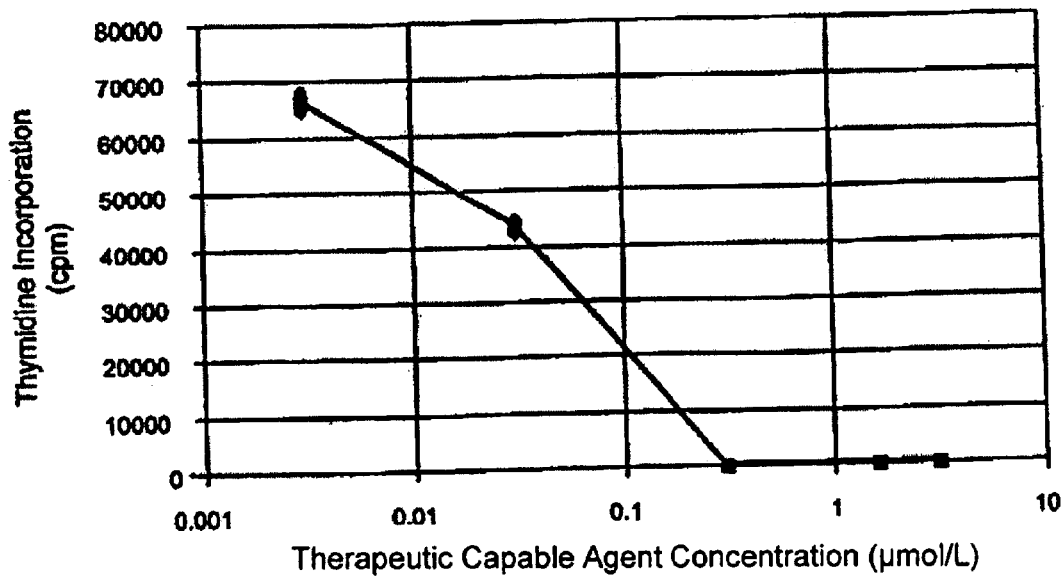
Figure 19C:
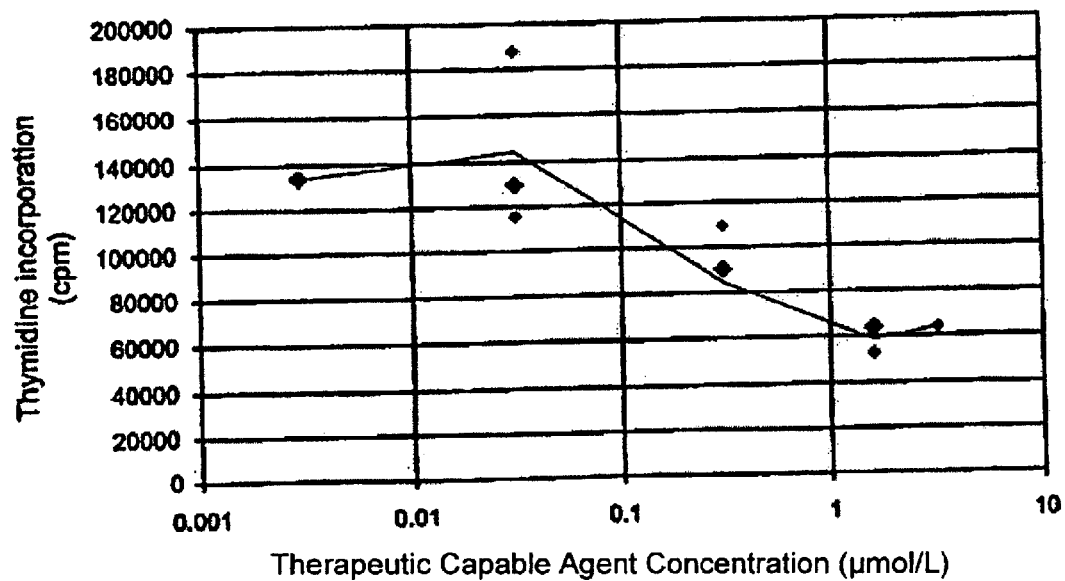
Figure 19D:
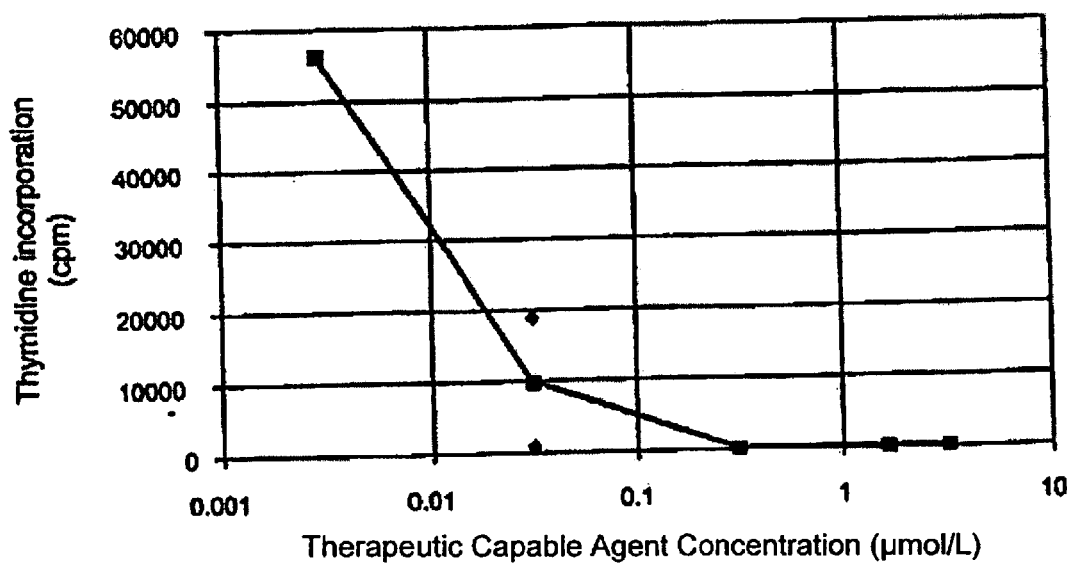
Figure 19E:
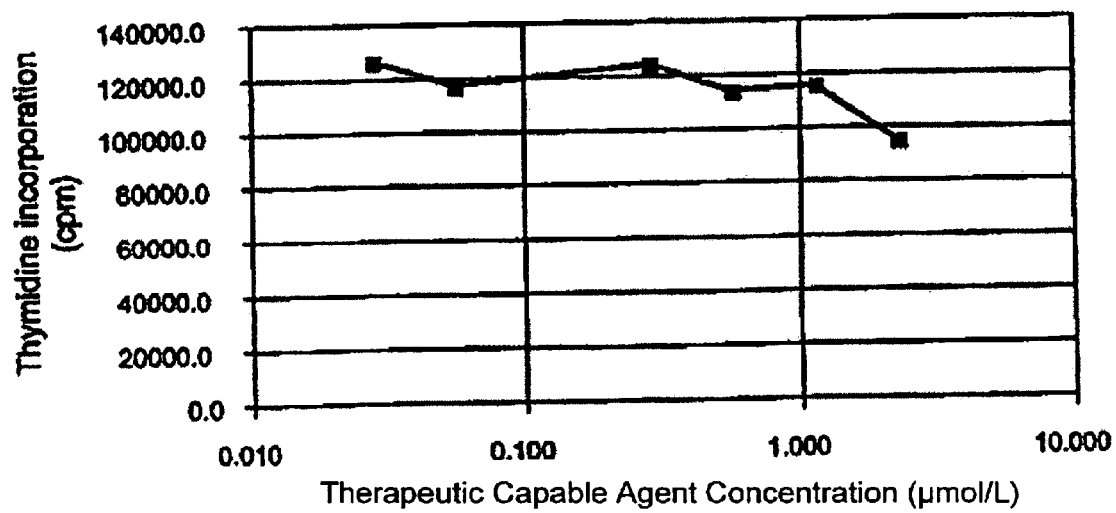

In order to assess the effect of therapeutic capable agents of the present invention on cell cultures, samples of 5 sets of therapeutic capable agents, as listed below, in varying concentrations were prepared and added to different groups of porcine smooth muscle cell cultures according to standard procedures. Set A, B, C, D, and E corresponded to therapeutic capable agent sets: Mycophenolic acid & Dexamethasone; Mycophenolic acid & Triptolide; Wortmannin and Methotrexate; Triptolide; Mycophenolate Mofetil; respectively. The amount of incorporated thymidine for the different samples of varying concentrations (0.003, 0.031, 0.31, 1.6, and 3.1 micromolar) was measured. As can be seen from the data represented in FIGS. 19A–9E (corresponding to Sets A–E, respectively) the IC50 (defined as the concentration at which 50% of the cells are prevented from proliferating) for the various sets occurred at different concentrations. As can further be noted, Mycophenolate Mofetil (reference E) may not be as effective in the absence of a bio-condition (e.g., subject to bodily fluids such as blood).

Example 10

Figure 20A:
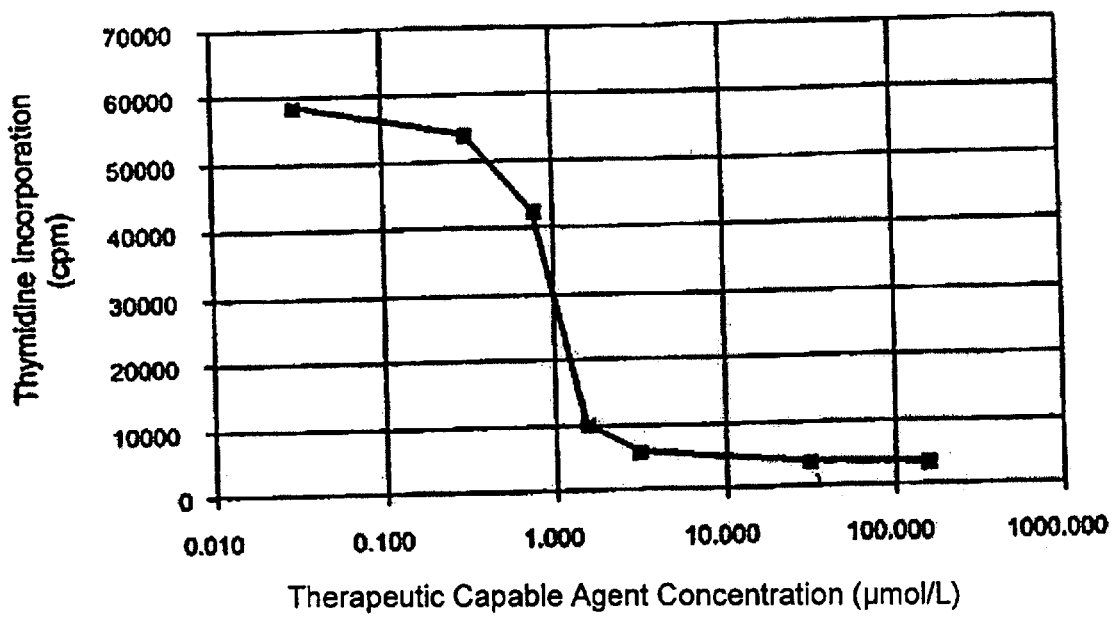
Figure 20B:
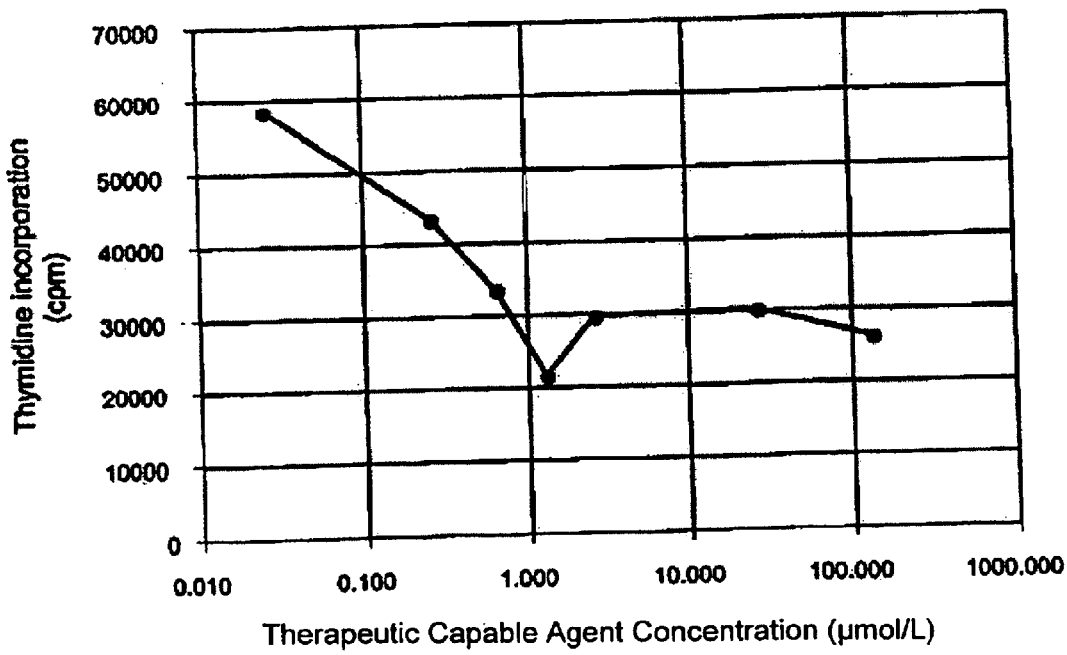

In another group of therapeutic capable agents, the amount of incorporated thymidine for samples of varying concentrations (0.003, 0.031, 0.31, 1.6, 3.1, 31, and 156 micromolar) was measured. As can be seen from the data represented in FIGS. 20A–10B, and corresponding to Mycophenolic acid and Methylprednisolone, respectively, the IC50 for these therapeutic capable agent was 1.0 micromolar.

Example 11

Figure 21A:
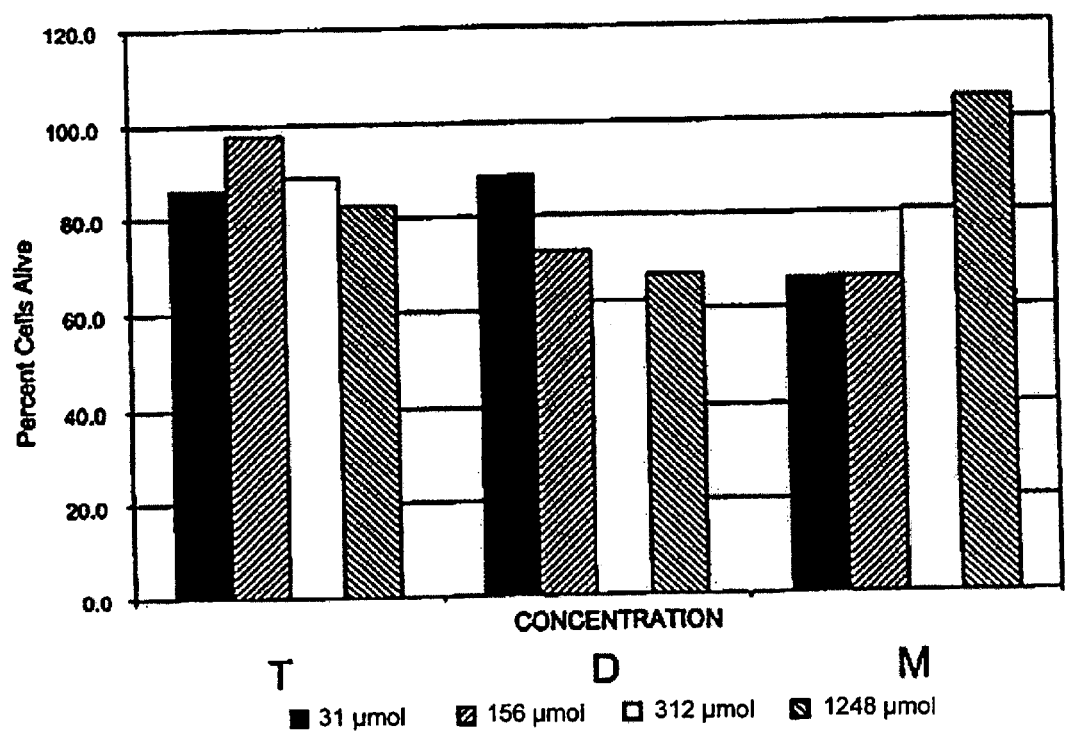
Figure 21B:
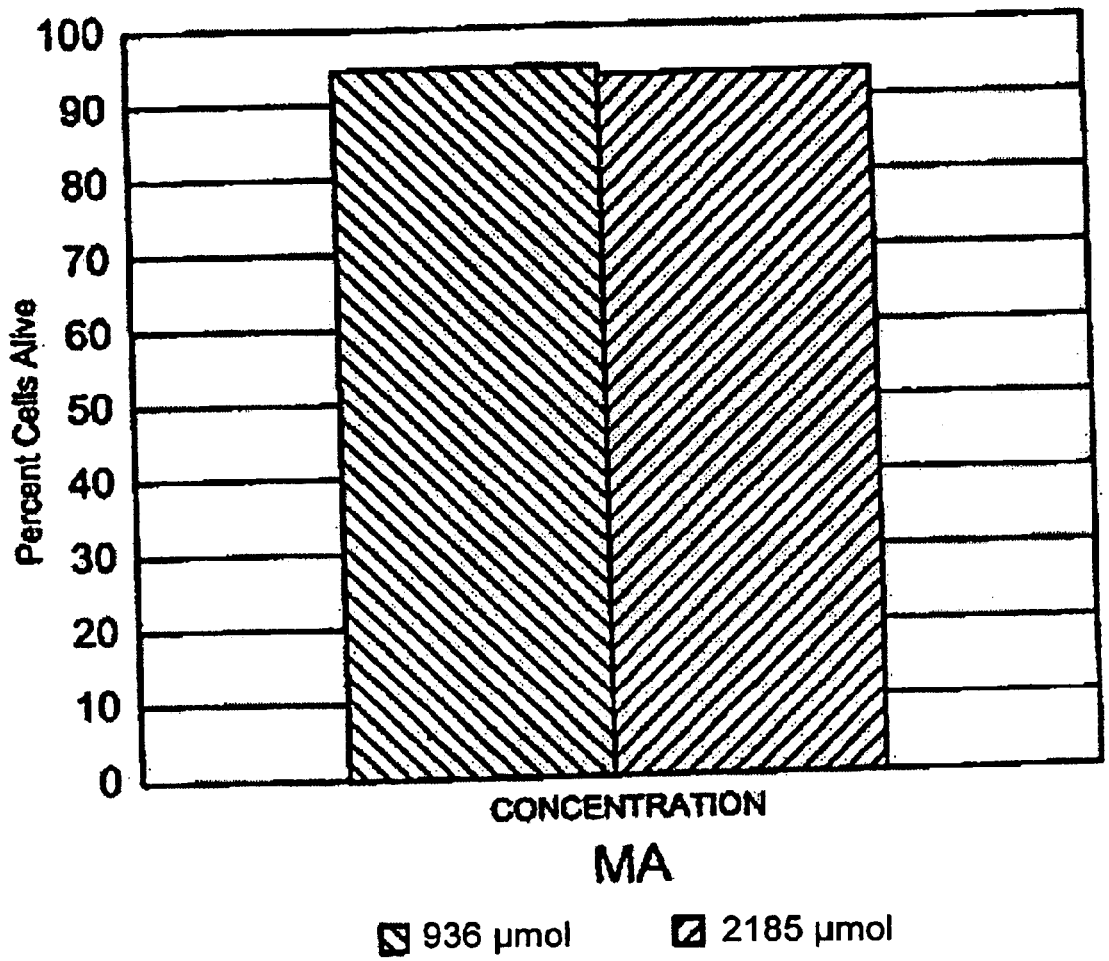

In order to assess the effect of various therapeutic capable agents, cell cultures were subjected to some therapeutic capable agents, using methods similar to those described in Examples 9 and 10. As can be seen from data represented in FIGS. 21A–21B, and corresponding, respectively, to Triptolide (T), Dexamethasone (D), Methotrexate (M); and Mycophenolic Acid (MA); the therapeutic capable agents did not lead to significant cell death. In addition, it can be seen that at the IC50 concentrations, most of the cells were alive yet 50% proliferating.

Example 12

A therapeutic capable agent, mycophenolic acid, was prepared by dissolving the therapeutic capable agent in acetone at 15 mg/ml concentration. The amount of therapeutic capable agent varied from about 0.1 µg to about 2 mg, preferably, at 600 µg. The drug solution was then coated onto or over a stent as described in Example 8 by spraying them with an atomizer sprayer (EFD manufacturer) while the stent was rotated. The stent was allowed to let dry. The stent was then placed over the tri-fold balloon on a PTCA catheter and crimped thereon. After crimping, the drug remained intact and attached to the stent. Expansion of the stent against a simulated Tecoflex vessel showed no cracking of the drug. Exposure of fluid flow over the stent before stent deployment against the simulated vessel did not result in drug detachment from the stent.

Example 13

In an embodiment when BSA is disposed adjacent an exterior surface of the rate-controlling element, mycophenolic acid (MPA) was bound to the BSA forming a MPA-BSA complex which is more stable than mycophenolic acid alone, thus decreasing the metabolism of mycophenolic acid to its glucuronide derivative (which is biologically inactive). The MPA-BSA has an increases half time (as measured by assaying methods such as liquid chromotography) as compared to mycophenolic acid alone and as shown in the table below:

| Blood or Tissue BSA Concentration (%) | Half Life (T) (minutes) |
| --- | --- |
| 1 | 76 |
| 2 | 121 |
| 4 | 364 |
| 6 | 1924 |

Example 14

Figure 22:
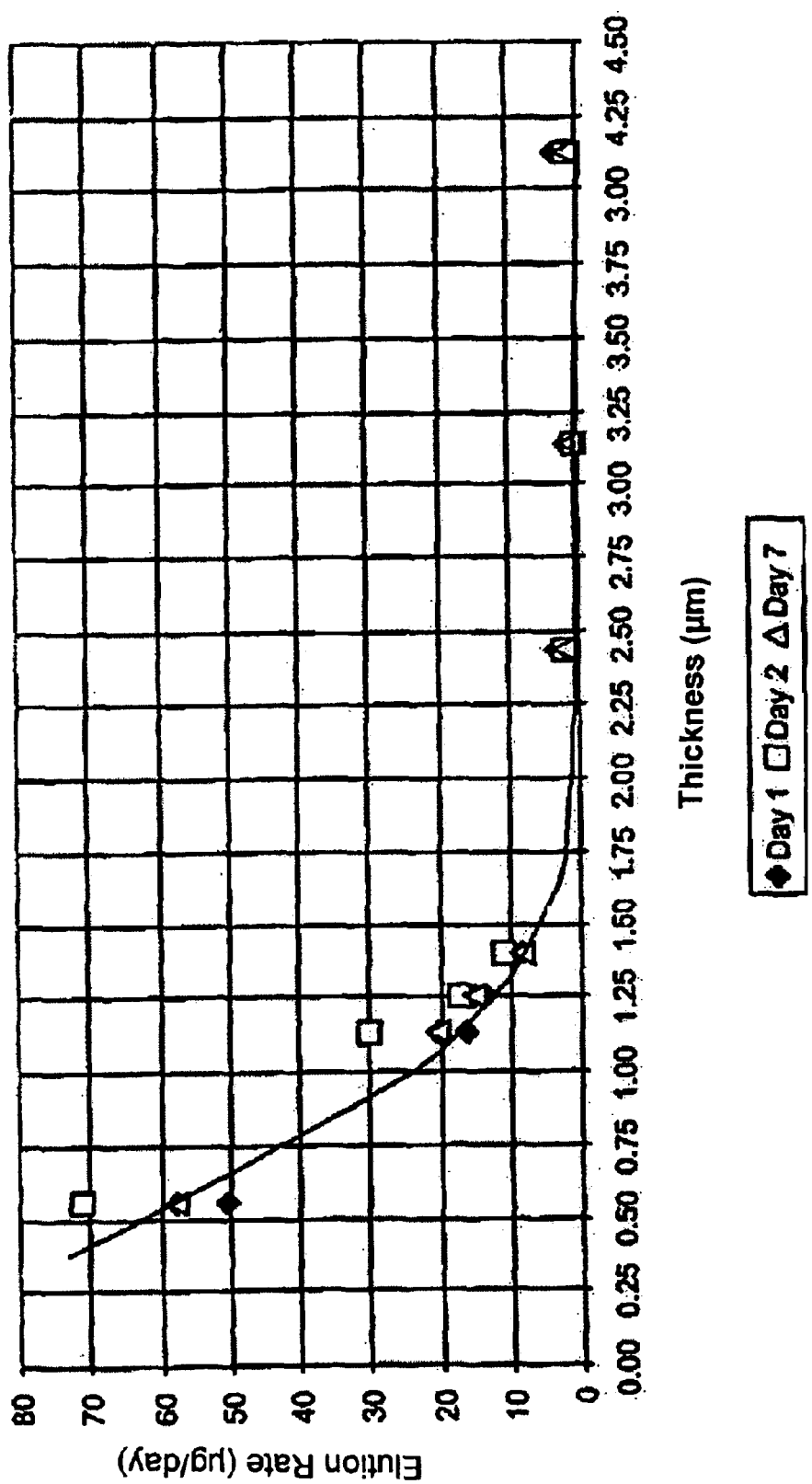
FIG. 22 are graphical representations of the performance of stents having different thicknesses of rate-controlling element.

A series of stainless steel Duraflex™ stent, having dimensions of approximately 3.5 mm×18 mm were sprayed with about 600 µg of therapeutic capable agent using a solution of 15 mg/ml therapeutic capable agent in a 100% methanol solvent. The stents were dried and the solvent was evaporated leaving the therapeutic capable agent on the stents surfaces. Parylene C was then vacuum deposited on the stents to serve as a rate-controlling barrier. The amount/thickness of the parylene was varied so as to create stents having different rate-controlling element thicknesses. The coated stents were place in porcine serum at 37° C. The therapeutic capable agent was eluted from the stents over a period of time and the amount eluted was measured using HPLC. As can be seen from FIG. 22, the elution rate for the stents decreased as the thickness of the rate-controlling element increased.

Example 15

Figure 23A:
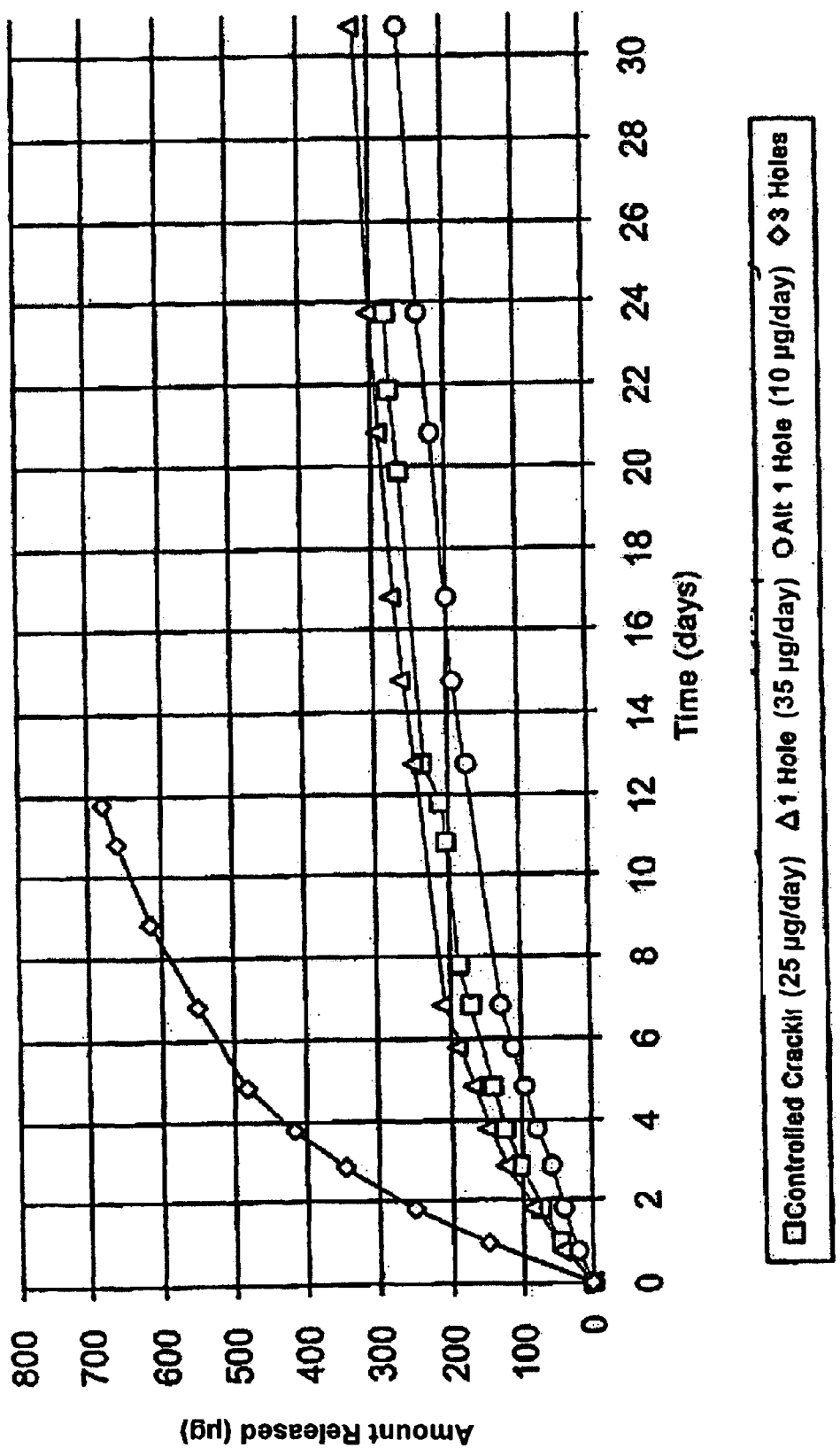
FIGS. 23A and 23B are graphical representation of different embodiments of stents showing the effect of apertures in the rate-controlling element on release rate of therapeutic capable agent.
Figure 23B:
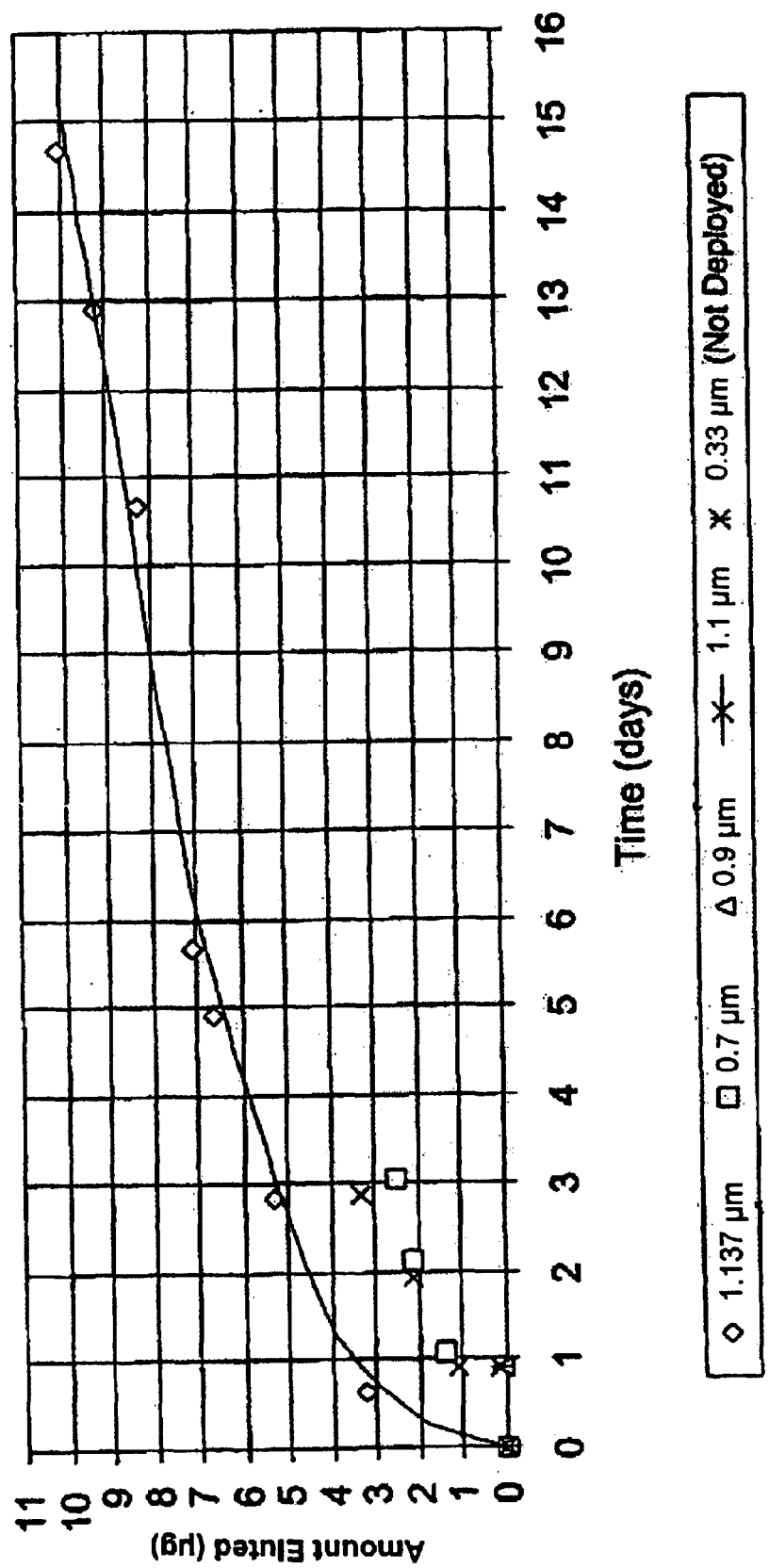

A number of stainless steel Duraflex™ stents, having dimensions of approximately 3.5 mm×18 mm were sprayed with about 700 mg of therapeutic capable agent using a solution of 15 mg/ml methylprednisolone in a 70% acetone: 30% methanol solvent. The stents were dried and the ethanol was evaporated leaving the therapeutic capable agent on the stents surfaces. Parylene C was then vacuum deposited on the stents to serve as a rate-controlling element, at varying thicknesses. One series of the stents having a rate-controlling element layer thickness of about 1.1 micron was then further processed to include apertures, having nominal diameter of about 0.0005 inch, in the rate-controlling element layer similar to embodiment in FIG. 9B, in configurations of: one aperture on every strut, one aperture on every other strut, 3 apertures on every strut, and a controlled disruption on every strut (e.g., FIG. 9C). The coated stents were place in porcine serum at 37° C. The therapeutic capable agent was eluted from the stents over a period of time and the amount eluted was measured using HPLC. As can be seen from FIGS. 23A (with aperture or disruptions) and 23B (without apertures or disruptions), the amount of therapeutic capable agent eluted increased for both series (with and without apertures) with increase in the elution period, with the eluted amount increasing as the number of the apertures increases.

Example 16

Figure 24:
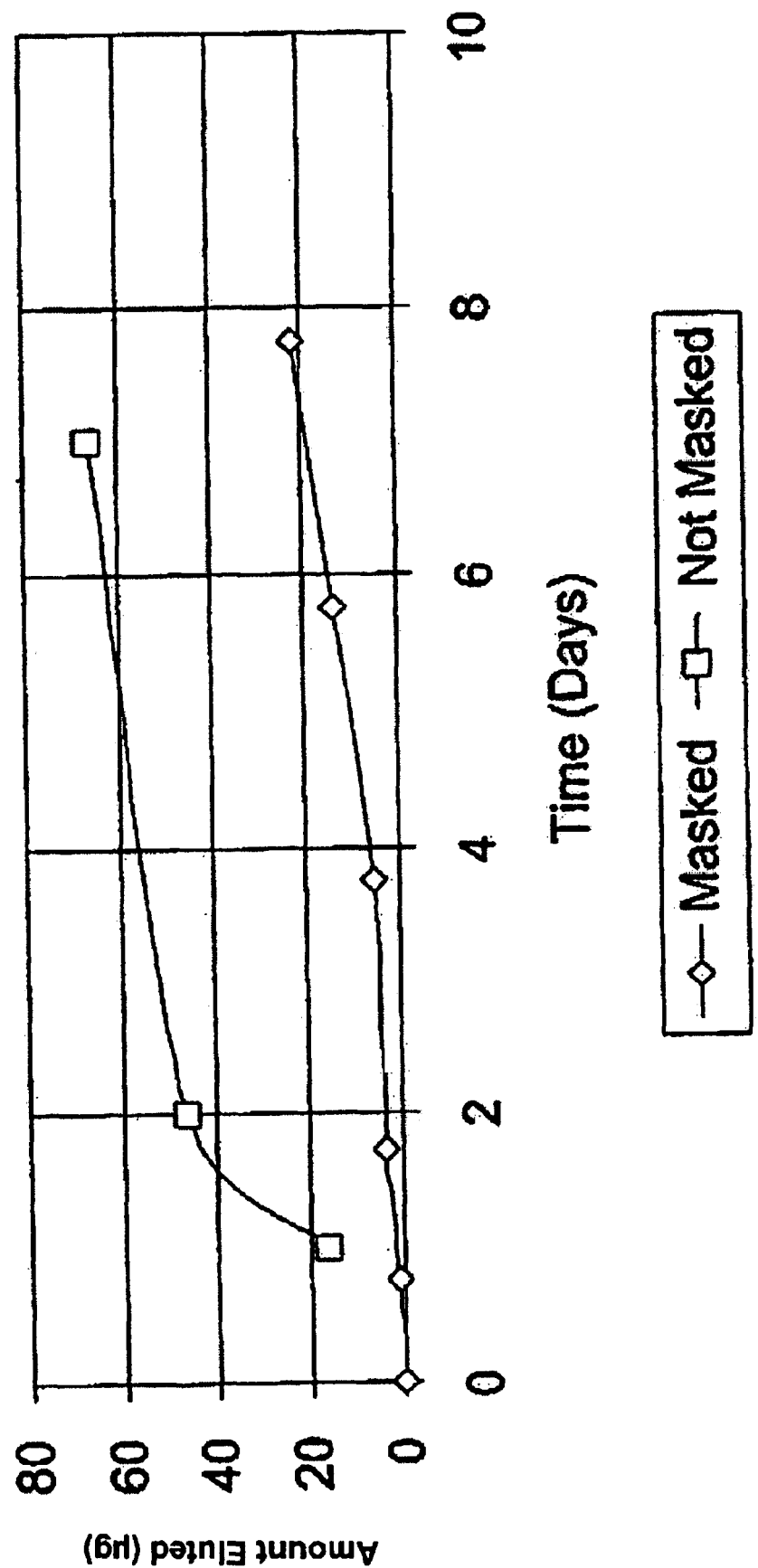
FIG. 24 is a graphical representation of the stent of FIG. 4A showing the effect of masking during coating of the therapeutic capable agent.

A series of stainless steel Duraflex™ stents, having dimensions of approximately 3.5 mm×18 mm were first masked on the higher stress areas of the stents, according to the embodiment described with respect to FIG. 14C with a tape. The stents were then sprayed with 600 μg of therapeutic capable agent using a solution of 15 mg/ml mycophenolic acid as the therapeutic capable agent in a 100% methanol solvent. The stents were dried and the solvent was evaporated leaving the therapeutic capable agent on the lower stress areas of the stents. The mask was removed and Parylene C was then vacuum deposited on the stents to serve as a rate-controlling element with a nominal thickness of about 1.1 micron. The therapeutic capable agent was eluted from the stents over a period of time. As can be seen from FIG. 24, the stent having been coated with the therapeutic capable agent only on the low stress areas (using masking) elutes at a lower amount than the one coated with the therapeutic capable agent on both the high and low stress areas, allowing for a more controlled release of the therapeutic capable agent.

Example 17

Figure 25:
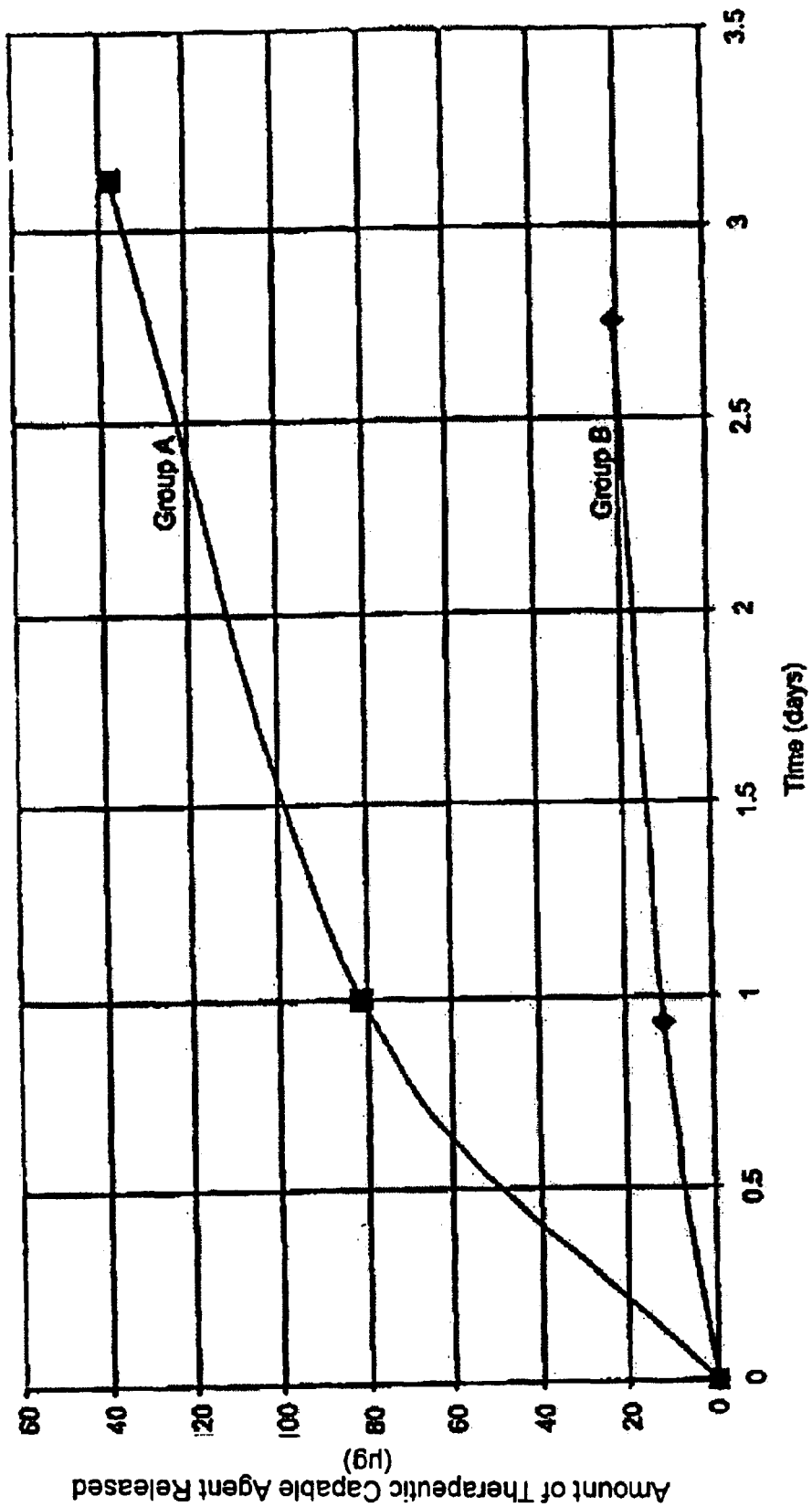
FIG. 25 is a graphical representation of the stent of FIG. 4A showing the effect of heating of stent on the release of therapeutic capable agent.

A series of stainless steel Duraflex™ stents, having dimensions of approximately 3.5 mm×18 mm were sprayed with 300 μg of therapeutic capable agent using a solution of 15 mg/ml mycophenolic acid as the therapeutic capable agent in a 100% methanol solvent. The stents were dried and the solvent was evaporated leaving the therapeutic capable agent on the lower stress areas of the stents. Parylene C was then vacuum deposited on the stents to serve as a rate-controlling element with a nominal thickness of about 2 to 8 microns. The therapeutic capable agent/rate-controlling element-coated stents were then divided in two groups with the second group further being heated to about 145° C. for about 1 hour. The therapeutic capable agent was eluted from the stents over a period of time. As can be seen from FIG. 25, the stent having been heated (Group B) after the final coating of the device had a lower amount of therapeutic capable agent released over the same period of time.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A device for intracorporeal use within a patient's body, comprising:
   an implantable scaffold;
   at least one source of at least one therapeutic capable agent having a degree of crystallinity less than about 90% and associated with the scaffold and configured to release the therapeutic capable agent within the patient's body; and
   a rate-controlling element disposed adjacent at least a portion of the source and being configured to control the release of the therapeutic capable agent to the patient's body.

2. A device as in claim 1 wherein the therapeutic capable agent has a degree of crystallinity less than about 50%.

3. A device as in claim 1 wherein the at least one source of at least one therapeutic capable agent has a degree of crystallinity less than about 50%.

4. A device as in claim 1 wherein the at least one source of at least one therapeutic capable agent as formed on the scaffold has a degree of crystallinity less than about 90%.

5. A device as in claim 1 wherein the at least one source of at least one therapeutic capable agent as formed on the scaffold has a degree of crystallinity less than about 50%.

6. A device as in claim 1 wherein the at least one therapeutic capable agent as formed on the scaffold has a degree of crystallinity less than about 90%.

7. A device as in claim 1 wherein the at least one therapeutic capable agent as formed on the scaffold has a degree of crystallinity less than about 50%.

8. A device as in claim 1 wherein the at least one therapeutic capable agent has a degree of crystallinity less than about 90%.

9. A device as in claim 1 wherein the at least one source comprises a matrix including the at least one therapeutic capable agent.

10. A device as in claim 1 wherein the at least one source comprises the at least one therapeutic capable agent.

11. A device for intracorporeal use within a patient's body, comprising:
    an implantable scaffold;
    at least one source of at least one therapeutic capable agent associated with the scaffold and configured to release the therapeutic capable agent at a targeted tissue site within the patient's body; and
    a rate-controlling element disposed adjacent at least a portion of the source and being configured to effectuate a therapeutic capable agent flux density of about $1.71 \times 10^{-14}$ g/(cm$^2$s) to about $1.71 \times 10^{-8}$ g/(cm$^2$s).

12. A device for as in claim 11 wherein the flux density ranges from about $1.71 \times 10^{-14}$ g/(cm$^2$s) to about $3.43 \times 10^{-9}$ g/(cm$^2$s).

13. A device for as in claim 11 wherein the flux density ranges from about $8.57 \times 10^{-12}$ g/(cm$^2$s) to about $3.43 \times 10^{-9}$ g/(cm$^2$s).

14. A device for as in claim 11 wherein the flux density ranges from about $1.71 \times 10^{-11}$ g/(cm$^2$s) to about $1.03 \times 10^{-9}$ g/(cm$^2$s).

15. A device as in claim 11 wherein the at least one source comprises a matrix including the at least one therapeutic capable agent.

16. A device as in claim 11 wherein the at least one source comprises the at least one therapeutic capable agent.

17. A device for intracorporeal use within a patient's body, comprising:
    an implantable scaffold;
    at least one source of at least one therapeutic capable agent associated with the scaffold and configured to release the therapeutic capable agent at a targeted tissue site within the patient's body; and
    a rate-controlling element disposed adjacent at least a portion of the source and being configured to control the release of the therapeutic capable agent in the patient's body, the device having a residual stress in an unexpanded state less than about 10%.

18. A device for as in claim 17 wherein the residual stress is less than about 5%.

19. A device for as in claim 17 wherein the residual stress is less than about 1%.

20. A device for as in claim 17 wherein the residual stress is less than about 0.5%.

21. A device as in claim 17 wherein the at least one source comprises a matrix including the at least one therapeutic capable agent.

22. A device as in claim 17 wherein the at least one source comprises the at least one therapeutic capable agent.

23. A device for intracorporeal use within a patient's body, comprising:

an implantable scaffold;

at lease one source of at least one therapeutic capable agent associated with the scaffold and configured to release the therapeutic capable agent within the patient's body; and a rate-controlling element layer covering at least a portion of the source and being formed from a non-porous material.

24. A device as in claim 23, wherein the non-porous material comprises parylene.

25. A device as in claim 23, wherein the nonporous material becomes at least partially porous when exposed to conditions in the patient's body.

26. A device as in claim 23, wherein the rate-controlling element becomes disrupted when exposed to conditions in the patient's body.

27. A device as in claim 23, wherein the rate-controlling element includes a therapeutic capable agent.

28. A device as in claim 27, wherein the therapeutic capable agent in the rate controlling element is the same as the therapeutic capable agent in the source.

29. A device as in claim 23, wherein the nonporous material is selected from the group consisting of plasma deposited polymers, sputtered materials, evaporated materials, electroplated metals, electroplated alloys, glow discharge coatings, polyethylenes, polyurethanes, silicone rubber, cellulose, and parylene.

30. A device as in claim 23 wherein the at least one source comprises a matrix including the at least one therapeutic capable agent.

31. A device as in claim 23 wherein the at least one source comprises the at least one therapeutic capable agent.

* * * * *